(12) United States Patent
Bracke et al.

(10) Patent No.: US 9,290,427 B2
(45) Date of Patent: Mar. 22, 2016

(54) ANTI-INVASIVE COMPOUNDS

(71) Applicant: Universiteit Gent, Ghent (BE)

(72) Inventors: Marc Bracke, Wondelgem (BE); Christian Stevens, Merelbeke (BE); Tine De Ryck, Sint-Niklaas (BE); Bart Roman, Kortrijk (BE); Barbara Vanhoecke, Wanniassa (AU)

(73) Assignee: Universiteit Gent, Gent (BE)

( * ) Notice: Subject to any disclaimer, the term of this patent is extended or adjusted under 35 U.S.C. 154(b) by 0 days.

(21) Appl. No.: 14/375,270

(22) PCT Filed: Jan. 30, 2013

(86) PCT No.: PCT/EP2013/051728
§ 371 (c)(1),
(2) Date: Jul. 29, 2014

(87) PCT Pub. No.: WO2013/113722
PCT Pub. Date: Aug. 8, 2013

(65) Prior Publication Data
US 2015/0011620 A1  Jan. 8, 2015

(30) Foreign Application Priority Data

Jan. 30, 2012 (EP) .................................. 12153062
Jul. 6, 2012 (EP) .................................. 12175223

(51) Int. Cl.
| | | |
|---|---|---|
| *A61K 31/341* | (2006.01) | |
| *C07D 307/46* | (2006.01) | |
| *C07C 49/223* | (2006.01) | |
| *A61K 31/12* | (2006.01) | |
| *A61K 31/34* | (2006.01) | |
| *G06F 19/00* | (2011.01) | |

(52) U.S. Cl.
CPC .............. *C07C 49/223* (2013.01); *A61K 31/12* (2013.01); *A61K 31/34* (2013.01); *C07D 307/46* (2013.01); *G06F 19/704* (2013.01)

(58) Field of Classification Search
CPC .......................... A61K 31/341; C07D 307/46
USPC .................................................. 514/461, 679
See application file for complete search history.

(56) References Cited

U.S. PATENT DOCUMENTS

| | | |
|---|---|---|
| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |

FOREIGN PATENT DOCUMENTS

| | | |
|---|---|---|
| WO | 0202593 A2 | 1/2002 |
| WO | 0202593 A3 | 1/2002 |
| WO | 03037315 A1 | 5/2003 |

OTHER PUBLICATIONS

Bracke M. E. et al.: "Plant polyphenolics as anti-invasive cancer agents", Anti-Cancer Agents in Medicinal Chemistry, vol. 8, No. 2, Feb. 2008, pp. 171-185, XP008153109, ISSN: 1871-5206.
Katritzky A. R. et al.: "QSAR modeling of anti-invasive activity of organic compounds using structural descriptors", Bioorganic & Medicinal Chemistry, Pergamon, GB, vol. 14, No. 20, Oct. 15, 2006, pp. 6933-6939, XP027992975, ISSN: 0968-0896.
Parmar V S et al.: "Anti-invasive Activity of Alkaloids and Polyphenolics in Vitro", Bioorganic & Medicinal Chemistry, Pergamon, GB, vol. 5, No. 8, Jan. 1, 1997, pp. 1609-1619, XP002226722, ISSN 0968-0896, DOI: 10.1016/S0968-0896(97)00091-6.
Edwards M L et al.: "Chalcones: A New Class of Antimitotic Agents", Journal of Medicinal Chemistry, American Chemical Society, US, vol. 33, No. 7, Jul. 1, 1990, pp. 1948-1954, XP001015662, issn: 0022-2623, doi: 10.1021/jm00169A021.
Romagnoli R et al.: "Design, synthesis, and biological evaluation of thiophene analogues of chalcones", Bioorganic & Medicinal Chemistry, Pergamon, GB, vol. 16, No. 10, May 15, 2008, pp. 5367-5376, XP022673119, ISSN: 0968-0896, DOI: 10.1016/J.BMC.2008-04.026.
Bhat B A et al: "Synthesis and biological evaluation of chalcones and their derived pyrazoles as potential cytotoxic agents", Bioorganic & Medicinal Chemistry Letters, Pergamon, Elsevier Science, GB, vol. 15, No. 12, Jun. 15, 2005, pp. 3177-3180, XP004915621, ISSN: 0960-894X, DOI: 10.1016/J.BMCL.2005.03.121.
Abdel Bar F M et al: "Design pharmacophore modeling of biaryl methyl eugenol analogs as breast cancer invasion inhibitors", Bioorganic & Medicinal Chemistry Letters, Pergamon, Elsevier Science, GB, vol. 18, No. 2, Jan. 15, 2010, pp. 496-507, XP026835880, ISSN: 0968-0896.
Robinson T P et al.: "Synthesis and biological evaluation of aromatic enones related to curcumin", Bioorganic & Medicinal Chemistry Letters, Pergamon, Elsevier Science, GB, vol. 13, No. 12, Jun. 2, 2005, pp. 4007-4013, XP027638066, ISSN: 0968-0896.
Parmar, Virinder S. et al.: "Synthesis and anti-invasive activity of novel 1, 3-diarylpropenones", Indian Journal of Chemistry, Section B: Organic Chemistry Including Medicinal Chemistry, 37B(7), 628-643 CODEN: IJSBDB; ISSN: 0376-4699, 1998, XP008158429.
Bart I Roman et al.: "Exploration of the SAR of anti-invasive chalcones: Synthesis and biological evaluation of conformationally restricted analogues", Bioorganic & Medicinal Chemistry Letters, Pergamon, GB, vol. 20, No. 15, May 29, 2012, pp. 4812-4819, XP028428240, ISSN: 0968-0896, DOI: 10.1016/J.BMC.2012.05.069.

(Continued)

Primary Examiner — Golam M M Shameem
(74) Attorney, Agent, or Firm — Dinsmore & Shohl LLP

(57) ABSTRACT

The present invention relates to the field of anti-invasive compounds and methods for predicting the anti-invasive activity of said compounds, as well as their use in the prevention and/or treatment of diseases associated with undesired cell invasion; in particular, this invention relates to the field of anti-invasive chalcone-like compounds.

12 Claims, 8 Drawing Sheets

(56) References Cited

OTHER PUBLICATIONS

Figure 1:
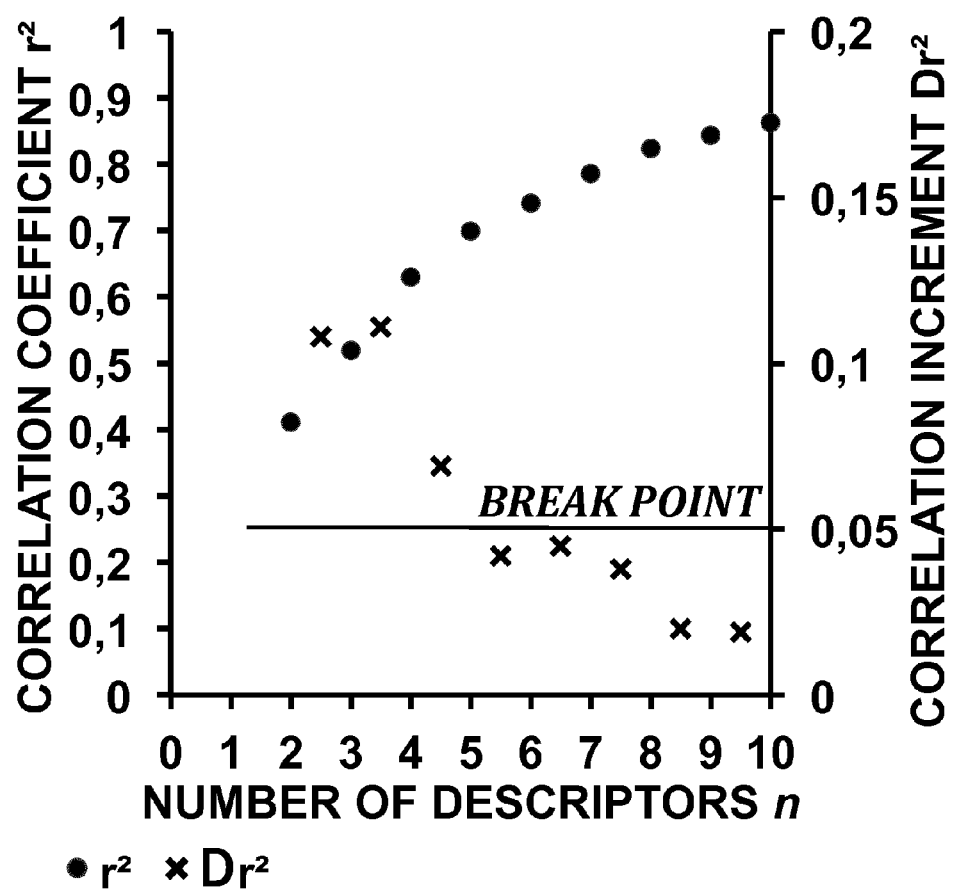

Chiaradia L. D. et al: "Synthesis and pharmacological activity of chalcones derived from 2,4,6-trimethoxyacetophenone in RAW 264.7 cells stimulated by LPS: Quantitative structure-activity relationiships", Bioorg. Med Chem., 2008, 16, pp. 658-667.

Ducki S. et al.: "Combretastatin-like chalcones as inhibitors of microtubule polymerization. Part 1: Synthesis and biological evaluation of antivascular activity", Bioorg. Med Chem., 2009, 17, pp. 7698-7710.

Mukherjee S. et al., "Synthetic and Biological Activity Evaluation Studies on Novel 1,3-Diarylpropenones", Bioorg. Med. Chem. 2001, 9, pp. 337-345.

Okunrobo L. O. et al., "Antiinflammatory and Gastroprotective Properties of Some Chalcones", Acta Pol Pharm., 2006, 63, pp. 195-199.

Parmar V. S. et al., "Synthesis, Characterization and In Vitro Anti-invasive Activity Screening of Polyphenolic and Heterocyclic Compounds", Bioorg. Med. Chem., 2003, 11, pp. 913-929.

Vanhoecke B. W. et al., "New anti-invasive compounds: Results from the Indo-Belgian screening program",Pure Appl. Chem., 2005, 1, pp. 65-75.

Yadav V. R. et al., "The roles of chalcones in suppression of NF-KB-mediated inflammation and cancer", International Immunopharmacology, 2011, 11, pp. 295-309.

International Preliminary Report on Patentability pertaining to International Application No. PCT/EP2013/051728 issued Aug. 5, 2014.

International Search Report completed Mar. 6, 2013 pertaining to International Application No. PCT/EP2013/051728.

ANTI-INVASIVE COMPOUNDS

FIELD OF THE INVENTION

The present invention relates to the field of anti-invasive compounds and methods for predicting the anti-invasive activity of said compounds, as well as their use in the prevention and/or treatment of diseases associated with undesired cell invasion; in particular, this invention relates to the field of anti-invasive chalcone-like compounds.

BACKGROUND TO THE INVENTION

Despite major advances in medicine in general, and in the field of oncology in particular, cancer remains a leading cause of death worldwide. In 2007, it accounted for 7.9 million fatalities or 13 of global mortality. Amongst women, breast cancer has the highest incidence, causing 548,000 deaths per annum. Hence, the 'war on cancer', declared by US president Nixon some four decades ago, is far from over.

A tumor is an abnormal growing cell mass, resulting from either an increased input of cells or a decreased output. Nonetheless, primary tumor growth is no longer the major therapeutic problem. Particularly for 'benign' or 'non-aggressive' tumors, surgical removal, radiotherapy, chemotherapy and immunotherapy have proven to be successful treatments for a great number of patients.

Fundamentally different, however, are 'malignant' or 'fast progressive' cancers, which are capable of invading into neighboring tissues, and subsequently spread to locoregional or distant organs, causing secondary tumors in permissive tissues. These processes, invasion and metastasis, are the foremost causes of cancer deaths and accordingly constitute a main challenge in cancer research. The molecular mechanisms of tumor invasion have been partly unraveled and originate from a disequilibrium between the expression of invasion promoter and invasion suppressor genes (Mareel et al., 1994). Interestingly, although invasion is crucial at all the different steps of the metastatic process, not every invasive tumor has a tendency to metastasize.

Existing studies or therapies are focusing on inhibition of mitosis (via microtubule assembly) and on proliferation (Edwards et al., 1990; Romagnoli et al. 2008; Bath et al., 2005; WO02/02593), or on inhibition of angiogenesis, the recruitment of new blood vessels (Robinson et al., 2005; WO02/02593; WO03/037315). In striking contrast to the new, efficient generation of growth-inhibiting drugs targeting specific growth signaling pathways in tumor cells (e.g. trastuzumab, imatinib and farnesyl transferase inhibitors), there are still no similar pharmaceuticals available to treat or prevent invasion and metastasis. Many anti-neoplastic compounds are designed to disrupt replication in rapidly dividing cells, or to inhibit a key metabolic link in actively proliferating cells. Although such approaches have met with levels of success in certain types of cancers, or cancers at certain stages, chemotherapy is generally associated with unpleasant to debilitating side effects due to their effects on normal cells, such as malaise, nausea, loss of appetite, alopecia, and anemia, and in the extreme, loss of immune function and/or loss of digestive activity. Further, compounds which act at the level of cell replication, either by introducing nucleotide analogs into dividing cells, or by disrupting normal replication, have the potential of introducing widespread genetic mutations in normal cells in the subject. In addition, cancer cells may develop resistance to many types of anti-cancer agents, either by limiting uptake of the agent into the cells, or by altering the metabolism of the agent within the cells.

Although angiogenesis inhibitors are designed to prevent the formation of new blood vessels, thereby stopping or slowing down the growth or spread of tumors, use of said compounds will not always result in the inhibition of invasion, since invasion can occur without angiogenesis. Even more, Pennaccietti et al. state that although angiogenesis inhibitors have shown promise in hindering blood supply and holding tumors in check it seems that such inhibitors, by depriving tumors of oxygen, could have an unintended effect, i.e. promotion of metastasis. Hence tumor cell resistance to antiangiogenic therapy through sustained viability or increased invasion may represent a previously unrecognized challenge.

At present, bisphosphonates are the most frequently applied drugs to treat bone metastases. Besides, microtubule (Atassi et al., 1982) and angiogenesis inhibitors (Jain et al., 2006) have been included in clinical trials to evaluate their anti-invasive and anti-metastatic activity.

Nevertheless, there is a continuous need for compounds specifically targeting the first steps of malignant tumor development, in particular inhibiting invasion. By specifically targeting the ability of tumor cells to invade neighboring tissue, an otherwise malignant tumor may be arrested at its initial site, and prevented from spreading throughout the body.

It was therefore an aspect of the present invention to provide compounds having specific anti-invasive activity. Furthermore, as for most pharmaceutical compounds, it is desirable to provide compounds having a lowest active concentration which is as low as possible to avoid undesired side-effects but still obtain the desired activity. In general in order to determine the lowest active concentration of a compound each individual compound needs to be synthesized and tested in vitro at different concentrations. However, as evident said method is far from efficient for testing a large set of compounds to select those having the best chance of success. It was therefore a further objective of this invention to provide a method suitable for in silico determining the lowest active concentration of a compound, thereby significantly reducing the number of potentially interesting compounds to be synthesized and tested in vitro.

In our quest for new anti-invasive agents, we have recently adopted a dual strategy of synthesis and modeling. Firstly, in search of new leads, we analyzed the results of the screening program of the Bracke group (Ghent University Hospital, Belgium), containing in vitro anti-invasive activity data for hundreds of compounds. Although few of the screened substances inhibit invasion of healthy tissues by MCF-7/6 carcinoma cells, the potentially interesting agents belong to very diverse categories: polyphenolics, peptides, steroids, phospholipids and retinoids. The promising potential of the polyphenolics was reflected in the establishment of the Indo-Belgian screening program, a collaborative effort of the Universities of Delhi and Ghent, which has systematically assessed the in vitro anti-invasive activity of polyphenolics and alkaloids since 1989 (Vanhoecke et al., 2005). Looking closer at the results of this collaboration, our attention was primarily drawn towards chalcones (1,3-diarylpropenones) and structurally related compounds, as most of these were shown to have an anti-invasive activity at 1 or 10 μM.

Although certainly promising as a set of lead compounds, no systematic substitution pattern was available in this initial library, since the tested chalcones were all natural products. Therefore, our first aim was to broaden the series of screened chalcones by synthesizing (unnatural) analogues. However, since the binding site(s) of the chalcones remain(s) unrevealed, the design of new compounds based on the topology of the receptor was impossible. As the preparation and biological evaluation of a complete library of chalcones, comprising a wide range of substituents and pharmacophores, would be an enormous task, we envisaged synthesizing a limited number of compounds possessing a strategically chosen substitution pattern. The broadened library could then be used to develop a quantitative structure-activity relationship (QSAR) model, which predicts the anti-invasive activity of hypothetical compounds. On its turn, this in silico screening would enable us to focus future synthetic efforts on promising substances. Such use of QSAR approaches is attractive from an economic as well as an ecological point of view.

As further detailed in the examples that follow herein after, this QSAR approach allowed us to provide a model for the in silico prediction of the anti-invasive activity of chalcone-like compounds. It further allowed us to identify potentially interesting anti-invasive chalcone-like compounds having a predicted anti-invasive activity at a lowest active concentration of ≤0.1 µM and thus being at least 10-100 times more effective in comparison to chalcone-like compounds which are currently under investigation for their use as anti-invasive compounds.

Katritzky et al., 2006 also describes a QSAR model for determining the anti-invasive activity of multiple organic compounds including chalcone-like compounds. However, said model is not suitable for predicting anti-invasive compounds having a lowest active concentration of less than 1 µM, since the lowest active concentration which can be predicted making use of this model is set at 1 µM, as evident from table 1 of this publication and from Bracke et al., 2008.

Yadav et al., 2011 (table 4) provides an overview of multiple chalcone-like compounds and their lowest active concentration rendering "anti-cancer" activity, said concentrations ranging from 1.9 to 50 µM. These compounds are thus at least 20 times less effective compared to the compounds according to this invention.

Furthermore, also Abel Bar et al., 2010 (lowest active concentration 1 µM), Mukherjee et al., 2010 (lowest active concentration 10 µM), Parmar et al., 1997 (lowest active concentration 1 µM), Parmar et al., 1998 (lowest active concentration 1 µM) and Parmar et al., 2003 (lowest active concentration 1 µM) provide chalcone-like compounds which were tested for their anti-invasive activity, however as evident from these documents, none of said compounds have been shown to have anti-invasive activity of less than 1 µM.

In summary, it is generally known that the higher the concentration of a compound needed to obtain a certain effect, the higher the risk for undesired side-effects. Therefore, there was a need for compounds having an anti-invasive activity at the lowest possible concentration, as well as for a model to predict said anti-invasive activity in order to reduce the burden of experimentation. The method and compounds according to this invention provide a solution to said problems. More in particular, the present invention provides chalcone-like compounds having an anti-invasive activity at a concentration of 0.1 µM, or even less. Moreover, these compounds are not toxic and have no negative effect on the survival of the cells. It is a further advantage that these compounds have a broad field of application, i.e. they can be used for the treatment of several types of cancers, more specific cancers characterized by the presence of a malignant solid tumor.

SUMMARY OF THE INVENTION

In a first aspect the present invention provides an in silico method for predicting the anti-invasive activity of a chalcone-like compound according to formula I

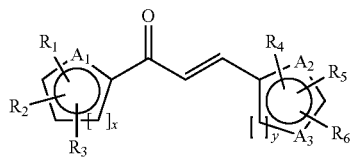

wherein:
$A_1$, $A_2$ and $A_3$ are independently selected from C and O;
$R_1$, $R_2$, $R_3$, $R_4$, $R_5$, and $R_6$ are each independently selected from —H, -halo, —$C_{1-6}$ alkyl, and —O—$C_{1-6}$ alkyl; and
x and y are each independently selected from 1 or 2; and
said method comprising the steps of:
for said compound determining the theoretical molecular descriptors:
maximal antibonding contribution of one molecular orbital ($D_1$),
partial surface area for atom C ($D_2$),
final heat of formation/# atoms ($D_3$),
XY Shadow/XY Rectangle ($D_4$),
minimum 1-electron reacting index for atom O ($D_5$), and
polarity parameter ($D_6$); and
for said compound determining log $c_{min}$ making use of:

$$\log c_{min} = 58.90 + (28.63 \times D_1) - (16.29 \times D_2) + (1.093 \times D_3) + (9.904 \times D_4) - (116.3 \times D_5) + (17.01 \times D_6)$$

wherein:
when log $c_{min}$ is ≥2.5, said compound is predicted to have anti-invasive activity at a lowest active concentration of >100 µM
when log $c_{min}$ is ≥1.5 and <2.5, said compound is predicted to have anti-invasive activity at a lowest active concentration of about 100 µM
when log $c_{min}$ is ≥0.5 and <1.5, said compound is predicted to have anti-invasive activity at a lowest active concentration of about 10 µM
when log $c_{min}$ is >−0.5 and <0.5, said compound is predicted to have anti-invasive activity at a lowest active concentration of about 1 µM
when log $c_{min}$ is >−1.5 and ≤−0.5, said compound is predicted to have anti-invasive activity at a lowest active concentration of about 0.1 µM
when log $c_{min}$ is >−2.5 and ≤−1.5, said compound is predicted to have anti-invasive activity at a lowest active concentration of about 0.01 µM
when log $c_{min}$ is ≤−2.5, said compound is predicted to have anti-invasive activity at a lowest active concentration of <0.01 µM.
Thus,

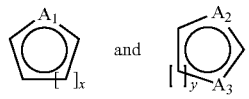

independently from each other represent a 5- or 6-membered aryl or O-containing heteroaryl moiety.
In particular, when $A_2$ and $A_3$ are both O, then y equals 2, or R6 is absent.
More in particular, the invention provides a method for predicting if a compound according to formula I as defined herein has an anti-invasive activity at a lowest active concentration of about 0.1 µM, said method comprising the steps of:

for said compound determining the theoretical molecular descriptors:
maximal antibonding contribution of one molecular orbital ($D_1$),
partial surface area for atom C ($D_2$),
final heat of formation/# atoms ($D_3$),
XY Shadow/XY Rectangle ($D_4$),
minimum 1-electron reacting index for atom O ($D_5$), and
polarity parameter ($D_6$); and
for said compound determining log $c_{min}$ making use of:

$$\log c_{min} = 58.90 + (28.63 \times D_1) - (16.29 \times D_2) + (1.093 \times D_3) + (9.904 \times D_4) - (116.3 \times D_5) + (17.01 \times D_6)$$

wherein:
when log $c_{min}$ is $>-1.5$ and $\leq -0.5$, said compound is predicted to have anti-invasive activity at a lowest active concentration of about 0.1 µM
when log $c_{min}$ is $>-2.5$ and $\leq -1.5$, said compound is predicted to have anti-invasive activity at a lowest active concentration of about 0.01 µM
when log $c_{min}$ is $\leq -2.5$, said compound is predicted to have anti-invasive activity at a lowest active concentration of <0.01 µM.

In a further aspect the present invention provides a compound according to formula I
wherein:
$A_1$, $A_2$ and $A_3$ are independently selected from C and O;
$R_1$, $R_2$, $R_3$, $R_4$, $R_5$, and $R_6$ are each independently selected from —H, -halo, —$C_{1-6}$ alkyl, and —O—$C_{1-6}$ alkyl; and
x and y are each independently selected from 1 or 2; and
having a predicted lowest active concentration of 0.1 µM or less, when making use of the herein described method; for use as an anti-invasive compound.

This invention also provides a compound of Formula I or a stereoisomer, tautomer, racemic, metabolite, pro- or predrug, salt, hydrate, or solvate thereof, wherein:
$A_1$, $A_2$ and $A_3$ are independently selected from C and O;
$R_1$, $R_2$, $R_3$, $R_4$, $R_5$, and $R_6$ are each independently selected from —H, -halo, —$C_{1-6}$ alkyl, and —O—$C_{1-6}$ alkyl; and
x and y are independently selected from 1 or 2, and wherein at least one of x and y is 1;
and having a predicted lowest active concentration of 0.1 µM or less, when making use of the herein described method; for use as an anti-invasive compound.

In a further embodiment, this invention provides a compound of Formula I or a stereoisomer, tautomer, racemic, metabolite, pro- or predrug, salt, hydrate, or solvate thereof, wherein:
$A_1$ is C, one of $A_2$ and $A_3$ is C and the other one of $A_2$ and $A_3$ is O;
$R_1$, $R_2$, and $R_3$ are each independently selected from —H, -halo, and —O—$C_{1-6}$ alkyl;
$R_4$, $R_5$, and $R_6$ are each —H;
x is 2; and
y is 1;
and having a predicted lowest active concentration of 0.1 µM or less, when making use of the herein described method; for use as an anti-invasive compound.

In yet a further embodiment this invention provides a compound of Formula Ia or a stereoisomer, tautomer, racemic, metabolite, pro- or predrug, salt, hydrate, or solvate thereof,

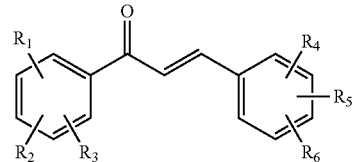

Ia wherein:
$R_1$, $R_2$, $R_3$, $R_4$, $R_5$, and $R_6$ are each independently selected from —H, -halo, —$C_{1-6}$ alkyl, and —O—$C_{1-6}$ alkyl;
and having a predicted lowest active concentration of 0.1 µM or less, when making use of the herein described method; for use as an anti-invasive compound.

In an even further embodiment, this invention provides a compound of Formula Ia or a stereoisomer, tautomer, racemic, metabolite, pro- or predrug, salt, hydrate, or solvate thereof, wherein:
$R_1$, $R_2$, and $R_3$, are each independently selected from —H, -halo, and —O—$C_{1-6}$ alkyl;
$R_4$, and $R_5$ are each —H; and
$R_6$ is -halo
and having a predicted lowest active concentration of 0.1 µM or less, when making use of the herein described method; for use as an anti-invasive compound.

This invention also provides a compound of Formula Ib or a stereoisomer, tautomer, racemic, metabolite, pro- or predrug, salt, hydrate, or solvate thereof,

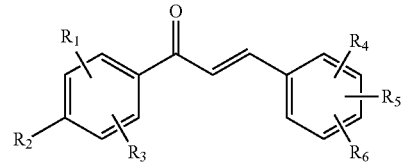

Ib wherein:
$R_1$, $R_3$, $R_4$, $R_5$, and $R_6$ are each independently selected from —H, -halo, and —O—$C_{1-6}$ alkyl; and
$R_2$ is selected from -halo, and —O—$C_{1-6}$ alkyl;
and having a predicted lowest active concentration of 0.1 µM or less, when making use of the herein described method; for use as an anti-invasive compound.

In a further embodiment, this invention provides a compound of Formula Ic or a stereoisomer, tautomer, racemic, metabolite, pro- or predrug, salt, hydrate, or solvate thereof,

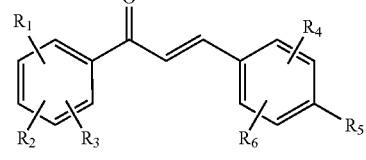

Ic wherein:
$R_1$, $R_2$, $R_3$, $R_4$, and $R_6$ are each independently selected from —H, -halo, and —O—$C_{1-6}$ alkyl; and
$R_5$ is selected from -halo, and —O—$C_{1-6}$ alkyl;
and having a predicted lowest active concentration of 0.1 µM or less, when making use of the herein described method; for use as an anti-invasive compound.

In a further embodiment, this invention provides a compound of Formula Id or a stereoisomer, tautomer, racemic, metabolite, pro- or predrug, salt, hydrate, or solvate thereof,

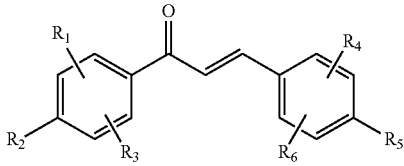

wherein:
$R_1$, $R_3$, $R_4$, and $R_6$ are each independently selected from —H, -halo, and —O—$C_{1-6}$ alkyl; and
$R_2$ and $R_5$ are each independently selected from -halo, and —O—$C_{1-6}$ alkyl;
and having a predicted lowest active concentration of 0.1 μM or less, when making use of the herein described method; for use as an anti-invasive compound.

In a further aspect the present invention provides a compound of Formula II or a stereoisomer, tautomer, racemic, metabolite, pro- or predrug, salt, hydrate, or solvate thereof,

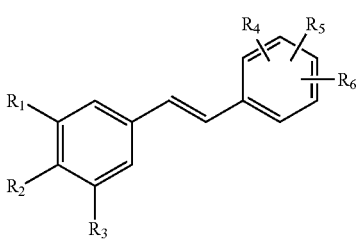

wherein:
$R_1$, $R_2$, $R_3$, $R_4$, $R_5$, and $R_6$ are each independently selected from —H, -halo, —$C_{1-6}$ alkyl, and —O—$C_{1-6}$ alkyl; wherein at least one of $R_1$, $R_2$ and $R_3$ is not —H;
for use as an anti-invasive compound.

In a further embodiment, this invention provides a compound of Formula II or a stereoisomer, tautomer, racemic, metabolite, pro- or predrug, salt, hydrate, or solvate thereof, wherein:
$R_1$, $R_2$ and $R_3$ are each —O—$C_{1-6}$ alkyl; and
$R_4$, $R_5$, and $R_6$ are each independently selected from —H, -halo, —$C_{1-6}$ alkyl, and —O—$C_{1-6}$ alkyl for use as an anti-invasive compound.

In yet a further embodiment, this invention provides a compound of Formula IIa or a stereoisomer, tautomer, racemic, metabolite, pro- or predrug, salt, hydrate, or solvate thereof,

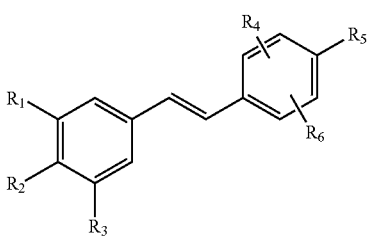

wherein:
$R_1$, $R_2$, and $R_3$ are each independently selected from —H, -halo, —$C_{1-6}$ alkyl, and —O—$C_{1-6}$ alkyl;
wherein at least one of $R_1$, $R_2$ and $R_3$ is not —H;

$R_4$ and $R_6$ are each independently selected from —H, -halo, —$C_{1-6}$ alkyl, and —O—$C_{1-6}$ alkyl;
$R_5$ is selected from -halo, —$C_{1-6}$ alkyl, and —O—$C_{1-6}$ alkyl;
for use as an anti-invasive compound.

In a further embodiment, this invention provides a compound according to formula II or IIa; wherein the double bond in the linker between the aryl or heteroaryl moieties has the Z configuration; for use as an anti-invasive compound.

In a particular embodiment, this invention provides a compound according to formula II or IIa, said compound being selected from the list consisting of:
1,1-(E)-ethene-1,2-diylbis(4-fluorobenzene);
1-fluoro-4-[(E)-2-(4-methoxyphenyl)ethenyl]benzene;
1-fluoro-4-[(Z)-2-phenylethenyl]benzene;
1,2,3-trimethoxy-5-[(Z)-2-phenylethenyl]benzene;
5-[(Z)-2-(4-fluorophenyl)ethenyl]-1,2,3-trimethoxybenzene;
1,1'-(E)-ethene-1,2-diyldibenzene; and
1,2,3-trimethoxy-5-[(E)-2-phenylethenyl]benzene.

In another particular embodiment, this invention provides a compound according to formula I, Ia, Ib, Ic, Id or Ie, said compound being selected from the list consisting of:
(2E)-3-(4-fluorophenyl)-1-(3,4,5-trimethoxyphenyl)prop-2-en-1-one;
(2E)-3-(4-chlorophenyl)-1-(4-methoxyphenyl)prop-2-en-1-one;
(2E)-1-(4-methoxyphenyl)-3-(2,4,6-trimethoxyphenyl)prop-2-en-1-one;
(2E)-3-(3-fluorophenyl)-1-(4-fluorophenyl)prop-2-en-1-one;
(2E)-3-(furan-2-yl)-1-(3,4,5-trimethoxyphenyl)prop-2-en-1-one;
(2E)-1-(2,6-dimethoxyphenyl)-3-(furan-2-yl)prop-2-en-1-one;
(2E)-1-(4-fluorophenyl)-3-(furan-3-yl)prop-2-en-1-one; and
(2E)-1,3-di(furan-2-yl)prop-2-en-1-one.

More specific, the invention provides said compound for use as an anti-invasive compound.

In a further aspect the present invention provides a pharmaceutical composition for use as an anti-invasive composition; said composition comprising a compound according to this invention.

In yet a further aspect this invention provides a method for inhibiting the invasiveness of tumor cells; said method comprising contacting said cells with a pharmaceutically effective amount of a compound or a composition according to this invention.

In a further aspect this invention provides a method for inhibiting invasion of tumor cells into the adjacent tissue in a subject having a condition associated with undesired cell migration; said method comprising administering to said subject a therapeutically effective amount of a compound or a composition according to this invention. Said condition in particular being associated with solid malignant tumors; more in particular selected from the list comprising mammary tumors, prostate tumors, colorectal tumors, lung tumors, brain tumors, head and neck tumors, melanoma, sarcoma, or ovarian tumors.

DETAILED DESCRIPTION OF THE DRAWINGS

Figure 2:
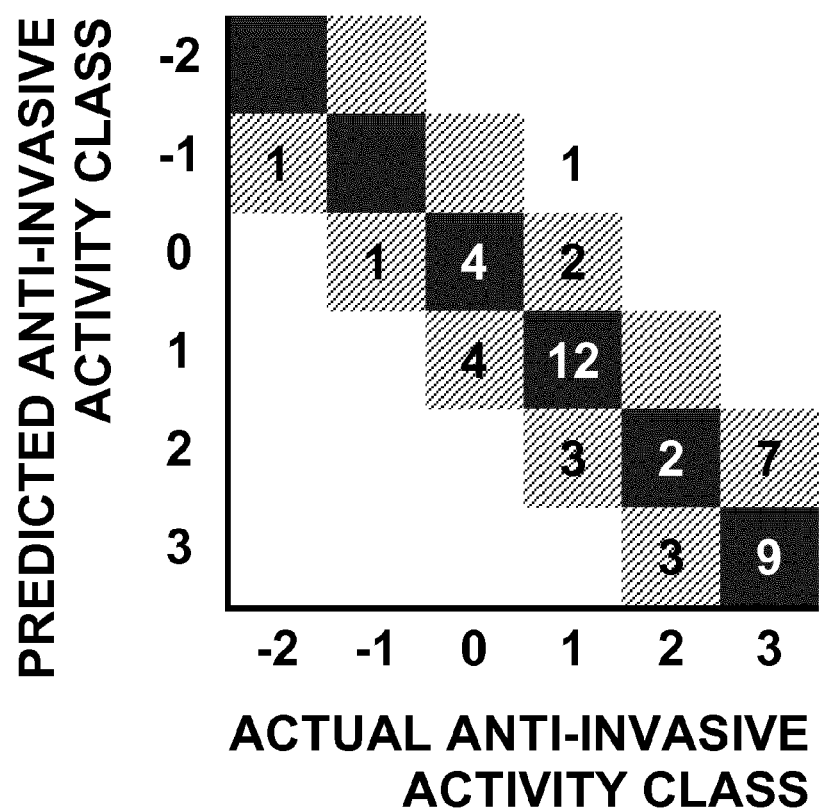
Figure 3:
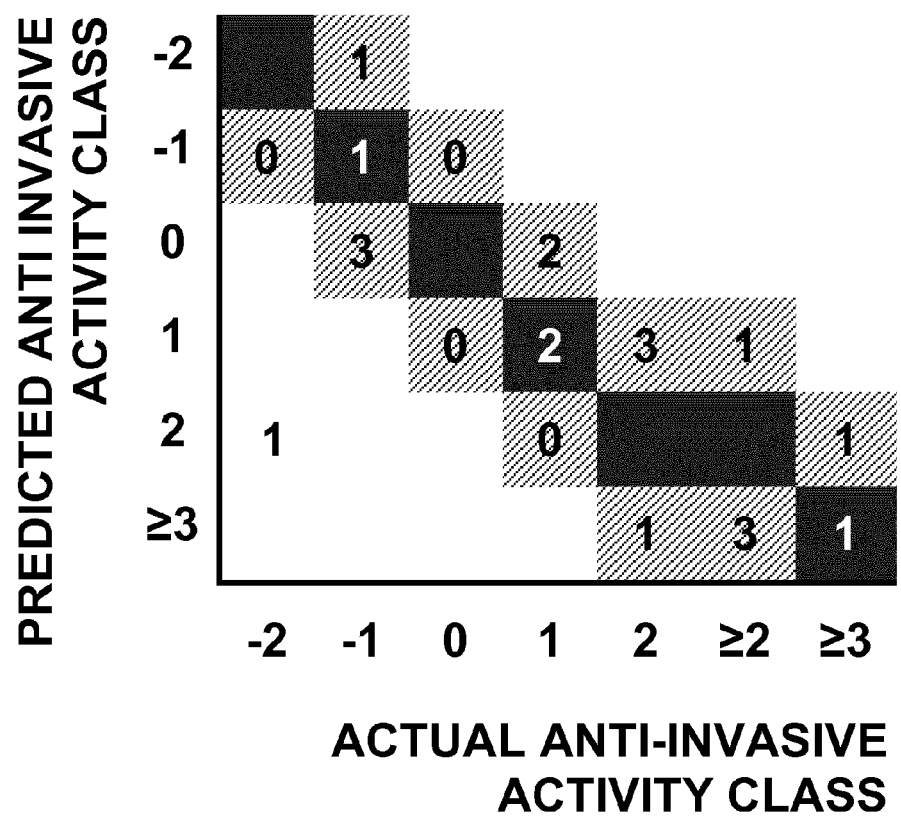

FIG. 1. Determination of the 'break point' using $\Delta r^2 < 0.05$ as a cut-off criterion.
FIG. 2. Confusion matrix of the training set.
FIG. 3. Confusion matrix of the test set.

Figure 4:
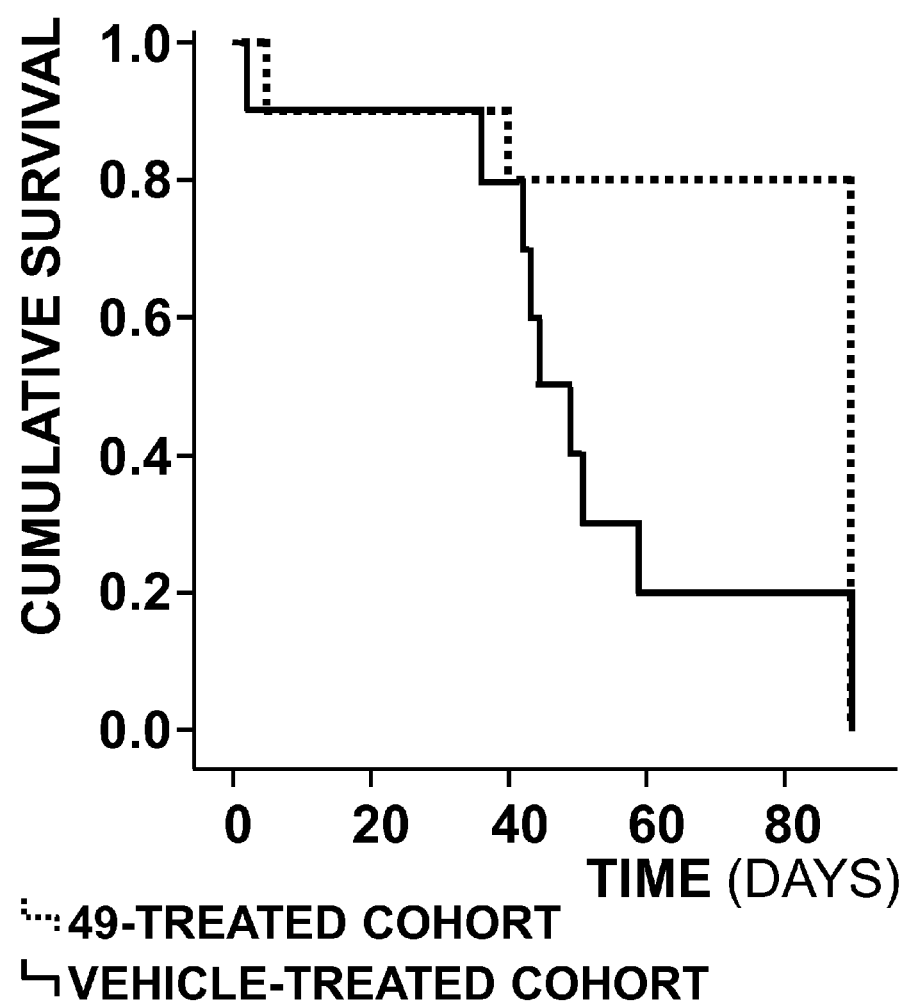

FIG. 4. Kaplan-Meier survival curve obtained during the initial in vivo potency assessment.

Figure 5:
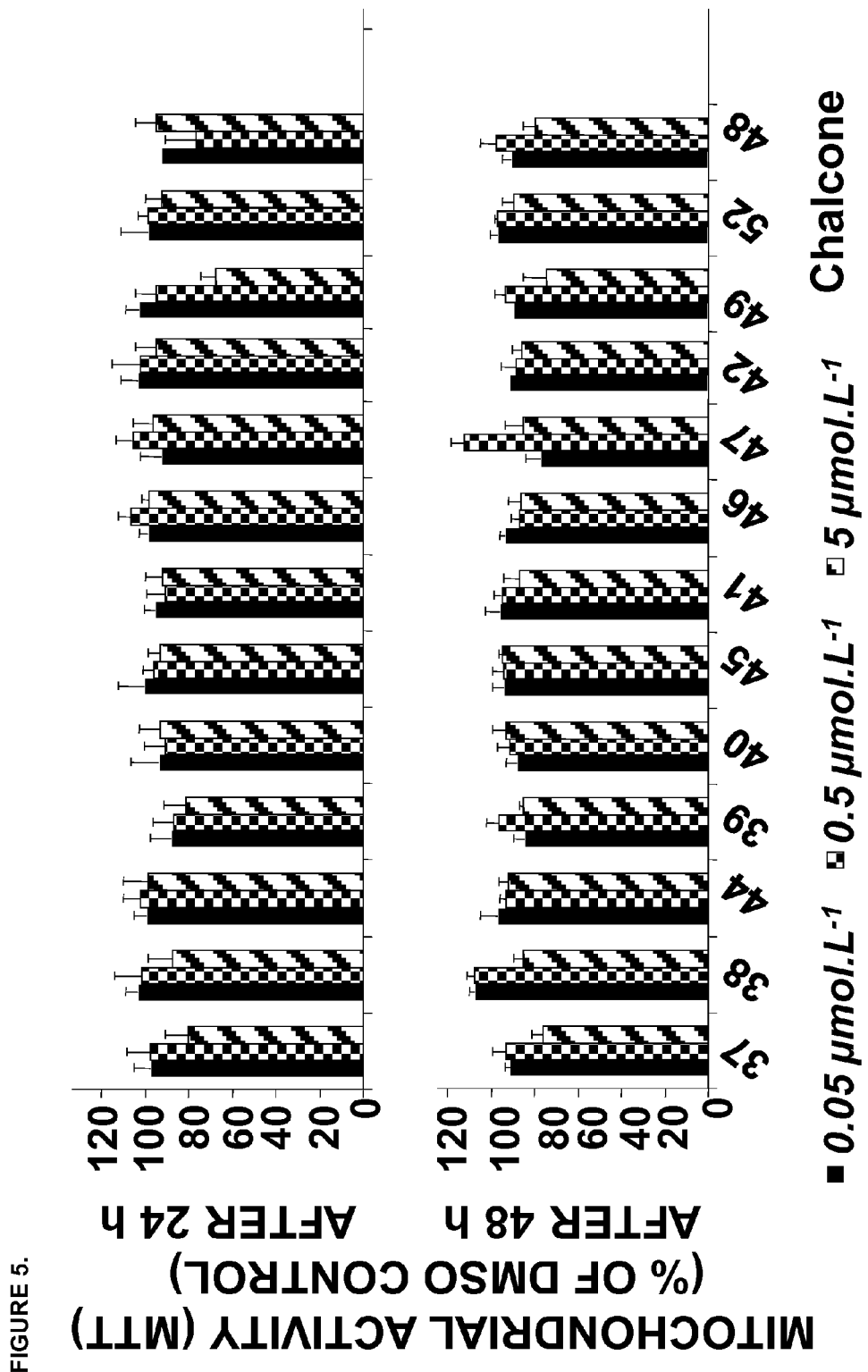

FIG. 5. Assessment of the antiproliferative effects of chalcone-like compounds on MCF-7/6 cells in the MTT assay. Determination of mitochondrial activity after 24 and 48 h in the presence of 0.05, 0.5 or 5 µmol·L$^{-1}$ of a compound, relative to the solvent control (average±SD).

Figure 6:
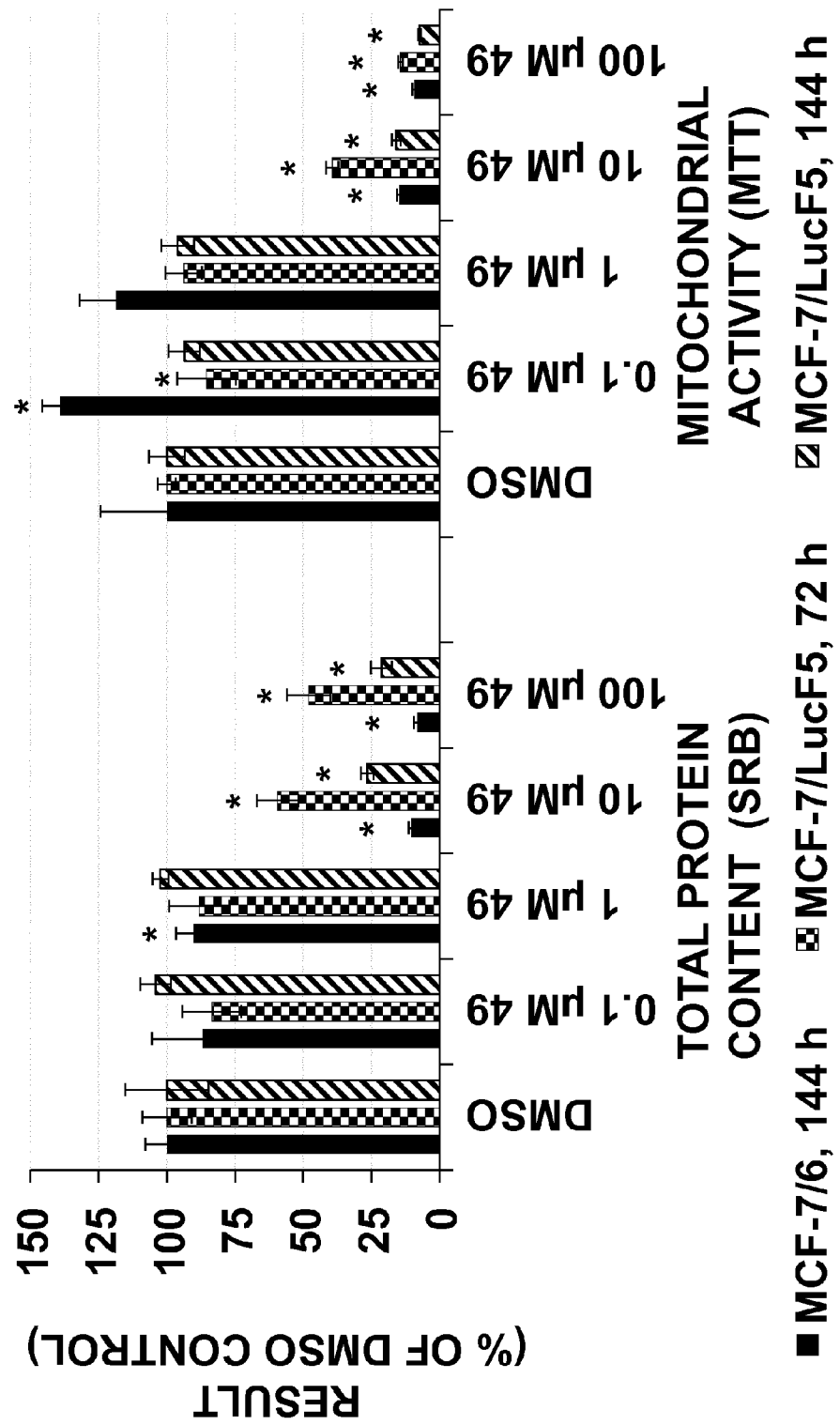

FIG. 6. Assessment of the antiproliferative effects of compound 49 on MCF-7/6 and MCF-7/LucF5 cells in the SRB and MTT assays. Determination of total protein content and mitochondrial activity after 72 and 144 h in the presence of 0.1, 1, 10 or 100 µmol·L$^{-1}$ of compound 49, relative to the solvent control (average±SD, *p<0.05).

Figure 7:
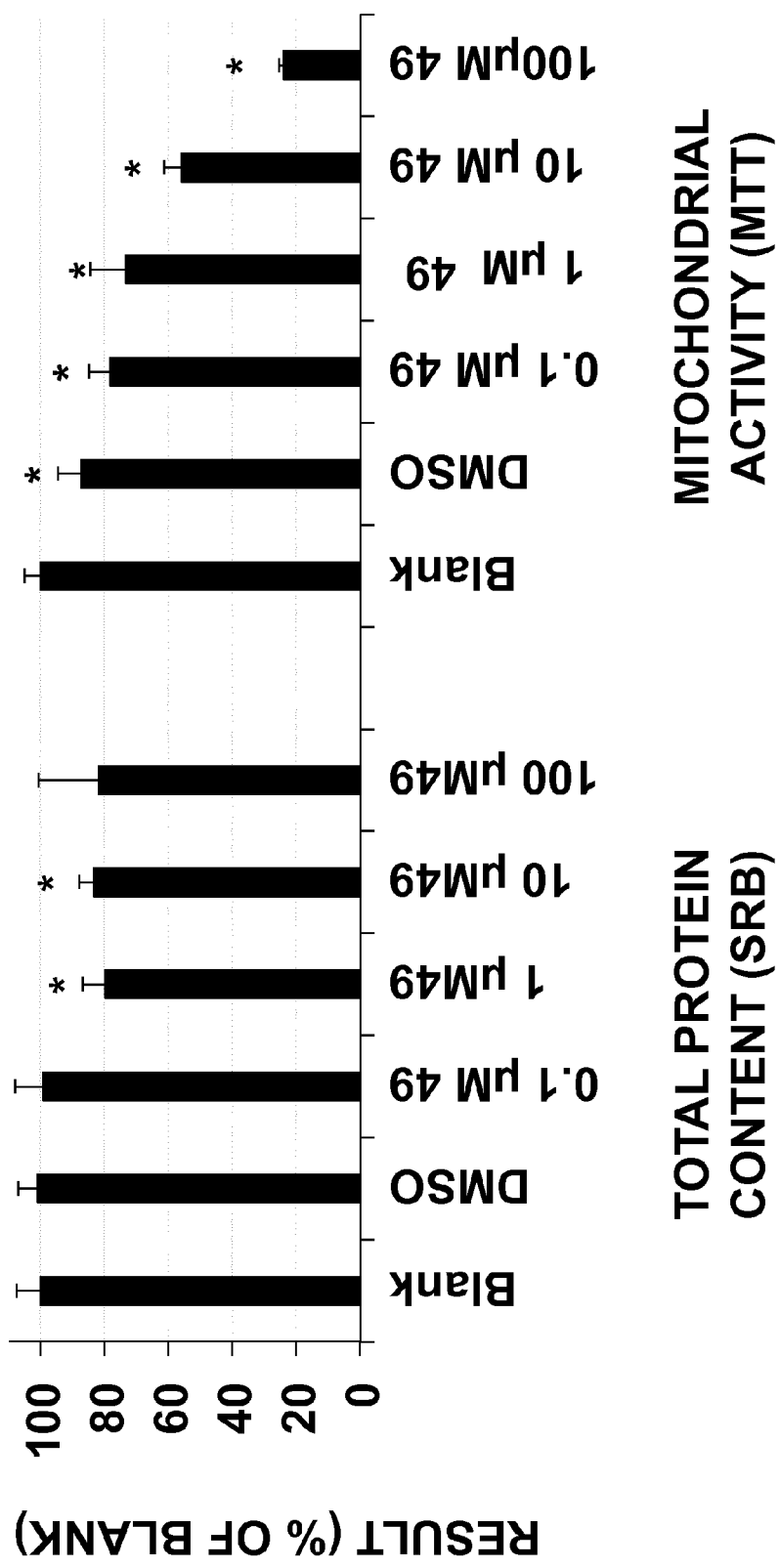

FIG. 7. Antiproliferative effects of compound 49 on BLM melanoma cells. Determination of total protein content and mitochondrial activity after 24 h in the presence of solvent and 0.1, 1, 10 or 100 µmol·L$^{-1}$ of chalcone 49, relative to the blank (average±SD, *p<0.05).

Figure 8:
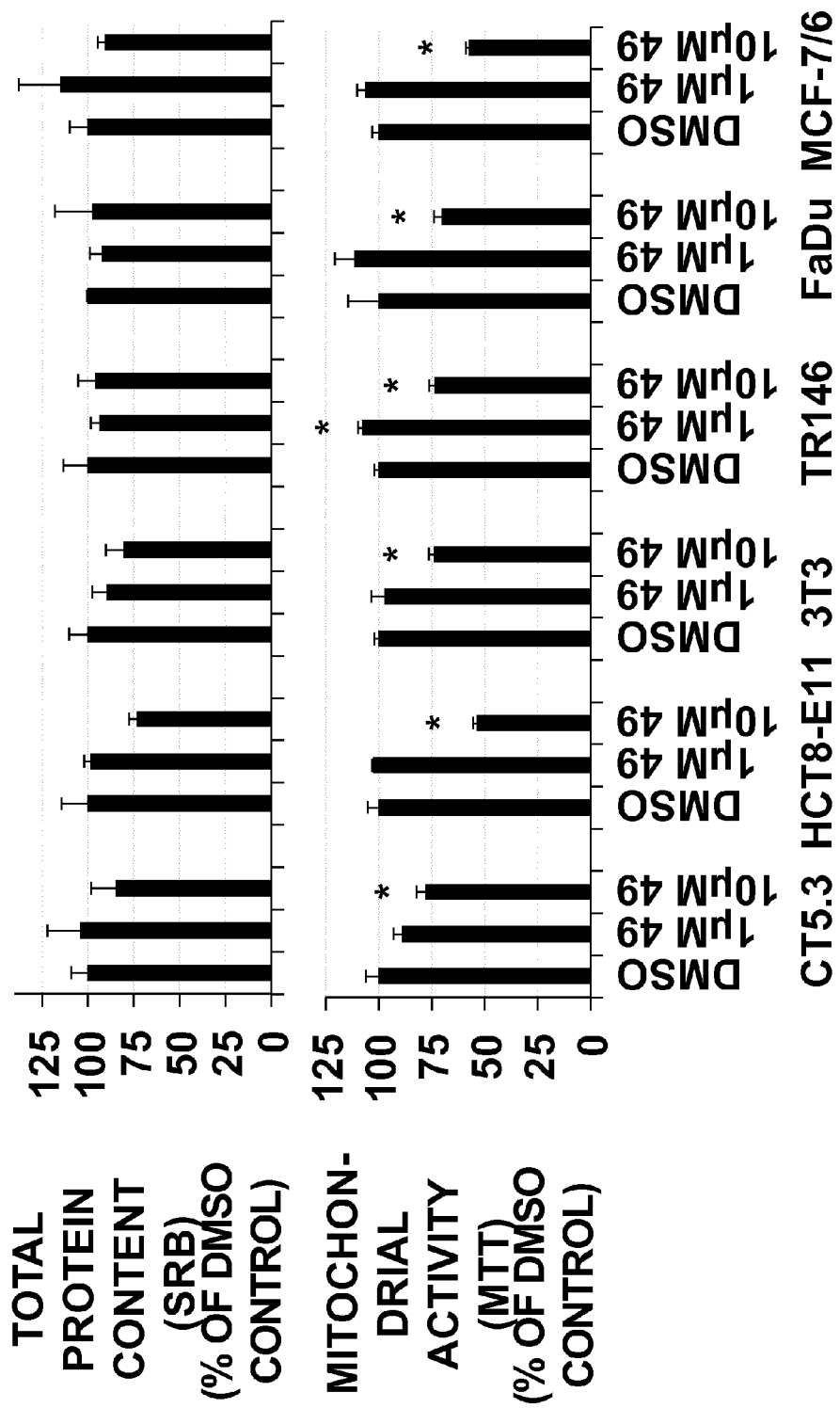

FIG. 8. Cell specificity of the antiproliferative effects of compound 49, relative to solvent control (average±SD, *p<0.05). Above: SRB assay after 24 h of incubation for six cell lines. Below: MTT assay after 24 h of incubation for six cell lines.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

As already mentioned hereinbefore, in a first aspect the present invention provides a method for predicting the anti-invasive activity of a compound according to formula I

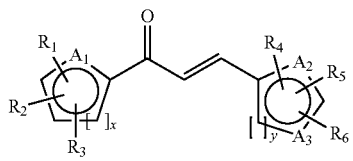

I wherein:
  $A_2$ and $A_3$ are independently selected from a C atom and an O atom;
  $R_1$, $R_2$, $R_3$, $R_4$, $R_5$, and $R_6$ are each independently selected from —H, -halo, —$C_{1-6}$ alkyl, and —O—$C_{1-6}$ alkyl; and
  x and y are each independently selected from 1 or 2; and
said method comprising the steps of:
  for said compound determining the theoretical molecular descriptors:
    maximal antibonding contribution of one molecular orbital ($D_1$),
    partial surface area for atom C ($D_2$),
    final heat of formation/# atoms ($D_3$),
    XY Shadow/XY Rectangle ($D_4$),
    minimum 1-electron reacting index for atom O ($D_5$), and
    polarity parameter ($D_6$); and
  for said compound determining log $c_{min}$ making use of:

$$\log c_{min} = 58.90 + (28.63 \times D_1) - (16.29 \times D_2) + (1.093 \times D_3) + (9.904 \times D_4) - (116.3 \times D_5) + (17.01 \times D_6)$$

wherein:
  when log $c_{min}$ is ≥2.5, said compound is predicted to have anti-invasive activity at a lowest active concentration of >100 µM
  when log $c_{min}$ is ≥1.5 and <2.5, said compound is predicted to have anti-invasive activity at a lowest active concentration of about 100 µM
  when log $c_{min}$ is ≥0.5 and <1.5, said compound is predicted to have anti-invasive activity at a lowest active concentration of about 10 µM
  when log $c_{min}$ is >−0.5 and <0.5, said compound is predicted to have anti-invasive activity at a lowest active concentration of about 1 µM
  when log $c_{min}$ is >−1.5 and ≤−0.5, said compound is predicted to have anti-invasive activity at a lowest active concentration of about 0.1 µM
  when log $c_{min}$ is >−2.5 and ≤−1.5, said compound is predicted to have anti-invasive activity at a lowest active concentration of about 0.01 µM
  when log $c_{min}$ is ≤−2.5, said compound is predicted to have anti-invasive activity at a lowest active concentration of <0.01 µM.

Thus,

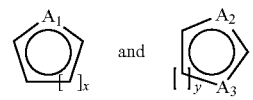

independently from each other represent a 5- or 6-membered aryl or O-containing heteroaryl moiety.

In particular, when $A_2$ and $A_3$ are both O, then y equals 2, or R6 is absent.

In other words, the compound according to formula I, can also be represented as follows:

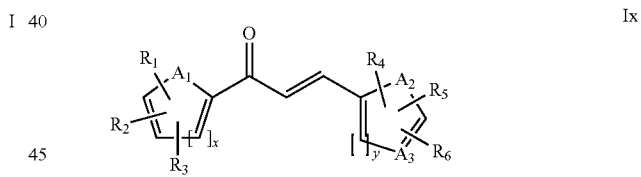

Ix wherein:
  $A_1$, $A_2$ and $A_3$ are independently selected from —C— and —O—;
  $R_1$, $R_2$, $R_3$, $R_4$, $R_5$, and $R_6$ are each independently selected from —H, -halo, —$C_{1-6}$ alkyl, and —O—$C_{1-6}$ alkyl; and
  x and y are each independently selected from 1 or 2.

In particular, the present invention discloses for the first time an in silico method to predict if a compound of the invention has an anti-invasive activity at a lowest active concentration of 0.1 µM or less, wherein said method comprises the steps of:
  for said compound determining the theoretical molecular descriptors:
    maximal antibonding contribution of one molecular orbital ($D_1$),
    partial surface area for atom C ($D_2$),
    final heat of formation/# atoms ($D_3$),
    XY Shadow/XY Rectangle ($D_4$),
    minimum 1-electron reacting index for atom O ($D_5$), and
    polarity parameter ($D_6$); and for said compound determining log $c_{min}$ making use of:

$$\log c_{min} = 58.90 + (28.63 \times D_1) - (16.29 \times D_2) + (1.093 \times D_3) + (9.904 \times D_4) - (116.3 \times D_5) + (17.01 \times D_6)$$

wherein:
- when log $c_{min}$ is >−1.5 and ≤−0.5, said compound is predicted to have anti-invasive activity at a lowest active concentration of about 0.1 μM
- when log $c_{min}$ is >−2.5 and ≤−1.5, said compound is predicted to have anti-invasive activity at a lowest active concentration of about 0.01 μM
- when log $c_{min}$ is ≤−2.5, said compound is predicted to have anti-invasive activity at a lowest active concentration of <0.01 μM.

When describing the compounds of the invention, the terms used are to be construed in accordance with the following definitions, unless a context dictates otherwise.

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

In a particular embodiment, and in accordance with the methods and compounds disclosed herein, —$C_{1-6}$ alkyl is meant to be —$CH_3$ and —O—$C_{1-6}$ alkyl is meant to be —O—$CH_3$.

As used herein, the term "-halo" refers to halogen; said halogen in a particular embodiment being —F (-fluor).

It will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I or II and any subgroup thereof. This term also refers to the compounds as depicted in the tables disclosed hereinafter, their derivatives, N-oxides, salts, solvates, hydrates, stereoisomeric forms, racemic mixtures, tautomeric forms, optical isomers, analogues, prodrugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

"Log $c_{min}$" refers to the decadic logarithm of the lowest active concentration ($c_{min}$) of a compound expressed in units of μmol/l, and is a measure to determine its anti-invasive activity class, as represented in table 1.

As used herein the term "$c_{min}$" is meant to be the lowest active concentration of a compound, i.e. the lowest concentration at which a substance exhibits an anti-invasive behavior. "Anti-invasive" or "anti-invasive activity" is the ability to inhibit the invasiveness of tumor cells. Invasion by tumor cells is defined as the progressive occupation and destruction of their environment, and is the result of matrix degradation and directional cell motility. Anti-invasive activity of a compound is the ability to inhibit or block invasion, and can be assessed by counting the number of invading cells, by the depth of their invasion and/or by the amount of environmental destruction. Many assays in vitro can be applied to test for anti-invasive activity (for a complete list see Bracke et al. 2008). The three most popular ones are:

- Chick heart invasion assay (Bracke et al., 2001, see details below). The cut-off value is between grade II (non-invasive) and grade III (invasive). Anti-invasive activity is considered to shift the readout from grade III or IV (solvent-treated) to grade 0, grade I or grade II (compound-treated)
- Collagen type I invasion assay. Collagen gels, prepared on the bottom of plastic wells are covered with a test cell suspension, and incubated with liquid culture medium for 24 h. Invasion is evaluated with an inverted phase-contrast microscope, and is based on the percentage of cells showing extensions in the gel. Anti-invasive activity is considered if this percentage attributed to solvent-treated cells is significantly lower for the compound-treated cells.
- Matrigel invasion assay. Matrigel is a mixture of basement membrane components, and is applied as a semi-solid layer on top a filter with pores allowing the transgression of cells. The test cell suspension is seeded on top of the gel, and incubated for 1 day in a two-compartment chamber system. Invasion is then evaluated via the percentage of cells that are attached to the lower side of the filter. Anti-invasive activity is considered if this percentage attributed to solvent-treated cells is significantly lower for the compound-treated cells.

In the chick heart invasion assay cancer cells are confronted with a fragment of normal tissue, so as not to neglect the contribution of the host tissue in the micro-ecosystem that governs tumor behavior. As such, precultured heart tissue fragments (PHFs), dissected from 9-day-old chicken embryos, may be confronted with aggregates of human invasive MCF-7/6 mammary carcinoma cells in the presence of a certain concentration of a test compound. After eight days, the interaction between the cancer cells and the PHF is evaluated histologically and classified along a 5-grades subjective scale (Bracke et al., 2001). Grades III and IV are typical for invasion, while grades 0, I and II correspond to absence of invasion. Compounds that inhibit invasion of confronting cancer cells i.e. from III/IV to 0/I/II, are determined as anti-invasive. Possible alternative assays generally known in the art are the type I collagen invasion assay, wound healing assay and the matrigel invasion assay. As such, six activity levels were defined, ranging from class −2 for the most active compounds (invasion grade I or II at the 0.01 μmol/l level) to class 3 (compounds with no apparent effect at a concentration of 100 μmol/ (see table 1).

TABLE 1

Definition of the six anti-invasive activity classes according to '$c_{min}$': the lowest concentration at which an in vitro anti invasive activity (invasion grade I or II) is exhibited

| $c_{min}$ (μM) | Log $c_{min}$ | Class |
|---|---|---|
| >100 | ≥2.5 | 3 |
| about 100 | ≥1.5 and <2.5 | 2 |
| about 10 | ≥0.5 and <1.5 | 1 |
| about 1 | >−0.5 and <0.5 | 0 |
| about 0.1 | >−1.5 and ≤−0.5 | −1 |
| about 0.01 | >−2.5 and ≤−1.5 | −2 |

As used herein, the term "at a concentration of about 0.1 μM or less" includes 0.1 μM, 0.05 μM, 0.01 μM, 0.005 μM, 0.001 μM and less; and all values in between.

As used herein, the term "at a concentration of about 0.01 μM or less" includes 0.01 μM, 0.005 μM, 0.001 μM, 0.0005 μM and less; and all values in between.

As used herein, the term "molecular descriptor" is meant to be the final result of a logic and mathematical procedure which transforms chemical information encoded within the structure of a molecule into a useful number, i.e. the theoretical molecular descriptor. A person skilled in the art is well aware of these terms and their meaning and by making use of the required software package is able to determine a given theoretical descriptor for a given compound. For example, a 2D drawing of a compound can be loaded into a computational chemistry software package, such as for example HyperChem, thereby obtaining its refined equilibrium molecular geometry by:

(i) 2D to 3D conversion using parameters included in said software package,
(ii) pre-optimization using the molecular mechanics force field (MM+) method and
(iii) final optimization at the semi-empirical AM1-level of theory using a Polak-Ribiere conjugated gradient and an RMS gradient of 0.01 kcal/(Å·mol) as the termination condition for optimized structures.

These geometries are then loaded into a software package that combines diverse statistical structure-property-activity correlation techniques, and that allows the determination of the theoretical descriptors as defined; such as for example CODESSA Pro. All defined descriptors are derived solely from the molecular structure and their computation therefore requires no experimental data.

The model described herein provides the use of 6 descriptors as defined in table 2.

TABLE 2

Descriptors $D_i$ of the optimal model and their statistical parameters

| i | Name of descriptor $D_i$ | t-stat | p-value* | IC |
|---|---|---|---|---|
| 0 | Intercept | 4.944 | 0.0000 | |
| 1 | Max antibonding contribution of one MO | 5.349 | 0.0000 | 0.1829 |
| 2 | Partial Surface Area for atom C | −5.608 | 0.0000 | 0.5732 |
| 3 | Final heat of formation/# atoms | 7.537 | 0.0000 | 0.5959 |
| 4 | XY Shadow/XY Rectangle | 5.147 | 0.0000 | 0.2933 |
| 5 | Min 1-electron react. index for atom O | −2.608 | 0.0126 | 0.2122 |
| 6 | Polarity parameter (Zefirov) | 3.212 | 0.0025 | 0.3633 |

*t-test, $v_1 = n - p - 1 = 42$;
IC: partial intercorrelation.

As used in the model according to this invention, the first descriptor, 'Maximum antibonding contribution of one MO' ($D_1$), is a quantum chemical descriptor that is related to the stability of a molecule, given that a larger antibonding contribution will result in a higher energy molecular orbital. The coefficient of $D_1$ has a positive sign, which suggests that lower energetic molecules will exhibit a stronger anti-invasive potency. Moreover, a higher score for this descriptor type has been associated with an increased aqueous solubility. In the present study, this would signify that more lipophilic compounds will possess stronger anti-invasive properties.

Descriptor $D_2$, 'Partial Surface Area for atom C', together with its negative coefficient, highlights the importance of hydrocarbon moieties in the molecule and may point towards an important Van der Waals contribution to the host-guest interaction, i.e. the presence of an important lipophilic binding site in the binding pocket.

The most significant descriptor of the model, according to the t-statistic, is $D_3$: 'Final heat of formation/# atoms'. The coefficient of this quantum chemical descriptor carries a positive sign. Consequently, for thermodynamically more stable compounds, which possess a negative energy of formation, the contribution of this descriptor will result in a lower overall score and thus a higher anti-invasive activity. This observation is consonant with the information extracted from descriptor $D_1$.

'XY Shadow/XY Rectangle', $D_4$, is a molecular shadow indices, defined as the projection of the molecules Van der Waals envelope on the XY plane, where X and Y are the shortest and second shortest inertial axes of the molecule, respectively. The shadow area is usually determined through application of a two dimensional square grid on the molecular projection and subsequent summation of the areas of squares overlapped with the projection. This descriptor is directly connected to the molecular size and consequently also stresses the van der Waals contribution to the binding at the molecular target. Furthermore, it may furnish information about the correct orientation of the chalcone towards its target. Since the coefficient for this descriptor bears a positive sign, molecules with smaller projected dimensions in the XY plane will have a higher desired activity. This may very likely be due to a better fit of molecules with a smaller projected XY envelope in the binding pocket.

Descriptor $D_5$ is the 'minimum 1-electron reaction index for an oxygen atom', calculated as $$D_5 = \sum_{i \in A} \sum_{i \in A} \frac{c_{iHOMO} c_{jLUMO}}{\varepsilon_{LUMO} - \varepsilon_{HOMO}},$$

in which summations are performed over all atomic orbitals i, j of the given atom, $c_{iHOMO}$ and $c_{jLUMO}$ are the i-th and j-th atomic orbital coefficients on the HOMO and LUMO, respectively, and $\varepsilon_{LUMO}$ and $\varepsilon_{HOMO}$ represent the energies of the latter orbitals. This descriptor probably highlights an important interaction between the carbonyl oxygen and the receptor binding site.

The sixth descriptor $D_6$ in our QSAR-equation is the 'Polarity parameter', which is defined as $$D_6 = q_{max} - q_{min},$$

i.e. the difference between the most positive and most negative partial charges in the molecule. In this calculation, the charge distribution in the molecule is determined based on Zefirov's approach, which uses the Sanderson electronegativity scale and represents the molecular electronegativity as the geometric mean of the atomic electronegativities. The positive coefficient for this descriptor indicates that less polar, more lipophilic tend to exhibit a better anti-invasive potency. This again agrees with the analysis made for descriptor $D_1$ and $D_2$.

As already defined herein, the optimal model for determining the anti-invasive activity for compounds according to this invention is:

$$\log c_{min} = 58.90 + (28\,0.63 \times D_1) - (16.29 \times D_2) + (1.093 \times D_3) + (9.904 \times D_4) - (116.3 \times D_5) + (17.01 \times D_6)$$

wherein, $D_1$-$D_6$ represent the theoretical descriptors as defined herein above.

In order to provide an indication of the accuracy, standard errors of the weighting factors are as follows:

$$\log c_{min} = -(58.90 \pm 11.91) + (28.63 \pm 5.352) \times D_1 - (16.29 \pm 2.905) \times D_2 + (1.093 \pm 0.145) \times D_3 + (9.904 \pm 1.924) \times D_4 - (116.3 \pm 44.61) \times D_5 + (17.01 \pm 5.296) \times D_6$$

As evident for a person skilled in the art, the method as defined herein above, is not only suitable for prediction of the anti-invasive activity of a compound according to formula I, but also for predicting the anti-invasive activity of a compound according to any subgroup thereof as defined herein below, in particular compounds according to formula Ia, Ib, Ic, Id and Ie.

This invention further provides a compound according to formula I, wherein:
- $A_1$, $A_2$ and $A_3$ are each independently selected from C and O;
- $R_1$, $R_2$, $R_3$, $R_4$, $R_5$, and $R_6$ are each independently selected from —H, -halo, —$C_{1-6}$ alkyl, and —O—$C_{1-6}$ alkyl; and
- x and y are each independently selected from 1 or 2; and having a predicted lowest active concentration of 0.1 μM or less, when making use of the method according to this invention; for use as an anti-invasive compound.

In a further aspect this invention provides a compound of Formula I or a stereoisomer, tautomer, racemic, metabolite, pro- or predrug, salt, hydrate, or solvate thereof, wherein:
- $A_1$, $A_2$ and $A_3$ are each independently selected from C and O;
- $R_1$, $R_2$, $R_3$, $R_4$, $R_5$, and $R_6$ are each independently selected from —H, -halo, —$C_{1-6}$ alkyl, and —O—$C_{1-6}$ alkyl; and
- x and y are independently selected from 1 or 2, and wherein at least one of x and y is 1;

and having a predicted lowest active concentration of 0.1 μM or less, when making use of the method according to this invention; for use as an anti-invasive compound.

In yet a further embodiment, this invention provides a compound of Formula I or a stereoisomer, tautomer, racemic, metabolite, pro- or predrug, salt, hydrate, or solvate thereof, wherein:
- $A_1$ is C, one of $A_2$ and $A_3$ is C and the other one of $A_2$ and $A_3$ is O;
- $R_1$, $R_2$, and $R_3$ are each independently selected from —H, -halo, and —O—$C_{1-6}$ alkyl;
- $R_4$, $R_5$, and $R_6$ are each H;
- x is 2; and
- y is 1;

and having a predicted lowest active concentration of 0.1 μM or less, when making use of the method according to claim 1; for use as an anti-invasive compound.

In yet a further embodiment this invention provides a compound of Formula Ia or a stereoisomer, tautomer, racemic, metabolite, pro- or predrug, salt, hydrate, or solvate thereof,

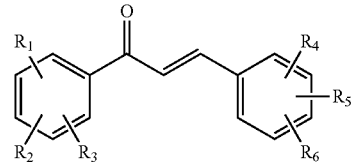

Ia wherein:
- $R_1$, $R_2$, $R_3$, $R_4$, $R_5$, and $R_6$ are each independently selected from —H, -halo, —$C_{1-6}$ alkyl, and —O—$C_{1-6}$ alkyl;

and having a predicted lowest active concentration of 0.1 μM or less, when making use of the method according to this invention; for use as an anti-invasive compound.

In an even further embodiment, this invention provides a compound of Formula Ia or a stereoisomer, tautomer, racemic, metabolite, pro- or predrug, salt, hydrate, or solvate thereof, wherein:
- $R_1$, $R_2$, and $R_3$, are each independently selected from —H, -halo, and —O—$C_{1-6}$ alkyl;
- $R_4$, and $R_5$ are each —H; and $R_6$ is -halo and having a predicted lowest active concentration of 0.1 μM or less, when making use of the method according to claim 1 for use as an anti-invasive compound.

In yet a further embodiment, this invention provides a compound of Formula Ib or a stereoisomer, tautomer, racemic, metabolite, pro- or predrug, salt, hydrate, or solvate thereof,

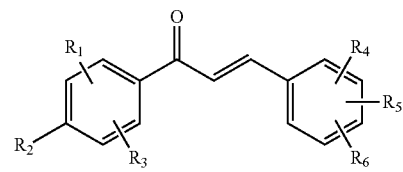

Ib wherein:
- $R_1$, $R_3$, $R_4$, $R_5$, and $R_6$ are each independently selected from —H, -halo, and —O—$C_{1-6}$ alkyl; and
- $R_2$ is selected from -halo, and —O—$C_{1-6}$ alkyl;

and having a predicted lowest active concentration of 0.1 μM or less, when making use of the method according to claim 1; for use as an anti-invasive compound.

In a further embodiment, this invention provides a compound of Formula Ic or a stereoisomer, tautomer, racemic, metabolite, pro- or predrug, salt, hydrate, or solvate thereof,

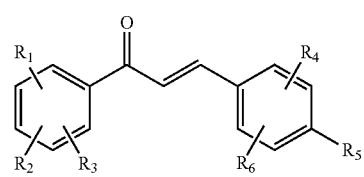

Ic wherein:
- $R_1$, $R_2$, $R_3$, $R_4$, and $R_6$ are each independently selected from —H, -halo, and —O—$C_{1-6}$ alkyl; and
- $R_5$ is selected from -halo, and —O—$C_{1-6}$ alkyl;

and having a predicted lowest active concentration of 0.1 μM or less, when making use of the method according to claim 1; for use as an anti-invasive compound.

In yet a further embodiment, this invention provide a compound of Formula Id or a stereoisomer, tautomer, racemic, metabolite, pro- or predrug, salt, hydrate, or solvate thereof,

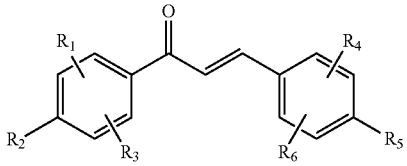

Id wherein:
$R_1$, $R_3$, $R_4$, and $R_6$ are each independently selected from —H, -halo, and —O—$C_{1-6}$ alkyl; and
$R_2$ and $R_5$ are each independently selected from -halo, and —O—$C_{1-6}$ alkyl;

and having a predicted lowest active concentration of 0.1 μM or less, when making use of the method according to claim 1; for use as an anti-invasive compound.

In yet a further embodiment, this invention provide a compound of Formula Ie or a stereoisomer, tautomer, racemic, metabolite, pro- or predrug, salt, hydrate, or solvate thereof,

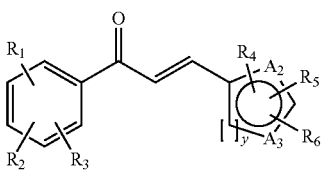

Ie wherein:
one of $A_2$ and $A_3$ is O and the other one is C
$R_1$, $R_2$, $R_3$, $R_4$, $R_5$, and $R_6$ are each independently selected from —H, -halo, —$C_{1-6}$ alkyl, and —O—$C_{1-6}$ alkyl; and
y is selected from 1 or 2.

and having a predicted lowest active concentration of 0.1 μM or less, when making use of the method according to claim 1; for use as an anti-invasive compound.

In a further embodiment, the present invention provides a compound of Formula I, Ia, Ib, Ic and/or Id, Ie as specified herein; wherein said compound has an anti-invasive activity at a concentration of 0.1 μM; or even more specific at a concentration of 0.01 μM or less. The anti-invasive activity can be determined in vitro, for example by using the chicken heart invasion assay described by Bracke et al., 2001. More specific, the invention includes said compound for use as an anti-invasive compound. It is of particular advantage that these compounds, at said specific concentration, are not toxic and have no negative effect on the survival and proliferation of the cells, including healthy cells, which will result in reduced side effects normally associated with cytotoxic compounds when used in therapy.

In a further aspect, the present invention provides a compound of Formula II or a stereoisomer, tautomer, racemic, metabolite, pro- or predrug, salt, hydrate, or solvate thereof,

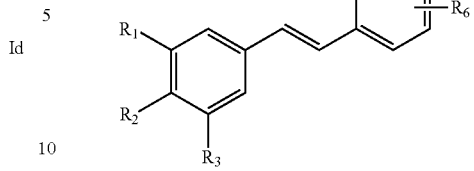

II wherein:
$R_1$, $R_2$, $R_3$, $R_4$, $R_5$, and $R_6$ are each independently selected from —H, -halo, —$C_{1-6}$ alkyl, and —O—$C_{1-6}$ alkyl;
wherein at least one of $R_1$, $R_2$ and $R_3$ is not —H;
for use as an anti-invasive compound. More specific, said compound has an anti-invasive activity (e.g. as determined by the chicken heart invasion assay described by Bracke et al., 2001) at a concentration of 0.1 μM or less.

In a specific embodiment, this invention provides a compound of Formula II or a stereoisomer, tautomer, racemic, metabolite, pro- or predrug, salt, hydrate, or solvate thereof, wherein:
$R_1$, $R_2$ and $R_3$ are each —O—$C_{1-6}$ alkyl; and
$R_4$, $R_5$, and $R_6$ are each independently selected from —H, -halo, —$C_{1-6}$ alkyl, and —O—$C_{1-6}$ alkyl
for use as an anti-invasive compound. More specific, said compound has an anti-invasive activity (e.g. as determined by the chicken heart invasion assay described by Bracke et al., 2001) at a concentration of 0.1 μM or less.

In yet a further embodiment, this invention provides a compound of Formula IIa or a stereoisomer, tautomer, racemic, metabolite, pro- or predrug, salt, hydrate, or solvate thereof

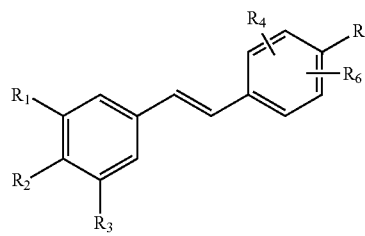

IIa wherein:
$R_1$, $R_2$, and $R_3$ are each independently selected from —H, -halo, —$C_{1-6}$ alkyl, and —O—$C_{1-6}$ alkyl;
wherein at least one of $R_1$, $R_2$ and $R_3$ is not —H;
$R_4$ and $R_6$ are each independently selected from —H, -halo, —$C_{1-6}$ alkyl, and —O—$C_{1-6}$ alkyl;
$R_5$ is selected from -halo, —$C_{1-6}$ alkyl, and —O—$C_{1-6}$ alkyl;
for use as an anti-invasive compound. More specific, said compound has an anti-invasive activity (e.g. as determined by the chicken heart invasion assay described by Bracke et al., 2001) at a concentration of 0.1 μM or less.

This invention also provides a compound of formula II or IIa, wherein the double bond in the linker between the aryl or heteroaryl moieties has the Z configuration; and having an active concentration of 0.1 μM or less; for use as an anti-invasive compound.

In a particular embodiment, this invention provides a compound of formula II or IIa, wherein said compound is selected from the list consisting of:

1,1-(E)-ethene-1,2-diylbis(4-fluorobenzene);
1-fluoro-4-[(E)-2-(4-methoxyphenyl)ethenyl]benzene;
1-fluoro-4-[(Z)-2-phenylethenyl]benzene;
1,2,3-trimethoxy-5-[(Z)-2-phenylethenyl]benzene;
5-[(Z)-2-(4-fluorophenyl)ethenyl]-1,2,3-trimethoxybenzene;
1,1'-(E)-ethene-1,2-diyldibenzene; and
1,2,3-trimethoxy-5-[(E)-2-phenylethenyl]benzene;
or a stereoisomer, tautomer, racemic, metabolite, pro- or pre-drug, salt, hydrate, or solvate thereof.

In another specific embodiment, the present invention provides a compound according to formula I, Ia, Ib, Ic, Id or Ie; said compound being selected from the list consisting of:
(2E)-3-(4-fluorophenyl)-1-(3,4,5-trimethoxyphenyl)prop-2-en-1-one;
(2E)-3-(4-chlorophenyl)-1-(4-methoxyphenyl)prop-2-en-1-one;
(2E)-1-(4-methoxyphenyl)-3-(2,4,6-trimethoxyphenyl)prop-2-en-1-one;
(2E)-3-(3-fluorophenyl)-1-(4-fluorophenyl)prop-2-en-1-one;
(2E)-3-(furan-2-yl)-1-(3,4,5-trimethoxyphenyl)prop-2-en-1-one;
(2E)-1-(2,6-dimethoxyphenyl)-3-(furan-2-yl)prop-2-en-1-one;
(2E)-1-(4-fluorophenyl)-3-(furan-3-yl)prop-2-en-1-one; and
(2E)-1,3-di(furan-2-yl)prop-2-en-1-one;
or a stereoisomer, tautomer, racemic, metabolite, pro- or pre-drug, salt, hydrate, or solvate thereof.

More specific, said compound has an anti-invasive activity (e.g. as determined by the chicken heart invasion assay described by Bracke et al., 2001) at a concentration of 0.1 µM or less. Even more specific, said compound has an anti-invasive activity at a concentration of 0.01 µM or less. Furthermore, the present invention provides said compound for use as an anti-invasive compound.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

Medical Use

The spread of cancer from its tissue of origin and its subsequent growth in other organs is the most life-threatening aspect of the disease. This process is called metastasis, and requires cancer cells to survive and proliferate outside their tissue of origin. The first crucial step in this process is the invasion of cancer cells into tissue surrounding the tumor and the vasculature.

The compounds of the present invention are capable to inhibit said first step and thereby prevent and/or reduce cancer cell dissemination and metastasis formation. As such, the invention relates to the compounds described herein for use in treating cancer by inhibiting the invasion of tumor cells into surrounding or adjacent tissue, cells and/or their entry into the circulatory system. Hence the compounds of the invention are especially useful for inhibiting or stopping tumor spread.

In a specific aspect, the compound of the invention is used as an anti-invasive compound. "Anti-invasive" refers to the ability to inhibit invasion of the tumor or cancer cell into surrounding tissue (within or outside the organ of origin). For determining whether a compound exhibits an anti-invasive behavior the chicken-heart invasion assay as described in Bracke et al., 2001 may be applied. This screening method confronts cancer cells with a fragment of normal tissue, so as not to neglect the contribution of the host tissue in the micro-ecosystem that governs tumor behavior. The interaction between the cancer cells and the normal tissue is evaluated histologically and classified along a 5-grades subjective scale. Grades III and IV are typical for invasion, while grades 0, I and II correspond to absence of invasion. Compounds that inhibit invasion of confronting cancer cells i.e. from III/IV to 0/I/II, are determined as anti-invasive. Possible alternative assays generally known in the art are the type I collagen invasion assay and the Matrigel invasion assay.

This invention further provides a pharmaceutical composition for use as an anti-invasive composition; said composition comprising a compound according to this invention and a pharmaceutically acceptable carrier, diluent and/or excipient.

In yet a further aspect this invention provides a method for preventing or inhibiting the invasiveness of tumor cells; said method comprising contacting said cells with a pharmaceutically effective amount of a compound or a composition according to this invention.

In a further aspect this invention provides a method for inhibiting invasion of tumor cells into the surrounding tissue in a subject having a condition associated with undesired cell migration; said method comprising administering to said subject a therapeutically effective amount of a compound or a composition according to this invention. Said condition in particular being characterized by the presence of a solid malignant tumor; more in particular said condition being selected from the list comprising mammary tumors, prostate tumors, colorectal tumors, lung tumors, brain tumors, head and neck tumors, melanoma, sarcoma, or ovarian tumors.

The present invention further provides a method for the treatment of at least one disease or disorder associated with undesired cell migration; in particular being associated with solid malignant tumors; more in particular selected from the list comprising mammary tumors, prostate tumors, colorectal tumors, lung tumors, brain tumors, head and neck tumors, melanoma, sarcoma, and ovarian tumors.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethylbromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms which may be solid, semi-solid or liquid, depending on the manner of administration as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, disintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the Formula I, II or III or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also for economically important animals such as cattle, pigs, sheep, chicken, fish, etc. enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

A. Physicochemical Properties of the Compounds

Detailed information for the training set compounds 1-34 can be found in their corresponding references as indicated in table 10 below.

Compound 42: (2E)-3-(2,4,5-Trimethoxyphenyl)-1-(2,4,6-trimethoxyphenyl)propenone $^1$H NMR (CDCl$_3$, 300 MHz, ppm): δ=3.77 (s, 6H, 2×OMe), 3.81 (s, 3H, OMe), 3.85 (s, 3H, OMe) 3.86 (s, 3H, OMe), 3.92 (s, 3H, OMe), 6.16 (s, 1H, H$^{3'}$, H$^{5'}$), 6.47 (s, 1H, H$^3$), 6.90 (d, 1H, J$_{trans}$=16.1 Hz, H$^\alpha$), 7.04 (s, 1H, H$^6$), 7.66 (d, 1H, J$_{trans}$=16.1 Hz, H$^\beta$); $^{13}$C NMR (CDCl$_3$, 75 MHz, ppm): δ=55.42 (OMe), 55.90 (2×OMe), 56.03 (OMe), 56.40 (2×OMe), 90.75 (C$^{3'}$, C$^{5'}$), 96.92 (C$^3$), 110.82 (C$^6$), 112.17 (C$^1$), 115.44 (C$^1$), 127.14 (C$^\alpha$), 139.72 (C$^q$O), 143.25 (C$^\beta$), 152.27 (C$^q$O), 154.13 (C$^q$O), 158.67 (2×C$^q$O), 162.13 (C$^q$O), 194.87 (C=O); IR (KBr, cm$^{-1}$): ν=1634 (C=O), 1600 (C=C), 1586, 1208, 1152, 1124, 1026, 812; MS (ES$^+$): m/z (%): 389.1 ([M+H]$^+$, 100), 390.1 ([M+1+H]$^+$, 23) 799.3 (6); MP (° C.): 127.5-128.5° C.

Yield: 78%, yellow crystals.

Compound 43: (2E)-3-(4-Methoxyphenyl)-1-(2,4,6-trimethoxyphenyl)propenone $^1$H NMR (CDCl$_3$, 300 MHz, ppm): δ=3.77 (s, 6H, 2×OMe), 3.83 (s, 3H, OMe), 3.86 (s, 3H, OMe), 6.16 (s, 2H, H$^{3'}$, H$^{5'}$), 6.87 (d, 1H, J$_{trans}$=16.0 Hz, H$^\alpha$), 6.89 (d, 2H, J$_{H,vic}$=8.5 Hz, H$^3$, H$^5$), 7.31 (d, 1H, J$_{trans}$=16.0 Hz, H$^\beta$), 7.48 (d, 2H, J$_{H,vic}$=8.5 Hz, H$^2$, H$^6$); $^{13}$C NMR (CDCl$_3$, 75 MHz, ppm): δ=55.36 (OMe), 55.44 (OMe), 55.90 (2×OMe), 90.69 (C$^{3'}$, C$^{5'}$), 111.88 (C$^{1'}$), 114.27 (C$^3$, C$^5$), 126.97 (C$^\alpha$), 127.63 (C$^1$), 130.08 (C$^2$, C$^6$), 144.27 (C$^{62}$), 158.71 (C$^{2'}$, C$^{6'}$), 161.40 (C$^q$O), 162.27 (C$^q$O), 194.42 (C=O); IR (KBr, cm$^{-1}$): ν=1672, 1634 (C=O), 1594 (C=C), 1572, 1512, 1253, 1222, 1200, 1174, 1152, 1127, 1020, 820, 804; MS (ES$^+$): m/z (%): 329.1 ([M+H]$^+$, 100), 330.1 ([M+1+H]$^+$, 21), 679.2 (13), 680.2 (5); MP (° C.): 118.5-119.5° C.

Yield: 69%, pale-yellow crystals.

Compound 44: (2E)-3-(2,4,5-Trimethoxyphenyl)-1-(4-methoxyphenyl)propenone $^1$H NMR (CDCl$_3$, 300 MHz, ppm): δ=3.88 (s, 3H, OMe), 3.90 (s, 3H, OMe), 3.90 (s, 3H, OMe), 3.94 (s, 3H, OMe), 6.52 (s, 1H, H$^3$), 6.97 (d, 2H, J$_{H,vic}$=8.8 Hz, H$^{3'}$, H$^{5'}$), 7.13 (s, 1H, H$^6$), 7.48 (d, 1H, J$_{trans}$=15.7 Hz, H$^\alpha$), 8.03 (d, 2H, J$_{H,vic}$=8.8 Hz, H$^{2'}$, H$^{6'}$), 8.09 (d, 1H, J$_{trans}$=15.7 Hz, H$^\beta$); $^{13}$C NMR (CDCl$_3$, 75 MHz, ppm): δ=55.41 (OMe), 56.00 (OMe), 56.29 (OMe), 56.51 (OMe), 96.77 (C$^3$), 111.30 (C$^6$), 113.69 (C$^{3'}$, C$^{5'}$), 115.53 (C$^\alpha$), 119.85 (C$^\alpha$), 130.65 (C$^{2'}$, C$^{6'}$), 131.56 (C$^{1'}$), 139.26 (C$^\beta$), 143.15 (C$^q$O), 152.30 (C$^q$O), 154.51 (C$^q$O), 163.08 (C$^q$O), 189.22 (C=O); IR (KBr, cm$^{-1}$): ν=1466, 1504, 1563, 1584, 1603 (C=C), 1646 (C=O); MS (ES$^+$): m/z (%): 329.2 ([M+H]$^+$, 100); MP (° C.): 124° C.

Yield: 92%, yellow crystals.

Compound 45: (2E)-1-(4-methoxyphenyl)-3-(2,4,6-trimethoxyphenyl)prop-2-en-1-one

This molecule has been reported by Okunrobo et al., 2006

Compound 46: (2E)-3-(2,4,5-Trimethoxyphenyl)-1-(2,6-dimethoxyphenyl)propenone $^1$H NMR (CDCl$_3$, 300 MHz, ppm): δ=3.78 (s, 6H, 2×OMe), 3.80 (s, 3H, OMe), 3.85 (s, 3H, OMe), 3.92 (s, 3H, OMe), 6.47 (s, 1H, H$^3$), 6.62 (d, 2H, J$_{H,vic}$=8.5 Hz, H$^{3'}$, H$^{5'}$), 6.91 (d, 1H, J$_{trans}$=16.1 Hz, H$^\alpha$), 7.04 (s, 1H, H$^6$), 7.32 (t, 1H, J$_{H,vic}$=8.5 Hz, H$^4$), 7.63 (d, 1H, J$_{trans}$=16.1 Hz, H$^\beta$); $^{13}$C NMR (CDCl$_3$, 75 MHz, ppm): δ=55.99 (2×OMe), 56.06 (OMe), 56.45 (OMe), 56.49 (OMe), 97.01 (C$^3$), 104.19 (C$^{3'}$, C$^{5'}$), 110.97 (C$^6$), 115.49 (C$^1$), 119.09 (C$^1$), 126.79 (C$^\alpha$), 130.42 (C$^4$), 140.39 (C$^\beta$), 143.35 (C$^q$O), 152.39 (C$^q$O), 154.21 (C$^{q,2}$O), 157.54 (C$^{2'}$, C$^{6'}$), 195.49 (C=O); IR (KBr, cm$^{-1}$): ν=1473, 1510, 1599 (C=C), 1638 (C=O); MS (ES$^+$): m/z (%): 359.2 ([M+H]$^+$, 100); MP (° C.): 157.7° C.

Yield: 62%, pale-yellow crystals.

Compound 47: (2E)-3-(2,4,6-Trimethoxyphenyl)-1-(2,6-dimethoxyphenyl)propenone $^1$H NMR (CDCl$_3$, 300 MHz, ppm): δ=3.76 (s, 6H, 2×OMe), 3.79 (s, 6H, 2×OMe), 3.82 (s, 3H, OMe), 6.07 (s, 2H, H$^3$, H$^5$), 6.59 (d, 2H, =8.3 Hz, H$^{3'}$, H$^{5'}$), 7.28 (t, 1H, J$_{H,vic}$=8.3 Hz, H$^4$), 7.31 (d, 1H, J$_{trans}$=16.4 Hz, H$^\alpha$), 7.77 (d, 1H, J$_{trans}$=16.4 Hz, H$^\beta$); $^{13}$C NMR (CDCl$_3$, 75 MHz, ppm): δ=55.35 (OMe), 55.71 (2×OMe), 55.96 (2×OMe), 90.46 (C$^3$, C$^5$), 104.13 (C$^{3'}$, C$^{5'}$), 106.28 (C$^1$), 119.40 (C$^1$), 128.66 (C$^\alpha$), 130.07 (C$^4$), 137.37 (C$^\beta$), 157.49 (2×C$^q$O), 161.48 (2×C$^q$O), 163.12 (C$^4$), 197.25 (C=O); IR (KBr, cm$^{-1}$): ν=1454, 1471, 1563, 1584, 1611 (C=C), 1664 (C=O); MS (ES$^+$): m/z (%): 359.2 ([M+H]$^+$, 100); MP (° C.): 158° C.

Yield: 64%, pale-yellow crystals.

Compound 49: (2E)-3-(4-Fluorophenyl)-1-(3,4,5-trimethoxyphenyl)propenone $^1$H NMR (CDCl$_3$, 300 MHz, ppm): δ=3.94 (s, 3H, OMe), 3.95 (s, 6H, 2×OMe), 7.11 (dd, 1H, J$_{H,vic}$=8.5 Hz, J$_{HF}$=8.5 Hz, H$^3$, H$^5$), 7.28 (s, 2H, H$^{2'}$, H$^{6'}$), 7.42 (d, 1H, J$_{trans}$=15.4 Hz, H$^\alpha$), 7.64 (dd, 2H, J$_{H,vic}$=8.5 Hz, J$_{HF}$=5.2 Hz, H$^2$, H$^6$), 7.78 (d, 1H, J$_{trans}$=15.4 Hz, H$^\beta$); $^{13}$C NMR (CDCl$_3$, 75 MHz, ppm): δ=56.32 (2×OMe), 60.95 (OMe), 106.02 (C$^{2'}$, C$^{5'}$), 116.09 (C$^3$, C$^5$, J$_{CF}$=21.9 Hz), 121.34 (C$^\alpha$), 130.40 (C$^2$, C$^6$, J$_{CF}$=8.1 Hz), 131.15 (C$^1$, J$_{CF}$=3.5 Hz), 133.38 (C$^\beta$), 142.51 (C$^{1'}$), 143.35 (C$^{4'}$O), 153.15 (C$^{3'}$, C$^{5'}$), 164.01 (C$^\alpha$, J$_{CF}$=251.5 Hz), 188.85 (C=O); $^{19}$F NMR (CDCl$_3$, 282 MHz, ppm): δ=(−)109.57-(−)109.35 (m); IR (ATR, cm$^{-1}$): ν=1124, 1157, 1227, 1338, 1504, 1580, 1599, 1611, 1660 (C=O); MS (ES$^+$): m/z (%): 317.1 ([M+H]$^+$, 100), 318.1 (18), 339.1 (8), 655.2 (8); MP (° C.): 124-125° C.

Yield: 69%, off-white needles.

Compound 52: (2E)-3-(4-chlorophenyl)-1-(4-methoxyphenyl)prop-2-en-1-one

This molecule has been reported by Kumar et al. 2010

Compound 53: (2E)-3-(3-Fluorophenyl)-1-(4-fluorophenyl)propenone $^1$H NMR (CDCl$_3$, 300 MHz, ppm): δ=7.05-7.16 (m, 1H, H$^4$), 7.17 (dd, 1H, J$_{H,vic}$=8.8 Hz, J$_{HF}$=8.8 Hz, H$^{3'}$, H$^{5'}$), 7.29-7.43 (m, 3H, H$^1$, H$^5$, H$^6$), 7.49 (d, 1H, J$_{trans}$=15.7 Hz, H$^\alpha$), 7.75 (d, 1H, J$_{trans}$=15.7 Hz, H$^\beta$), 8.06 (dd, 2H, J$_{Hvic}$=8.8 Hz, J$_{HF}$=5.5 Hz, H$^{2'}$, H$^{6'}$); $^{13}$C NMR (CDCl$_3$, 75 MHz, ppm): δ=77.16 (CDCl$_3$), 114.47 (C$^4$, J$_{CF}$=21.9 Hz), 115.81 (C$^{3'}$, C$^{5'}$, J$_{CF}$=21.9 Hz), 117.44 (C$^2$, J$_{CF}$=21.9 Hz), 122.64 (C$^\alpha$), 124.64 (C$^6$, J$_{CF}$=2.3 Hz), 130.54 (C$^5$, J$_{CF}$=8.1 Hz), 131.16 (C$^{2'}$, C$^{6'}$, J$_{CF}$=9.2 Hz), 134.26 (C$^{1'}$, J$_{CF}$=2.3 Hz), 137.04 (C$^1$, J$_{CF}$=6.9 Hz), 143.38 (C$^\beta$), 163.03 (CF, J$_{CF}$=246.9 Hz), 165.71 (CF, J$_{CF}$=255.0 Hz), 188.30 (C=O); $^{19}$F NMR (CDCl$_3$, 282 MHz, ppm): δ=(−)112.95-(−)112.75 (m, CF), (−)105.65-(−)105.49 (m, CF); IR (ATR, cm$^{-1}$): ν=1669 (C=O), 1609, 1598 (C=O), 1583, 1444, 1227, 1207, 1159, 1141, 834, 779; MS (ES$^+$): m/z (%): 245.0 ([M+H]$^+$, 100), 246.1 ([M+1+H]$^+$, 15); MP (° C.): 94-95° C.

Yield: 70%, pale yellow needles.

Compound 54: (2E)-3-(3-Fluorophenyl)-1-(4-methoxyphenyl)propenone $^1$H NMR (CDCl$_3$, 300 MHz, ppm): δ=3.89 (s, 3H, OMe), 6.99 (dd, 1H, J$_{H,vic}$=9.1 Hz, H$^{3'}$, H$^{5'}$), 7.04-7.16 (m, 1H, H$^4$), 7.29-7.44 (m, 3H, H², H⁵, H⁶), 7.53 (d, 1H, $J_{trans}$=15.7 Hz, H^α), 7.75 (d, 1H, $J_{trans}$=15.7 Hz, H^β), 8.04 (d, 2H, =9.1 Hz, H²', H⁶'); ¹³C NMR (CDCl₃, 75 MHz, ppm): δ=55.48 (OMe), 113.92 (C³', C⁵'), 114.37 (C⁴, $J_{CF}$=21.9 Hz), 117.12 (C², $J_{CF}$=20.8 Hz), 123.00 (C^α), 124.48 (C⁶, $J_{CF}$=2.3 Hz), 130.46 (C⁵, $J_{CF}$=8.1 Hz), 130.88 (C¹', C²', C⁵'), 137.37 (C¹, $J_{CF}$=6.9 Hz), 142.39 (C^β, $J_{CF}$=2.3 Hz), 163.03 (C³, $J_{CF}$=246.9 Hz), 163.60 (C⁴'O), 188.24 (C=O); ¹⁹F NMR (CDCl₃, 282 MHz, ppm): δ=(−)113.15-(−)112.99 (m); IR (ATR, cm⁻¹): ν=1662 (C=O), 1612, 1596, 1584 (C=C), 1446, 1337, 1261, 1239, 1199, 1172, 1144, 1017, 1000, 967, 828, 774; MS (ES⁺): m/z (%): 257.1 ([M+H]⁺, 100), 258.1 ([M+1+H]⁺, 17), 279.1 ([M+Na]⁺, 6); MP (° C.): 104.5-105.5° C.

Yield: 76%, white crystals.

Compound 60: (2E)-3-Phenyl-1-[4-(3-methylbut-2-enyloxy)phenyl]propenone

¹H NMR (CDCl₃, 300 MHz, ppm): δ=1.77 (br. s, 3H, Me), 1.82 (br. s, 3H, Me), 4.60 (d, 2H, $J_{vic}$=6.6 Hz, OCH₂), 5.51 (tt, 1H, $J_{vic}$=6.6 Hz, $J_{allyl}$=1.4 Hz, =CH), 6.99 (d, 2H, $J_{vic}$=9.1 Hz, H³', H⁵'), 7.37-7.47 (m, 3H, H³, H⁴, H⁵), 7.56 (d, 1H, $J_{trans}$=15.7 Hz, H^α), 7.61-7.69 (m, 2H, H², H⁶), 7.81 (d, 1H, $J_{trans}$=15.7 Hz, H^β), 8.04 (d, 2H, $J_{vic}$=9.1 Hz, H²', H⁵'); ¹³C NMR (CDCl₃, 75 MHz, ppm): δ=18.28 (Me), 25.85 (Me), 65.04 (OCH₂), 114.51 (C³', C⁵'), 118.98 (=CH), 121.90 (C^α), 128.36 (C², C⁶), 128.92 (C³, C⁵), 130.31 (C⁴), 130.80 (C²', C⁵'), 130.95 (C¹'), 135.12 (C¹), 138.97 (C^q), 143.90 (C^β), 162.80 (C⁴'O), 188.71 (C=O); IR (KBr, cm⁻¹): ν=1574, 1597, 1610 (C=C), 1657 (C=O); MS (ES⁺): m/z (%): 293.2 ([M+H]⁺, 100); MP (° C.): 63-64° C.

Yield: 86%, yellow-orange crystals.

Compound 61: (2E)-3-(4-Chlorophenyl)-1-[4-(3-methylbut-2-enyloxy)phenyl]propenone ¹H NMR (CDCl₃, 300 MHz, ppm): δ=1.77 (br. s, 3H, Me), 1.82 (br. s, 3H, Me), 4.60 (d, 2H, $J_{vic}$=6.6 Hz, OCH₂), 5.50 (tt, 1H, $J_{vic}$=6.6 Hz, $J_{allyl}$=1.4 Hz, =CH), 6.99 (d, 2H, $J_{vic}$=8.8 Hz, H³', H⁵'), 7.39 (d, 2H, $J_{H,vic}$=8.3 Hz, H³, H⁵), 7.53 (d, 1H, $J_{trans}$=15.7 Hz, H^α), 7.58 (d, 2H, $J_{vic}$=8.3 Hz, H², H⁶), 7.75 (d, 1H, $J_{trans}$=15.7 Hz, H^β), 8.03 (d, 2H, $J_{vic}$=8.8 Hz, H²', H⁵'); ¹³C NMR (CDCl₃, 75 MHz, ppm): δ=18.26 (Me), 25.85 (Me), 65.04 (OCH₂), 114.53 (C³', C⁵'), 118.91 (=CH), 122.27 (C^α), 129.18 (C³, C⁵), 129.50 (C², C⁶), 130.74 (C^q), 130.82 (C²', C⁵'), 133.58 (C^q), 136.15 (C^q), 139.03 (C^q), 142.38 (C^β), 162.90 (C^q,⁴'O), 188.35 (C=O); IR (KBr, cm⁻¹): ν=1566, 1574, 1603 (C=C), 1657 (C=O); MS (ES⁺): m/z (%): 327.2 ([M+H]⁺, 100), 329.2 ([M+2+H]⁺, 32); MP (° C.): 140.5-142° C.

Yield: 86%, yellow crystals.

Compound 62: (2E)-3-(4-Fluorophenyl)-1-[4-(3-methylbut-2-enyloxy)phenyl]propenone ¹H NMR (CDCl₃, 300 MHz, ppm): δ=1.77 (br. s, 3H, Me), 1.82 (br. s, 3H, Me), 4.60 (d, 2H, $J_{vic}$=6.6 Hz, OCH₂), 5.50 (txt, 1H, $J_{vic}$=6.6 Hz, $J_{allyl}$=1.4 Hz, =CH), 6.99 (d, 2H, $J_{vic}$=9.1 Hz, H³', H⁵'), 7.11 (dd, 2H, $J_{H,vic}$=8.8 Hz, $J_{HF}$=8.8 Hz, H³, H⁵), 7.48 (d, 1H, $J_{trans}$=15.7 Hz, H^α), 7.63 (dd, 2H, $J_{Hvic}$=8.8 Hz, $J_{HF}$=5.5 Hz, H², H⁶), 7.77 (d, 1H, $J_{trans}$=15.7 Hz, H^α), 8.03 (d, 2H, $J_{vic}$=9.1 Hz, H²', H⁶'); ¹³C NMR (CDCl₃, 75 MHz, ppm): δ=18.56 (Me), 26.15 (Me), 65.33 (OCH₂), 114.80 (C³', C⁵'), 116.36 (d, $J_{CF}$=21.9 Hz, C³, C⁵), 119.23 (=CH), 121.85 (C^α), 130.53 (d, $J_{CF}$=8.1 Hz, C², C⁶), 131.09 (C²', C⁵'), 131.61 (C^q), 131.66 (C^q), 139.32 (C¹'), 142.86 (C^β), 163.14 (C⁴'), 164.21 (d, $J_{CF}$=251.5 Hz, C⁴), 188.73 (C=O); ¹⁹F NMR (CDCl₃, 282 MHz, ppm): δ=(−)109.5-(−)109.3 (m); IR (KBr, cm⁻¹): ν=1508, 1590, 1597, 1611 (C=C), 1658 (C=O); MS (ES⁺): m/z (%): 311.2 ([M+H]⁺, 100); MP (° C.): 107-108° C.

Yield: 99%, yellow crystals.

Compound 65: (2E)-3-[4-(3-Methylbut-2-enyloxy)phenyl]-1-phenylpropenone

¹H NMR (CDCl₃, 300 MHz, ppm): δ=1.76 (br. s, 3H, Me), 1.81 (br. s, 3H, Me), 4.56 (d, 2H, $J_{vic}$=6.9 Hz, OCH₂), 5.50 (txt, 1H, $J_{vic}$=6.9 Hz, $J_{allyl}$=1.4 Hz, =CH), 6.95 (d, 2H, $J_{vic}$=8.8 Hz, H³, H⁵), 7.46-7.57 (m, 3H, H³', H⁴', H⁵'), 7.42 (d, 1H, $J_{trans}$=15.7 Hz, H^α), 7.60 (d, 2H, $J_{vic}$=8.8 Hz, H², H⁶), 7.79 (d, 1H, $J_{trans}$=15.7 Hz, H^β), 8.01 (d, 2H, $J_{vic}$=8.8 Hz, $J_{allyl}$=1.4 Hz, H²', H⁶'); ¹³C NMR (CDCl₃, 75 MHz, ppm): δ=18.25 (Me), 25.85 (Me), 64.92 (OCH₂), 115.08 (C³, C⁵), 119.14 (=CH), 119.63 (C^α), 127.46 (C¹), 128.42 (C²', C⁶'), 128.56 (C³', C⁵'), 130.24 (C², C⁶), 132.54 (C⁴'), 138.51 (C^q), 138.79 (C^q), 144.80 (C_β), 161.03 (C⁴), 190.59 (C=O); IR (KBr, cm⁻¹): ν=1510, 1571, 1590, 1599 (C=C), 1655 (C=O); MS (ES⁺): m/z (%): 293.2 ([M+H]⁺, 100); MP (° C.): 71-72° C.

Yield: 95%, yellow-orange crystals.

Compound 68: 1-(2-Furyl)-3-(4-fluorophenyl)propenone

¹H NMR (CDCl₃, 300 MHz, ppm): 5=6.60 (dd, 1H, $J_{vic,1}$=3.6 Hz, $J_{vic,2}$=1.7 Hz, H⁴), 7.11 (dd, $J_{vic}$=8.5 Hz, $J_{HF}$=8.5 Hz, 2H, H³, H⁵), 7.33 (d, 1H, $J_{vic}$=3.6 Hz, H⁵), 7.38 (d, 1H, $J_{trans}$=15.7 Hz, H^α), 7.61-7.64 (m, 3H, H³', H², H⁶), 7.84 (d, 1H, $J_{trans}$=15.7 Hz, H^β); ¹³C NMR (CDCl₃, 75 MHz, ppm): δ=112.62 (C⁴'), 116.12 (d, $J_{CF}$=21.9 Hz, C³, C⁵), 117.58 (C⁵'), 120.86 (C^α), 130.46 (d, $J_{CF}$=9.2 Hz, C², C⁶), 130.98 (d, $J_{CF}$=3.5 Hz, C¹), 142.63 (C^β), 146.59 (C³'), 153.63 (C¹'), 164.09 (d, $J_{CF}$=252.7 Hz, C⁴), 177.83 (C=O); IR (ATR, cm⁻¹): ν=1220, 1463, 1589, 1602 (C=C), 1655 (C=O); MS (ES⁺): m/z (%): 217.3 ([M+H]⁺, 100); MP (° C.): 115-116° C.
Yield: 15%, white crystals, MW=216.06.

Compound 69: (2E)-3-(4-Fluorophenyl)-1-(2-furanyl)propenone

¹H NMR (CDCl₃, 300 MHz, ppm): δ=6.60 (dd, 1H, $J_{vic,1}$=3.6 Hz, $J_{vic,2}$=1.7 Hz, H⁴), 7.11 (dd, $J_{vic}$=8.5 Hz, $J_{HF}$=8.5 Hz, 2H, H³, H⁵), 7.33 (d, 1H, $J_{vic}$=3.6 Hz, H⁵), 7.38 (d, 1H, $J_{trans}$=15.7 Hz, H^α), 7.61-7.64 (m, 3H, H³', H², H⁶), 7.84 (d, 1H, $J_{trans}$=15.7 Hz, W); ¹³C NMR (CDCl₃, 75 MHz, ppm): δ=112.62 (C⁴'), 116.12 (d, $J_{CF}$=21.9 Hz, C³, C⁵), 117.58 (C⁵'), 120.86 (C^α), 130.46 (d, $J_{CF}$=9.2 Hz, C², C⁶), 130.98 (d, $J_{CF}$=3.5 Hz, C¹), 142.63 (C^β), 146.59 (C³'), 153.63 (C¹'), 164.09 (d, $J_{CF}$=252.7 Hz, C⁴), 177.83 (C=O); IR (ATR, cm⁻¹): ν=1220, 1463, 1589, 1602 (C=C), 1655 (C=O); MS (ES⁺): m/z (%): 217.3 ([M+H]⁺, 100); MP (° C.): 115-116° C.
Yield: 15%, white crystals.

Compound 70: 1,3-Difuran-2-yl-propenone

Spectral properties of this substance have been reported by Rasheed et al. 2007 (¹H NMR, ¹³C NMR, IR, MS, melting point).

Compound 73: (2E)-3-(2-Furanyl)-1-(4-fluorophenyl)propenone 73

¹H NMR (CDCl₃, 300 MHz, ppm): ϵ=6.53 (dd, 1H, $J_{vic,1}$=3.5 Hz, $J_{vic,2}$=1.4 Hz, H⁴), 6.74 (d, 1H, $J_{vic}$=3.5 Hz, H⁵), 7.17 (dd, 2H, $J_{HF}$=8.8 Hz, $J_{vic}$=8.8 Hz, H$^{3'}$, H$^{5'}$), 7.43 (d, 1H, $J_{trans}$=15.4 Hz, H$^\alpha$), 7.54 (d, 1H, $J_{vic}$=1.4 Hz, H$^3$), 7.61 (d, 1H, $J_{trans}$=15.4 Hz, H$^\beta$), 8.07 (dd, 2H, $J_{vic}$=8.8 Hz, $J_{HF}$=5.5 Hz, H$^{2'}$, H$^{6'}$); $^{13}$C NMR (CDCl$_3$, 75 MHz, ppm): δ=112.74 (C$^4$), 115.72 (d, $J_{CF}$=21.9 Hz, C$^{3'}$, C$^{5'}$), 116.48, (C$^5$), 118.80 (C$^\alpha$), 130.85 (C$^\beta$), 131.02 (d, $J_{CF}$=9.2 Hz, C$^{2'}$, C$^{6'}$), 134.50 (d, $J_{CF}$=2.3 Hz, C$^{1'}$), 145.03 (C$^5$), 151.60 (C$^2$), 165.61 (d, $J_{CF}$=253.8 Hz, C$^4$), 188.15 (C=O); IR (KBr, cm$^{-1}$): ν=1221, 1260, 1323, 1505, 1555, 1589, 1599 (C=C), 1661 (C=O); MS (ES$^+$): m/z (%): 217.3 ([M+H]$^+$, 100); MP (° C.): 65-66° C.

Yield: 82%; brown crystals.

Compound 74:
3-Furan-2-yl-1-(4-methoxyphenyl)propenone

Spectral properties of this substance have been reported by Kumar et al. 2007 ($^1$H NMR, $^{13}$C NMR, MS, IR), Teh et al. 2006 (crystal structure) and Dureja 1987 (melting point).

Compound 75: (2E)-3-(2-Furanyl)-1-(3,4,5-trimethoxyphenyl)propenone $^1$H NMR (CDCl$_3$, 300 MHz, ppm): δ=3.94 (s, 3H, OMe), 3.96 (s, 6H, 2×OMe), 6.53 (d×d, 1H, $J_{vic,1}$=3.3 Hz, $J_{vic,2}$=1.7 Hz, H$^4$), 6.73 (br. d, 1H, $J_{vic}$=3.3 Hz, H$^5$), 7.30 (s, 2H, H$^{2'}$, H$^{6'}$), 7.41 (d, 1H, $J_{trans}$=15.4 Hz, H$^\alpha$), 7.55 (br. s, 1H, H$^3$), 7.61 (d, 1H, $J_{trans}$=15.4 Hz, H$^\beta$); $^{13}$C NMR (CDCl$_3$, 75 MHz, ppm): δ=56.43 (C3'OMe, C5'OMe), 61.00 (C4'OMe), 106.08 (C$^{2'}$, C$^{6'}$), 112.74 (C$^4$), 116.27 (C$^5$), 118.97 (C$^\alpha$), 130.62 (C$^\beta$), 133.56 (C$^{1'}$), 142.49 (C$^4$), 144.89 (C$^3$), 151.73 (C$^1$), 153.20 (C$^{3'}$, C$^{5'}$), 188.48 (C=O); IR (KBr, cm$^{-1}$): ν=725, 738, 814, 1000, 1013, 1122, 1302, 1332, 1504, 1550, 1574 (C=C), 1652 (C=O); MS (ES$^+$): m/z (%): 289.2 ([M+H]$^+$, 100); MP (° C.): 61-62° C.

Yield: 89%, yellow-brown crystals.

Compound 76: (2E)-3-(2-Furanyl)-1-(2,6-dimethoxyphenyl)propenone $^1$H NMR (CDCl3, 300 MHz, ppm): δ=3.78 (s, 6H, 2×OMe), 6.46 (dd, 1H, =3.3 Hz, $J_{vic,2}$=1.7, H$^4$), 6.60 (d, 2H, $J_{vic}$=8.3 Hz, H$^{3'}$, H$^{5'}$), 6.60 (d, 1H, $J_{vic}$=3.3 Hz, H$^5$), 6.83 (d, 1H, $J_{trans}$=16.0 Hz, H$^\alpha$), 7.08 (d, 1H, $J_{trans}$=16.0 Hz, H), 7.31 (t, 1H, =8.3 Hz, H$^{4'}$), 7.49 (d, 1H, =1.7 Hz, H$^3$); $^{13}$C NMR (CDCl3, 75 MHz, ppm): δ=55.92 (2×OMe), 104.02 (C$^{3'}$, C$^{5'}$), 112.53 (C$^4$), 115.56 (C$^5$), 118.31 (C$^{1'}$), 126.28 (C$^\alpha$), 130.76 (C$^{4'}$), 131.21 (C$^\beta$), 145.02 (C$^3$), 151.26 (C$^1$), 157.54 (C$^{2'}$, C$^{6'}$), 194.73 (C=O); IR (KBr, cm$^{-1}$): ν=1294, 1469, 1593, 1614 (C=C), 1634 (C=O); MS (ES$^+$): m/z (%): 259.3 ([M+H]$^+$, 100); MP (° C.): 89-90° C.

Yield: 65%, brown crystals.

Compound 77: (2E)-3-(3-Furanyl)-1-(4-fluorophenyl)propenone $^1$H NMR (CDCl$_3$, 300 MHz, ppm): δ=6.71 (d, 1H, $J_{vic}$=2.2 Hz, H$^5$), 7.17 (dd, 2H, $J_{HF}$=8.8 Hz, $J_{vic}$=8.8 Hz, H$^{3'}$, H$^{5'}$), 7.21 (d, 1H, $J_{trans}$=15.4 Hz, H$^\alpha$), 7.48 (br s, 1H, H$^2$), 7.69-7.77 (m, 2H, H$^\beta$, H$^4$), 8.03 (dd, 2H, $J_{vic}$=8.8 Hz, $J_{HF}$=5.5 Hz, H$^{2'}$, H$^{6'}$); $^{13}$C NMR (CDCl$_3$, 75 MHz, ppm): δ=107.38 (C$^5$), 115.72 (d, $J_{CF}$=21.9 Hz, C$^{3'}$, C$^{5'}$), 121.47 (C$^\alpha$), 123.15 (C$^1$), 131.00 (d, $J_{CF}$=9.2 Hz, C$^{2'}$, C$^{6'}$), 131.14 (C$^{1'}$), 134.48 (d, $J_{CF}$=2.3 Hz, C$^{1'}$), 135.05 (C$^\beta$), 144.59 (C$^2$), 145.69 (C$^4$), 165.57 (d, $J_{CF}$=253.8 Hz, C$^4$), 188.70 (C=O); IR (ATR, cm$^{-1}$): ν=1158, 1208, 1224, 1316, 1586, 1603 (C=C), 1660 (C=O); MS (ES$^+$): m/z (%): 217.3 ([M+H]$^+$, 100); MP (° C.): 118-119° C.

Yield: 66%, pale-brown crystals.

Compound 78: (2E)-3-(2-Benzofuranyl)-1-(4-fluorphenyl)propenone $^1$H NMR (CDCl$_3$, 300 MHz, ppm): δ=7.05 (s, 1H, H$^7$), 7.19 (dd, 2H, $J_{HF}$=8.5 Hz, $J_{vic}$=8.5 Hz, H$^{3'}$, H$^{5'}$), 7.26 (td, 1H, $J_{vic}$=7.7 Hz, $J_{allyl}$=1.1 Hz, H$^5$), 7.39 (td, 1H, $J_{vic}$=7.7 Hz, $J_{allyl}$=1.1 Hz, H$^4$), 7.52 (br. d, 1H, $J_{vic}$=7.7 Hz, H$^3$), 7.61 (d, 1H, $J_{vic}$=7.7 Hz, H$^6$), 7.67 (d, H, $J_{trans}$=15.1 Hz, H$^\alpha$), 7.73 (d, H, $J_{trans}$=15.1 Hz, H$^\beta$), 8.13 (dd, 2H, $J_{HF}$=5.5 Hz, $J_{vic}$=8.5 Hz, H$^{2'}$, H$^{6'}$); $^{13}$C NMR (CDCl$_3$, 75 MHz, ppm): δ=111.41 (C$^3$), 112.72 (C$^7$), 115.83 (d, $J_{CF}$=21.9 Hz, C$^{3'}$, C$^{5'}$), 121.44 (C$^\alpha$), 121.95 (C$^6$), 123.49 (C$^5$), 126.86 (C$^4$), 128.54 (C$^{6a}$), 131.06 (C$^\beta$), 131.18 (d, $J_{CF}$=9.2 Hz, C$^{2'}$, C$^{6'}$), 134.34 (d, $J_{CF}$=2.3 Hz, C$^{1'}$), 152.97, 155.06 (C$^1$, C$^{2a}$), 165.79 (d, $J_{CF}$=255.0 Hz, C$^4$), 187.87 (C=O); IR (KBr, cm$^{-1}$): ν=1205, 1224, 1267, 1586, 1602 (C=C), 1660 (C=O); MS (ES$^+$): m/z (%): 267.3 ([M+H]$^+$, 100); MP (° C.): 103-104° C.

Yield: 10%, brown crystals.

Compound 79: (2E)-3-(2-Benzofuranyl))-1-(4-methoxyphenyl)propenone $^1$H NMR (CDCl$_3$, 300 MHz, ppm): δ=3.89 (s, 3H, OMe), 6.94-7.03 (m, 3H, H$^7$, H$^{3'}$, H$^{5'}$), 7.25 (t, 1H, $J_{vic}$=8.3 Hz, H$^5$), 7.37 (t, 1H, $J_{vic}$=8.3 Hz, H$^4$), 7.51 (d, 1H, $J_{vic}$=8.3 Hz, H$^3$), 7.60 (d, 1H, $J_{vic}$=8.3 Hz, H$^6$), 7.67 (d, 1H, $J_{trans}$=15.4 Hz, H$^\alpha$), 7.73 (d, 1H, $J_{trans}$=15.4 Hz, Hβ), 8.09 (dt, 2H, $J_{vic}$=8.8 Hz, H2', H6'); $^{13}$C NMR (CDCl$_3$, 75 MHz, ppm): δ=55.57 (OMe), 111.42 (C$^3$), 112.17 (C$^7$), 113.97 (C$^{3'}$, C$^{5'}$), 121.91 (C$^6$, C$^\alpha$), 123.45 (C$^5$), 126.66 (C$^4$), 128.66, (C$^q$), 130.19 (C$^\beta$), 130.98 (C$^{2'}$, C$^{6'}$, C$^q$), 153.30, 155.59 (C$^1$, C$^{2a}$), 163.67 (C$^4$), 187.78 (C=O); IR (ATR, cm$^{-1}$): ν=1257, 1305, 1348, 1448, 1472, 1508, 1545, 1588 (C=C), 1655 (C=O); MS (ES$^+$): m/z (%): 279.3 ([M+H]$^+$, 100); MP (° C.): 124-125° C.

Yield: 82%, pale-yellow crystals.

Compound 81b: 1-[1-(2-propen-1-yl)-1H-indol-3-yl]ethanone $^1$H NMR (CDCl$_3$, 300 MHz, ppm): δ=2.51 (s, 3H, CH$_3$), 4.73 (dt, $J_{vic}$=5.5 Hz, $J_{allyl}$=1.4 Hz, CH$_2$), 5.15 (br. d, 1H, $J_{trans}$=17.2 Hz, =CH$_{cis}\underline{H}_{trans}$), 5.28 (dd, 1H, $J_{cis}$=10.5 Hz, $J_{allyl}$=1.4 Hz, =C$\underline{H}_{cis}$H$_{trans}$), 6.00 (ddt, 1H, $J_{trans}$=17.2 Hz, $J_{cis}$=10.5 Hz, $J_{vic}$=5.5 Hz, NCH$_2$C$\underline{H}$=), 7.23-7.35 (m, 3H, H$^5$, H$^6$, H$^7$), 7.72 (s, 1H, H$^2$), 8.33-8.43 (m, 1H, H$^4$); $^{13}$C NMR (CDCl$_3$, 75 MHz, ppm): δ=27.54 (CH$_3$), 49.27 (CH$_2$), 110.04 (C$^7$), 117.14 (C$^3$), 118.57 (=CH$_2$), 122.53 (br. s, 2×CH), 123.27 (CH), 126.31 (C$^{3a}$), 132.04 (C$^2$), 134.83 ($\underline{C}$H=CH$_2$), 136.82 (C$^{7a}$), 193.00 (C=O); IR (ATR, cm$^{-1}$): ν=1633 (C=O), 1523 (C=C), 1465, 1382, 1193, 926; MS (ES+): m/z (%)=200.1 ([M+H]$^+$, 100), 201.1 ([M+1+H]$^+$, 15), 222.0 ([M+Na]$^+$, 7), 421.1 (8); MP (° C.): 54-55° C.; Yield: 91%.

Compound 81c: 1-[1-(3-methyl-2-buten-1-yl)-1H-indol-3-yl]ethanone $^1$H NMR (CDCl$_3$, 300 MHz, ppm): δ=1.81 (d, 3H, $J_{allyl}$=1.4 Hz, CH$_3$), 1.84 (br. s, 3H, CH$_3$), 2.52 (s, 3H, C(O)CH$_3$), 4.70 (br. d, 2H, $J_{vic}$=7.0 Hz, CH$_2$), 5.39 (txsept, 1H, 7.0 Hz, $J_{allyl}$=1.4 Hz, =C$\underline{H}$(CH$_2$)), 7.24-7.37 (m, 3H, H$^5$, H$^6$, H$^7$), 7.73 (s, 1H, H$^2$), 8.33-8.41 (m, 1H, H$^4$); $^{13}$C NMR (CDCl₃, 75 MHz, ppm): δ=18.14 (CH₃), 25.71 (CH₃), 27.60 (CH₃), 44.66 (CH₂), 109.95 (C⁷), 116.85 (C³), 118.33 (=$\underline{C}$H(CH₂)), 122.45, 122.51, 123.08 (C⁴, C⁵, C⁶), 126.48 (C³ᵃ), 134.34 (C²), 136.80 (=$\underline{C}$(Me)₂), 138.19 (C⁷ᵃ), 192.94 (C=O); IR (ATR, cm⁻¹): ν=1638 (C=O), 1525, 1465, 1382, 1176, 1008, 929, 751; MS (ES⁺): m/z (%)=228.1 ([M+H]⁺, 100), 229.1 ([M+2H]⁺, 15), 477.2 (8); MP (° C.): 63.5-64.5° C.

Yield: 84%.

Compound 82: (2E)-3-(2-Bromophenyl)-1-(1-methyl-1H-indol-3-yl)propenone

¹H NMR (CDCl₃, 300 MHz, ppm): δ=3.87 (s, 3H, NCH₃), 7.18-7.38 (m, 6H, H⁴', H⁵', H⁶', H⁴, H⁵, Hᵅ), 7.63 (dd, 1H, J$_{vic}$=7.7 Hz, J$_{allyl}$=1.7 Hz, C³'), 7.71 (dd, 1H, J$_{vic}$=8.0 Hz, J$_{allyl}$=1.7 Hz, C⁶'), 7.83 (s, 1H, H²), 8.11 (d, 1H, 15.4 Hz, Hᵝ), 8.48-8.56 (m, 1H, H⁷); ¹³C NMR (CDCl₃, 75 MHz, ppm): δ=33.57 (NCH₃), 109.70 (C⁴), 117.26 (C¹'), 122.74, 122.89, 123.67 (C⁵', C⁶', C⁷'), 125.53 (C¹), 126.73 (C⁷ᵃ), 126.85 (Cᵅ), 127.57, 127.66 (C⁵, C⁶), 130.65 (C⁴'), 133.37 (C³'), 135.46 (Cᑫ), 135.76 (C²'), 137.57 (Cᑫ), 139.29 (Cᵝ), 183.97 (C=O); IR (ATR, cm⁻¹): ν=1643 (C=O), 1588, 1525, 1466, 1370, 1088, 962; MS (ES+): m/z (%)=340.0 ([M−2+H]⁺, 94), 341.3 ([M−1+H]⁺, 15), 342.0 ([M+H]⁺, 100), 343.0 ([M+1+H]⁺, 23); MP (° C.): 154-155° C.

Yield: 67%.

Compound 83: (2E)-3-(4-Bromophenyl)-1-(1-methyl-1H-indol-3-yl)propenone

¹H NMR (CDCl₃, 300 MHz, ppm): δ=3.83 (s, 3H, NCH₃), 7.25-7.37 (m, 4H, H⁴', H⁵', H⁶', Hᵅ), 7.46 (d, 2H, 8.5 Hz, C², C⁶), 7.51 (d, 2H, J$_{vic}$=8.5 Hz, C³, C⁵), 7.70 (d, 1H, 16.0 Hz, Hᵝ), 7.81 (s, 1H, H²), 8.44-8.55 (m, 1H, H⁷); ¹³C NMR (CDCl₃, 75 MHz, ppm): δ=33.48 (NCH₃), 109.70 (C⁴), 117.37 (C¹), 122.69, 122.86 (C⁷', Cᵅ), 123.64 (CH), 123.84 (C⁴), 124.24 (CH), 126.68 (C⁷ᵃ), 129.44 (C², C⁶), 131.95 (C³, C⁵), 134.18 (C¹), 135.58 (C²'), 137.52 (C³ᵃ), 139.35 (Cᵝ), 183.74 (C=O); IR (ATR, cm⁻¹): ν=1648 (C=O), 1589, 1574, 1527, 1485, 1466, 1375; MS (ES+): m/z (%)=340.0 ([M+H]⁺, 100), 341.0 ([M+1+H]⁺, 19), 342.0 ([M+2+H]⁺, 95), 343.0 ([M+3+H]⁺, 18); MP (° C.): 180-181° C.

Yield: 83%.

Compound 84: (2E)-3-(4-Chlorophenyl))-1-(1-allyl-1H-indol-3-yl)propenone

¹H NMR (CDCl₃, 300 MHz, ppm): δ=4.77 (dt, 2H, J$_{vic}$=5.5 Hz, J$_{allyl}$=1.4 Hz), 5.18 (dd, 1H, J$_{trans}$=17.6 Hz, J$_{allyl}$=1.4 Hz, =CH$_{cis}$$\underline{H}_{trans}$), 5.31 (dd, 1H, J$_{cis}$=10.5 Hz, J$_{allyl}$=1.4 Hz, =$\underline{H}_{cis}$H$_{trans}$), 6.02 (ddt, 1H, J$_{trans}$=17.6 Hz, J$_{cis}$=10.5 Hz, J$_{vic}$=5.5 Hz, NCH₂$\underline{C}$H=), 7.25-7.38 (m, 6H, H², H⁶, H⁴', H⁵', H⁶', Hᵅ), 7.54 (d, 2H, J$_{vic}$=8.3 Hz, H³, H⁵) 7.74 (d, 1H, J$_{vic}$=16.0 Hz, Hᵝ), 7.87 (s, 1H, H²), 8.49-8.56 (m, 1H, H⁷); ¹³C NMR (CDCl₃, 75 MHz, ppm): δ=49.45 (NCH₂), 110.10 (C⁴), 117.89 (C¹), 118.83 (=CH₂), 122.83 (CH), 123.06 (C⁷'), 123.75 (CH), 124.22 (Cᵅ), 126.89 (C⁷ᵃ), 129.06 (C², C⁶), 129.29 (C³, C⁵), 131.93 (NCH₂$\underline{C}$H=), 133.84 (Cᑫ), 134.45 (C²'), 135.58 (Cᑫ), 137.02 (C³ᵃ), 139.60 (Cᵝ), 183.98 (C=O); IR (ATR, cm⁻¹): ν=1637 (C=O), 1572, 1560, 1515, 1491, 1463, 1381, 1185; MS (ES⁺): m/z (%)=322.3 ([M+H]⁺, 100), 324.2 ([M+2H]⁺, 28); MP (° C.): 149° C.

Yield: 62%.

Compound 85: (2E)-3-(4-Chlorophenyl)-1-[1-(3-methylbut-2-enyl)-1H-indol-3-yl]propenone ¹H NMR (CDCl₃, 300 MHz, ppm): δ=1.83 (br. s, 3H, CH₃), 1.87 (br. s, 3H, CH₃), 4.76 (br. d, 2H, J$_{vic}$=7.2 Hz, CH₂), 5.42 (t×sept, 1H, J$_{gem}$=7.2 Hz, J$_{allyl}$=1.1 Hz, CH=), 7.30-7.41 (m, 6H, H², H⁶, H⁴', H⁵', H⁶', Hᵅ), 7.57 (d, 2H, J$_{vic}$=8.8 Hz, H³, H⁵) 7.76 (d, 1H, J$_{vic}$=16.0 Hz, Hᵝ), 7.89 (s, 1H, H²), 8.47-8.56 (m, 1H, H⁷); ¹³C NMR (CDCl₃, 75 MHz, ppm): δ=18.23 (CH₃), 25.76 (CH₃), 44.90 (NCH₂), 110.05 (C⁴), 117.58 (C¹), 118.30 (NCH₂$\underline{C}$H=), 122.77, 123.05, 123.56, 124.37 (C⁵', C⁶', C⁷', Cᵅ), 127.06 (C⁷ᵃ), 129.05 (C², C⁶), 129.31 (C³, C⁵), 133.95 (Cᑫ), 134.07 (NCH=), 135.52 (Cᑫ), 137.02 (=$\underline{C}$(CH₃)₂), 138.31 (C³ᵃ), 139.46 (Cᵝ), 183.90 (C=O); IR (ATR, cm⁻¹): ν=1642 (C=O), 1580, 1572, 1565, 1519, 1488, 1463, 1384; MS (ES+): m/z (%)=350.3 ([M+H]⁺, 100), 351.2 ([M+1+H]⁺, 21), 352.3 ([M+2+H]⁺, 26); MP (° C.): 203-204° C.

Yield: 54%.

Compound 86: (2E)-3-(4-Fluorophenyl)-1-[1-(3-methylbut-2-enyl)-1H-indol-3-yl]propenone ¹H NMR (CDCl₃, 300 MHz, ppm): δ=1.82 (br. s, 3H, CH₃), 1.86 (br. s, 3H, CH₃), 4.74 (br. d, 2H, J$_{vic}$=6.8 Hz, CH₂), 5.42 (br. t, 1H, J$_{gem}$=6.8 Hz, CH=), 7.08 (t, 2H, J$_{vic}$=8.5 Hz, J$_{HF}$=8.5 Hz, H³, H⁵), 7.23-7.40 (m, 4H, H⁴', H⁵', H⁶', Hᵅ), 7.61 (dd, 2H, J$_{vic}$=8.5 Hz, J$_{HF}$=5.5 Hz, H², H⁶), 7.77 (d, 1H, J$_{vic}$=15.4 Hz, Hᵝ), 7.87 (s, 1H, H²), 8.49-8.57 (m, 1H, H⁷); ¹³C NMR (CDCl₃, 75 MHz, ppm): δ=18.21 (CH₃), 25.76 (CH₃), 44.90 (NCH₂), 110.04 (C⁴), 115.94 (d, J$_{CF}$=21.9 Hz, C³, C⁵), 117.67 (C¹'), 118.39 (NCH₂$\underline{C}$H=), 122.76, 123.12, 123.55, 123.73 (C⁵', C⁶', C⁷', Cᵅ), 127.15 (C⁷ᵃ), 129.95 (d, J$_{CF}$=8.1 Hz, C², C⁶), 131.73 (C¹), 133.95 (C²'), 137.06, 138.28 (C³ᵃ, =$\underline{C}$(CH₃)₂), 139.69 (Cᵝ), 163.65 (d, J$_{CF}$=250.4 Hz, C⁴), 184.07 (C=O); IR (ATR, cm⁻¹): ν=1643 (C=O), 1588, 1572, 1525, 1466, 1463, 1370, 1089, 962; MS (ES+): m/z (%)=334.3 ([M+H]⁺, 100), 335.3 ([M+1+H]⁺, 22); MP (° C.): 146.5-147.5° C.

Yield: 49%.

Compound 87: (2E)-3-(2-Fluorophenyl)-1-[1-(3-methylbut-2-enyl)-1H-indol-3-yl]propenone ¹H NMR (CDCl₃, 300 MHz, ppm): δ=1.83 (br. s, 3H, CH₃), 1.87 (br. s, 3H, CH₃), 4.77 (br. d, 2H, J$_{vic}$=6.8 Hz, CH₂), 5.43 (br. t, 1H, J$_{gem}$=6.8 Hz, CH=), 7.08-7.23 (m, 2H, 2×CH), 7.29-7.41 (m, 4H, 4×CH), 7.51 (d, 1H, J$_{vic}$=15.7 Hz, Hᵅ), 7.65 (td, 1H, J$_{vic}$=7.6 Hz, J$_{allyl}$=1.3 Hz, CH), 7.89 (d, 1H, J$_{vic}$=15.7 Hz, Hᵝ), 7.89 (s, 1H, H²), 8.48-8.58 (m, 1H, H⁷); ¹³C NMR (CDCl₃, 75 MHz, ppm): δ=18.20 (CH₃), 25.73 (CH₃), 44.89 (NCH₂), 110.02 (C⁴), 116.17 (d, J$_{CF}$=21.9 Hz, C³), 117.61 (C¹), 118.34 (NCH₂$\underline{C}$H=), 123.52, (C⁵', C⁶', C⁷'), 123.63 (Cᵅ), 124.38 (d, J$_{CF}$=3.5 Hz, C⁵), 126.82 (d, J$_{CF}$=6.9 Hz, C¹), 127.12 (C⁷ᵃ), 129.85 (d, J$_{CF}$=3.5 Hz, C⁶), 130.97 (d, J$_{CF}$=9.2 Hz, C⁴), 133.84 (C²'), 134.22 (Cᵝ), 137.05, 138.31 (C³ᵃ, =$\underline{C}$(CH₃)₂), 161.61 (d, J$_{CF}$=253.8 Hz, C²), 184.29 (C=O); ¹⁹F NMR (CDCl₃, 282 MHz, ppm): δ=(−)113.9-(−)113.3 (m); IR (ATR, cm⁻¹): ν=1641 (C=O), 1571 (C=C), 1519, 1486, 1463, 1381, 1060, 957, 751, 748, 736; MS (ES+): m/z (%)=334.3 ([M+H]⁺, 100), 335.3 ([M+1+H]⁺, 34); MP (° C.): 136-137° C.

Yield: 14%.

Compound 90: (E)-4,4'-Difluorostilbene

¹H NMR (CDCl₃, 300 MHz, ppm): δ=6.98 (s, 2H, Hᵅ, Hᵝ), 7.05 (dd, 4H, J$_{HF}$=8.8 Hz, J$_{vic}$=8.8 Hz, H³, H⁵, H³', H⁵'), 7.46

(dd, 4H, $J_{HF}$=5.5 Hz, $J_{vic}$=8.8 Hz, H², H⁶, H²', H⁶'); ¹³C NMR (CDCl₃, 75 MHz, ppm): δ=116.32 (d, $J_{CF}$=21.9 Hz, C³, C⁵, C³', C⁵'), 128.18 (Cᵅ, Cᵝ), 129.15 (d, $J_{CF}$=8.1 Hz, C², C⁶, C²', C⁶'), 134.81 (d, $J_{CF}$=3.5 Hz, C¹, C¹'), 163.17 (d, $J_{CF}$=244.6 Hz, C⁴); IR (ATR, cm⁻¹): ν=1205, 1230, 1255, 1506, 1599; MS (ES⁺): m/z (%): 216 ([M+H]⁺, 100); MP (° C.): 116-117° C.

Yield=48% (purity 92%, GC); yellow-brown crystals.

Compound 91:
1-fluoro-4-[(E)-2-(4-methoxyphenyl)ethenyl]benzene

This molecule has been reported by Loska et al, 2008

Compound 92:
1-fluoro-4-[(Z)-2-phenylethenyl]benzene

This molecule has been reported by Sun et al, 2007

Compound 93: (Z)-3,4,5-Trimethoxystilbene

¹H NMR (CDCl₃, 300 MHz, ppm): δ=3.64 (s, 6H, C³OMe, C⁵OMe), 3.83 (s, 3H, C⁴OMe), 6.46 (s, 2H, H², H⁶), 6.49 (d, 1H, $J_{cis}$=12.1 Hz, CH), 6.59 (d, 1H, $J_{cis}$=12.1 Hz, CH), 7.14-7.38 (m, 5H, H²', H³', H⁴', H⁵', H⁶'); ¹³C NMR (CDCl₃, 75 MHz, ppm): δ=55.77 (C³OMe, C⁵OMe), 60.87 (C⁴OMe), 106.04 (C², C⁶), 127.12 (C⁴'), 128.24 (C²', C⁶'), 128.89 (C³', C⁵'), 129.96 (CH), 130.10 (CH), 132.44 (C¹), 137.14 (C⁴), 137.44 (C¹'), 152.82 (C³, C⁵); IR (ATR, cm⁻¹): ν=1123, 1236, 1327, 1403, 1420, 1451, 1462, 1505, 1579; MS (ES⁺): m/z (%): 271.3 ([M+H]⁺, 100).

Yield=13%; yellow oil; Chromatography: Rf=0.72 (petroleum ether/EtOAc 1:1).

Compound 94:
(Z)-4'-Fluoro-3,4,5-trimethoxystilbene

The mixture of (E)- and (Z)-37 was separated by means of preparative TLC using an eluent mixture of petroleum ether and Et₂O (1:1).

¹H NMR (CDCl₃, 300 MHz, ppm): δ=3.67 (6H, s, 2×OCH₃), 3.83 (3H, s, OCH₃), 6.45 (2H, s, H², H⁶), 6.48 (1H, d, $J_{cis}$=12.4 Hz, CH), 6.54 (1H, d, $J_{cis}$=12.4 Hz, CH), 6.94 (2H, dd, $J_{HF}$=8.8 Hz, $J_{vic}$=8.8 Hz, H³', H⁵'), 7.26 (2H, dd, $J_{vic}$=8.8 Hz, $J_{HF}$=5.5 Hz, H²', H⁶'); ¹³C NMR (CDCl₃, 75 MHz, ppm): δ=55.85 (2×OCH₃), 60.92 (OCH₃), 105.94 (C², C⁶), 115.13 (d, $J_{CF}$=21.9 Hz, C³', C⁵'), 128.74 (CH), 130.15 (CH), 130.66 (d, $J_{CF}$=8.1 Hz, C²', C⁶'), 132.28 (C¹), 133.31 (d, $J_{CF}$=3.5 Hz, C¹'), 137.23 (C⁴), 152.96 (C³, C⁵), 161.81 (d, $J_{CF}$=246.9 Hz, C⁴'); IR (ATR, cm⁻¹): ν=1127, 1233, 1327, 1411, 1421, 1452, 1462, 1506, 1578; MS (ES⁺): m/z (%): 289.2 ([M+H]⁺, 100).

Yield=43%; yellow oil; Chromatography: Rf=0.83 (petroleum ether/Et₂O 1:1); MW=288.31.

Compound 95: 1,1'-(E)-ethene-1,2-diyldibenzene

This molecule has been reported by Bandari et al., 2010

Compound 96:
1,2,3-trimethoxy-5-[(E)-2-phenylethenyl]benzene

This molecule has been reported by Alonso et al., 2011. This substance was separated from its (Z)-isomer via preparative TLC.

Compound 97: (E)-3-Fluorstilbene

¹H NMR (CDCl₃, 300 MHz, ppm): δ=6.95 (ddd, 1H, $J_{vic}$=8.3 Hz, $J_{HF}$=8.3 Hz, $J_{allyl}$=1.7 Hz, H⁴), 7.05 (d, 1H, $J_{trans}$=16.0 Hz, CH), 7.12 (d, 1H, $J_{trans}$=16.0 Hz, CH), 7.22 (dt, 1H, $J_{HF}$=10.0 Hz, $J_{allyl}$=1.6 Hz, H²), 7.26-7.33 (m, 3H, H⁵, H⁶, H⁴'), 7.37 (dt, 2H, $J_{vic}$=7.4 Hz, $J_{allyl}$=1.7 Hz, H³', H⁵'), 7.51 (dd, 2H, $J_{vic}$=7.4 Hz, $J_{allyl}$=1.7 Hz, H²', H⁶'); ¹³C NMR (CDCl₃, 75 MHz, ppm): δ=112.76 (d, $J_{CF}$=21.9 Hz, C²), 114.38 (d, $J_{CF}$=21.9 Hz, C⁴), 122.45 (d, $J_{CF}$=2.3 Hz, C⁶), 126.65 (C²', C⁶'), 127.47 (d, $J_{CF}$=2.3 Hz, Cᵅ), 128.01 (Cᵝ), 128.74 (C³', C⁵'), 130.01, 130.15 (C⁴', C⁵), 136.82 (C¹'), 139.70 (d, $J_{CF}$=6.9 Hz, C¹), 163.19 (d, $J_{CF}$=245.8 Hz, C³); IR (ATR, cm⁻¹): ν=1266, 1447, 1466, 1484, 1495, 1580, 1606; MS (ES⁺): m/z (%): 198 ([M+H]⁺, 100); MP (° C.): 75-76° C.

Yield=79%, white crystals.

Compound 98: (E)-3,4'-Difluorostilbene

¹H NMR (Acetone-d₆, 300 MHz, ppm): δ=6.98-7.09 (m, 1H, H³), 7.17 (dd, 4H, $J_{HF}$=8.8 Hz, $J_{Hvic}$=8.8 Hz, H³', H⁵'), 7.22 (d, 1H, $J_{trans}$=16.2 Hz, CH), 7.34 (d, 1H, $J_{trans}$=16.2 Hz, CH), 7.37-7.42 (m, 3H, H², H⁵, H⁶), 7.68 (dd, 2H, $J_{HF}$=5.5 Hz, $J_{Hvic}$=8.8 Hz, H²', H⁶'); ¹³C NMR (CDCl₃, 75 MHz, ppm): δ=112.72 (d, $J_{CF}$=21.9 Hz, C²), 114.44 (d, $J_{CF}$=21.9 Hz, C⁴), 115.72 (d, $J_{CF}$=21.9 Hz, C³', C⁵'), 122.40 (d, $J_{CF}$=2.3 Hz, C⁶), 127.27 (=CH), 128.18 (d, $J_{CF}$=8.1 Hz, C²', C⁶'), 128.80 (=CH), 130.14 (d, $J_{CF}$=8.1 Hz, C⁵), 133.02 (d, $J_{CF}$=3.5 Hz, C¹'), 139.54 (d, $J_{CF}$=8.1 Hz, C¹), 162.55 (d, $J_{CF}$=244.6 Hz, C⁴'), 163.20 (d, $J_{CF}$=248.1 Hz, C³); IR (ATR, cm⁻¹): ν=1217, 1228, 1266, 1444, 1482, 1507, 1578, 1597; MS (ES⁺): m/z (%): 216 ([M+H]⁺, 100); MP (° C.): 92-93° C.

Yield=99%; white crystals.

Compound 99: (E)-4'-Chloro-3-methoxystilbene

¹H NMR (CDCl₃, 300 MHz, ppm): δ=3.83 (s, 3H, OMe), 6.82 (dd, 1H, $J_{vic}$=7.7 Hz, $J_{allyl}$=2.6 Hz, H⁴), 6.97-7.09 (m, 3H, H², Hᵅ, Hᵝ), 7.09 (d, 1H, $J_{vic}$=7.7 Hz, H⁶), 7.27 (t, 1H, $J_{vic}$=7.7 Hz, H⁵), 7.31 (d, 2H, $J_{vic}$=8.5 Hz, H³', H⁵'), 7.42 (d, 2H, $J_{vic}$=8.5 Hz, H²', H⁶'); ¹³C NMR (CDCl₃, 75 MHz, ppm): δ=55.36 (OMe), 111.91 (C²), 113.62 (C⁴), 119.38 (C⁶), 127.78 (br. s, C²', C⁶', CH), 128.96 (br. s, C³', C⁵'), 129.30 (CH), 129.82 (br. s, C⁵), 133.33, 135.84, 138.52 (C¹, C¹', C⁴'), 160.02 (C³); IR (ATR, cm⁻¹): ν=1251, 1269, 1431, 1444, 1575, 1604; MS (ES⁺): m/z (%): 245.2 ([M+H]⁺, 100) en 247.2 ([M+2+H]⁺, 35); MP (° C.): 71-72° C.

Yield=95%; white crystals.

Compound 100:
(E)-4'-Fluoro-3,4,5-trimethoxystilbene

This substance was separated from its (Z)-isomer via preparative TLC.

¹H NMR (CDCl₃, 300 MHz, ppm): δ=3.87 (s, 3H, C⁴OMe), 3.92 (s, 6H, C³OMe, C⁵OMe), 6.72 (s, 2H, H², H⁶), 6.93 (d, 1H, $J_{trans}$=16.5 Hz, =CH), 6.99 (d, 1H, $J_{trans}$=16.5 Hz, =CH), 7.05 (dd, 2H, $J_{HF}$=8.8 Hz, $J_{Hvic}$=8.8 Hz, H³', H⁵'), 7.47 (dd, 2H, $J_{Hvic}$=8.9 Hz, $J_{HF}$=5.0 Hz, H²', H⁶'); ¹³C NMR (CDCl₃, 75 MHz, ppm): δ=56.11 (C³OMe, C⁵OMe), 60.98 (C⁴OMe), 103.49 (C², C⁶), 115.65 (d, $J_{CF}$=21.9 Hz, C³', C⁵'), 126.98 (=CH), 127.89 (d, $J_{CF}$=8.1 Hz, C²', C⁶'), 128.44 (=CH), 132.94 (C¹), 133.39 (d, $J_{CF}$=3.5 Hz, C¹'), 137.93 (C⁴), 153.41 (C³, C⁵), 162.30 (d, $J_{CF}$=246.9 Hz, C⁴'); IR (ATR, cm⁻¹): ν=1128, 1152, 1225, 1239, 1334, 1521, 1449, 1508, 1582; MS (ES⁺): m/z (%): 289.2 ([M+H]⁺, 100).

Yield=3%; yellow oil; Chromatography: Rf=0.69 (petroleum ether/EtOAc 1:1).

B. Compound Synthesis

B.1. Reaction Procedures for the Synthesis of Chalcones

Preparation of Chalcones Via Claisen-Schmidt Condensation.

A solution of the acetophenone (10 mmol) and LiOH.H$_2$O (10 mol %) in 10 mL of absolute ethanol is stirred at the appropriate temperature for 10 min (for reactions at 40° C., the bulb is equipped with a reflux condenser). Then, the benzaldehyde (10 mmol, 1 equiv.) is added and the system is protected from the atmosphere with a cork stopper. Reaction progress is monitored by TLC or LCMS-analysis; during the course of the reaction, the chalcone may precipitate. Upon attaining maximum conversion grade, the reaction mixture is quenched with 15 mL of 1% hydrochloric acid.

If the chalcone has precipitated, it is isolated by means of filtration. In order to remove residual amounts of benzaldehyde, the residue is washed thoroughly with water until the filtrate turns clear. The obtained solid is the chalcone, which can be dried in a dessicator. Subsequently, the chalcone can be recrystallized in absolute ethanol so as to obtain high purity crystals.

If the chalcone has formed a separate oily liquor at the bottom of the bulb, it can be extracted from the mixture with diethyl ether. The organic phase is subsequently washed with brine (2×) and dried over MgSO$_4$, upon which the solution is concentrated in vacuo. Again, purification of the thus obtained residue can be performed through recrystallization in absolute ethanol.

BBr$_3$-Mediated Demethylation of Methoxychalcones.

Warning—boron tribromide is toxic, corrosive and extremely reactive when in contact with air or water. A flame-dried 10 mL microwave vial is loaded with the methoxychalcone (0.4 mmol) and 7 mL of dry dichloromethane. The headspace is subsequently flushed with nitrogen gas, while the boron tribromide (3 equiv., 1.2 mmol, or 4 equiv. for dimethoxychalcones) is quickly added under the liquid surface with a syringe. The vial is subsequently sealed with a Teflon® cap and introduced into the microwave apparatus. The target temperature is set at 55° C. (ramp of 5 min) and the reaction time at 30 min; magnetic stirring is turned on, 'powermax' is turned off.

Upon completion of the reaction, the mixture is poured into an Erlenmeyer flask of 50 mL, to which water is added dropwise until all excess BBr$_3$ is destroyed. The contents of the flask is transferred into a separating funnel, to which 20 mL of a 1 N aqueous sodium hydroxide solution and 20 mL of diethyl ether are added. Upon vigorous shaking, the intensely yellow (or red in case of a dihydroxychalcone) water layer is isolated and acidified with 3 N hydrochloric acid. The hydroxychalcone is extracted from the resulting cloudy suspension with an equal volume of diethyl ether (2×). The organic phase is subsequently isolated and dried over MgSO$_4$, upon which the solvent is evaporated, furnishing the hydroxychalcone as a solid, reddish brown powder.

O-Prenylation of Hydroxychalcones.

To a solution of the hydroxychalcone (2 mmol) in acetone (4 mL) are added prenyl bromide (6 mmol, 3 equiv.), sodium iodide (6 mmol, 3 equiv.) and potassium carbonate (14 mmol, 7 equiv.). The resulting suspension is heated to reflux temperature under magnetic stirring for 4 hours (reaction progress is verified by TLC analysis). Then, the mixture is poured into a larger volume of diethyl ether, and the insoluble salts are removed via filtration. Concentration of the filtrate in vacuo furnishes the O-prenylated chalcone in all but quantitative yield.

The synthesis of compounds 37-51 was conducted via a Claisen-Schmidt condensation of suitably functionalized acetophenones and benzaldehydes. Whilst other syntheses have been proposed to prepare chalcones (e.g. via 1,3-diaryl-1-siloxy allenes or by Suzuki or Heck coupling reactions), this crossed aldol condensation remains the method of choice, given its simplicity and the ready availability of the required acetophenones 35 and benzaldehydes 36.

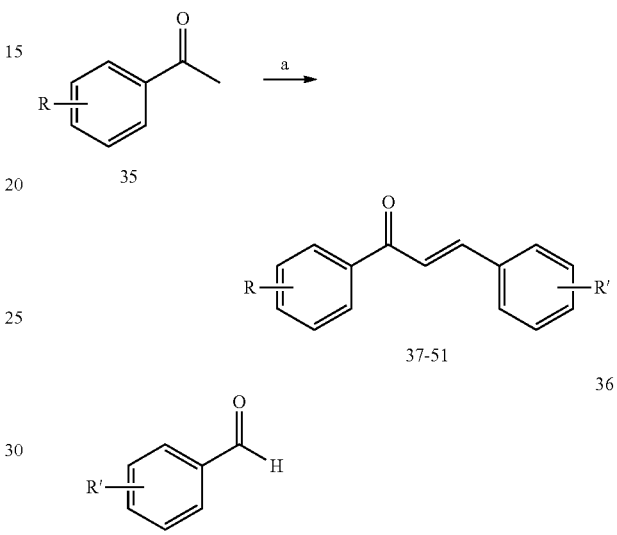

Wherein R and R' are as represented in table 3
Scheme:
Chalcone synthesis. a) 1 equiv. benzaldehyde 36, 5 mol % LiOH.H$_2$O, abs. EtOH., conditions see table 3.

Over the years, numerous basic (e.g. NaOH, Ba(OH)$_2$ and Al$_2$O$_3$) and acid (e.g. dry HCl and BF$_3$) catalysts have been proposed for this transformation. We considered the LiOH.H$_2$O catalyzed protocol as proposed by Bhagat and co-workers to be the most elegant, because of its high catalyst turnover and yields, short reaction times and easy work-up. Nevertheless, as we could only obtain the high yields reported by these researchers after prolonged reaction times, we evaluated the influence of the reaction temperature on its outcome. As such, by rising the temperature to 40 or 70° C., and by optimizing the work-up procedure, we were able to obtain the pure chalcones 37-51 in reasonable to excellent yield after crystallization in ethanol (see table 3).

TABLE 3

Synthesis conditions and yield for the synthetic chalcones 37-51 in the training set.

| | | Reaction conditions | | |
|---|---|---|---|---|
| R | R' | Temperature[a] (° C.) | Time (h) | Yield[b] (%) |
| 37 H | H | 20 | .83 | 74 |
| 38 4'-MeO | H | 20 | 2 | 80 |
| 39 H | 4-MeO | 20 | 3 | 77 |
| 40 4'-MeO | 4-MeO | 40 | 2 | 82 |
| 41 4'-MeO | 3-MeO | 20 | 1 | 62 |
| 42 2',4',6'-triMeO | 2,4,5-triMeO | 20 | 168 | 78 |
| 43 2',4',6'-triMeO | 4-MeO | 20 | 86 | 69 |

TABLE 3-continued

Synthesis conditions and yield for the synthetic chalcones 37-51 in the training set.

| | R | R' | Temperature$^a$ (°C.) | Time (h) | Yield$^b$ (%) |
|---|---|---|---|---|---|
| 44 | 4'-MeO | 2,4,5-triMeO | 20 | 15 | 92 |
| 45 | 4'-MeO | 2,4,6-triMeO | 70 | 2 | 89 |
| 46 | 2',6'-diMeO | 2,4,5-triMeO | 40 | 5.5 | 62 |
| 47 | 2',6'-diMeO | 2,4,6-triMeO | 40 | 48 | 64 |
| 48 | 4'-MeO | 4-F | 20 | 4 | 91 |
| 49 | 3',4',5'-triMeO | 4-F | 20 | 24 | 69 |
| 50 | 4'-F | 4-F | 20 | 1 | 42 |
| 51 | H | 4-F | 40 | 2 | 51 |

The synthesis of compounds 52-55 was conducted in a similar way as described above for compounds 37-51, and the synthesis conditions are as depicted in table 4.

TABLE 4

Synthesis conditions and yield for the synthetic chalcones 52-55.

| | R | R' | Conditions | Yield$^a$ (%) |
|---|---|---|---|---|
| 52 | 4'-MeO | 4-Cl | r.t., 2 h | 85 |
| 53 | 4'-F | 3-F | r.t., 1 h 15 min | 70 |
| 54 | 4'-MeO | 3-F | r.t., 30 min | 76 |
| 55 | 4'-MeO | 2-F | r.t., 4 h | 88 |

$^a$Yield of the pure chalcone upon recrystallization in absolute EtOH.

The synthesis of compounds 56-65 was conducted as schematically represented in the below scheme, and for compounds 56-59 represented in table 5.

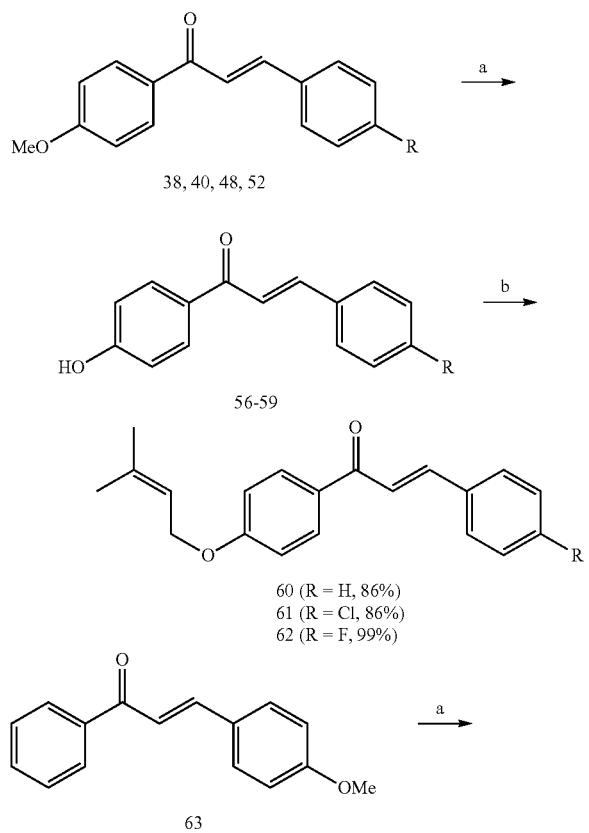

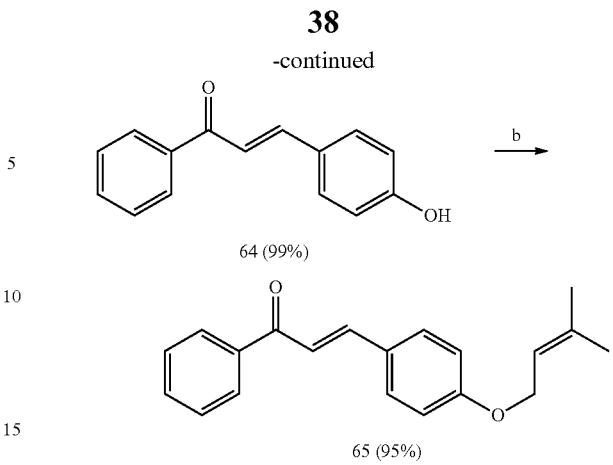

wherein R is as represented in table 5

Scheme:

Synthesis of hydroxy- and prenyloxychalcones. a) BBr$_3$, dry CH$_2$Cl$_2$, microwave, 55° C., 30 min) 3 equiv. RBr, 3 equiv. NaI, 7 equiv. K$_2$CO$_3$, acetone, D, 4 h. Reaction conditions, see table 5.

TABLE 5

Synthesis of hydroxychalcones 56-59 via BBr$_3$-mediated demethylation of methoxychalcones 38, 52, 48 and 40 respectively.

| Substrate | R | equiv. BBr$_3$ | Product | R | Yield$^a$ (%) |
|---|---|---|---|---|---|
| 38 | H | 3 | 56 | H | 99 |
| 52 | Cl | 3 | 57 | Cl | 99 |
| 48 | F | 3 | 58 | F | 83 |
| 40 | OMe | 4 | 59 | OH | 99 |

$^a$Yield of the pure hydroxychalcone upon extraction.

The synthesis of compounds 68-70 and 72-79 was conducted as schematically represented below and further detailed in table 6.

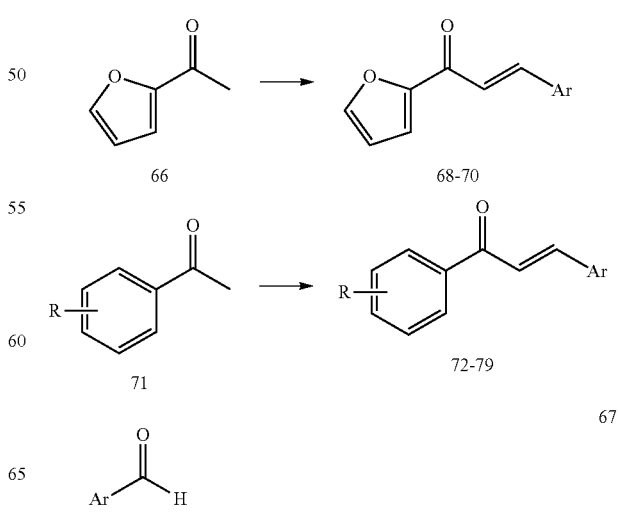

-continued

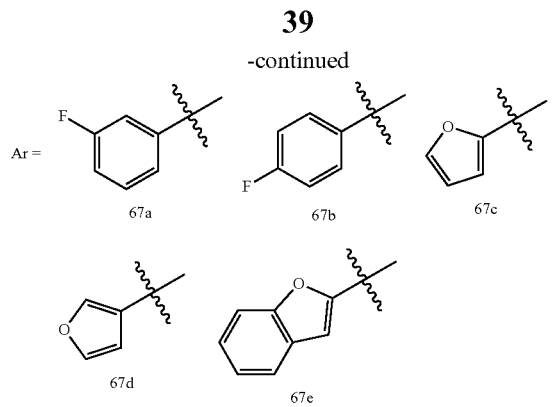

wherein R is as represented in table 6.
Scheme:
Synthesis of furyl chalcones. 1 equiv. aldehyde, 10 mol % LiOH.H$_2$O, abs. EtOH, 40° C., Reaction conditions see table 6

TABLE 6

Synthesis of furyl chalcones 68-70 and 72-79.

|    | R              | Aldehyde | Time (h) | Yield (%) |
|----|----------------|----------|----------|-----------|
| 68 | —              | 67a      | 7        | 76        |
| 69 | —              | 67b      | 7        | 15[a]     |
| 70 | —              | 67c      | 6        | 91[a]     |
| 72 | H              | 67c      | 70       | 94        |
| 73 | 4'-F           | 67c      | 5        | 82        |
| 74 | 4'-MeO         | 67c      | 5        | 98        |
| 75 | 3',4',5'-triMeO| 67c      | 5        | 56[a]     |
| 76 | 2',6'-diMeO    | 67c      | 76       | 31[b]     |
| 77 | 4'-F           | 67d      | 19       | 30[a]     |
| 78 | 4'-F           | 67e      | 20       | 10        |
| 79 | 4'-MeO         | 67e      | 18       | 82        |

[a]Yield of the pure furyl chalcone upon recrystallization in EtOH.
[b]Upon recrystallization in MeOH.

The synthesis of compounds 82-87 was conducted as schematically represented below, and detailed in table 7.

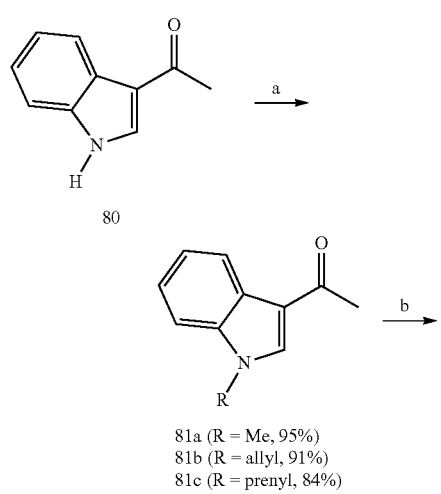

81a (R = Me, 95%)
81b (R = allyl, 91%)
81c (R = prenyl, 84%)

-continued

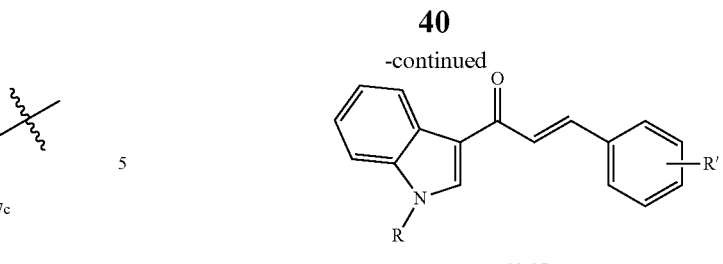

82-87 wherein R and R' are as represented in table 7
Scheme:
Synthesis of indolylchalcones. a) 1 equiv. R$^1$X, 1.5 mol % (nBu)$_4$N$^+$Br$^-$, 25% NaOH$_{(aq)}$/mTHF (3:2), Δ, 3.5 h; b) 1 equiv. benzaldehyde, 5 mol % LiOH.H$_2$O, abs. EtOH. Reaction conditions see table 7

N-Alkylation of 3-Acetylindole: Synthesis of Compounds 81a-c.

A mixture of 3-acetylindole (6.32 mmol, 1 g), tetra-n-butylammonium bromide (1.5 mol %) and the alkyl halide (1 equiv., 6.32 mmol) in 6 mL of 2-methyltetrahydrofuran and 8 mL of a 25% aqueous sodium hydroxide solution is heated to reflux temperature for 3.5 hours (reaction progress is also monitored by TLC analysis). Afterward, the contents of the flask is allowed to cool to room temperature, while it separates into two layers. Diethyl ether is added (10 mL) and the mixture is transferred into a separation funnel. The organic phase is isolated and dried over MgSO$_4$, whereupon the solvent is evaporated in vacuo, furnishing the N-alkylated indole as a white solid.

TABLE 7

Synthesis of indolylchalcones 80-86: outcome of the Claisen-Schmidt condensation.

|    | R      | R'   | Temp. (° C.) | Time (h) | Yield[a] (%) |
|----|--------|------|--------------|----------|--------------|
| 82 | Me     | 2-Br | 40           | 45       | 67           |
| 83 | Me     | 4-Br | 40           | 45       | 83           |
| 84 | allyl  | 4-Cl | 40           | 8        | 62           |
| 85 | prenyl | 4-Cl | 40           | 18       | 54           |
| 86 | prenyl | 4-F  | 40           | 77       | 49           |
| 87 | prenyl | 2-F  | 40           | 5        | 14           |

[a]Yield of the pure products upon crystallization in EtOH.

B.2. Reaction Procedures for the Synthesis of Stilbenes

Preparation of Stilbenes 90 and 91 Via Horner-Wadsworth-Emmons Reaction.

A mixture of a suitable benzyl bromide (1 mmol) and excess triethyl phosphite are stirred at 130° C. for 20 h. Removal of the remaining phosphite by vacuum distillation furnishes the desired phosphonate as the residue. This intermediate is dissolved in 2 mL of dry dimethylformamide, contained in a flame-dried round-bottomed flask under a nitrogen atmosphere. Next, a solution of sodium methoxide (0.73 equiv.) in methanol is added dropwise. The contents of the flask is cooled to 0° C., upon which the aldehyde (0.67 equiv.) is added. The resulting mixture is then successively stirred at room temperature for 1 h, heated to reflux temperature for another hour and left standing overnight. Afterward, a mixture of water and methanol (1:1) is added, which provides the desired stilbene as a precipitate. A second crop of crystals can be harvested from the mother liquor.

Synthesis of 1,2-Diarylacetylenes Via Sonogashira-Coupling.

A round-bottomed flask is loaded with $PdCl_2(PPh_3)_2$ (0.02 mmol, 2 mol %) and thoroughly flushed with argon. sec-Butylamine (0.5 mL), water (0.5 mL), the aryl iodide (1 mmol) and the acetylene (1.3 mmol, 1.3 equiv) are added respectively, after which the headspace is flushed with argon once again. The resulting mixture is stirred at 25° C., under inert atmosphere, for a suitable time. The desired acetylene is obtained as a precipitate, which can be isolated via filtration and air-dried.

Synthesis of Stilbenes 92 and 93 Via a Hydrosilylation-Protodesilylation Sequence, and Isolation of Stilbene 96.

A flame-dried, round-bottomed flask is loaded, in turn, with the diarylacetylene (1 equiv.), $EtOMe_2SiH$ (1.5 equiv.) and $PtO_2$ (7 mol %). The resultant mixture is kept overnight at 60° C., under a nitrogen atmosphere. Next, the excess $EtOMe_2SiH$ is evaporated under a high vacuum atmosphere, upon which the residue is dissolved in dry THF. The contents of the flask is cooled to 0° C., and a solution of tetra-n-butylammonium fluoride (TBAF) in THF is added dropwise (3 equiv.) The mixture is stirred overnight under a nitrogen atmosphere, while the temperature is allowed to rise to 20° C. The contents of the flask is filtered over Celite; the filtrate is concentrated in vacuo, taken up in diethyl ether and washed with brine (2×). The organic phase is subsequently dried over $MgSO_4$ and concentrated by rotary evaporation, furnishing the desired stilbene as a mixture of stereoisomers. The (E)- and (Z)-isomers can be isolated by means of preparative TLC, employing an eluent mixture of petroleum ether and diethyl ether (4:1).

Synthesis of Stilbene 94 Via Partial Hydrogenation in the Presence of Lindlar's Catalyst.

Lindlar's catalyst is loaded into a flame-dried, round-bottomed flask containing benzene. The resulting suspension is flushed thoroughly with hydrogen gas. Subsequently, a mixture of the diarylacetylene and quinoline in benzene are added. The contents of the flask is stirred at room temperature, under a hydrogen atmosphere, for an appropriate time. Next, the suspension is filtered over Celite, and the filtrate is concentrated in vacuo. The residual mixture of (E)- and (Z)-isomers of the desired stilbene can be separated by preparative TLC, employing an eluent mixture of petroleum ether and diethyl ether.

Preparation of (E)-Stilbene 95 Via a Wittig Reaction.

Benzyl bromide (1 mmol) and triphenylphosphine (0.26 g, 1 equiv.) are added to a flame-dried, round-bottomed flask filled with 5 mL of dry diethyl ether. The resulting suspension is heated to reflux under a nitrogen atmosphere for 12 h, whereupon the precipitated phosphonium salt can be isolated by filtration.

The resulting suspension can also be used as such in the Wittig reaction. In this case, 1 equiv. of KOtBu is added, after which the mixture is heated to reflux, still under a nitrogen atmosphere, for a further hour. Next, the contents of the flask is cooled to 0° C. and the aldehyde (0.5 equiv.) is added dropwise. The mixture is subsequently heated to reflux temperature for several hours, while reaction progress is monitored by means of TLC.

Upon reaction completion, the suspension is quenched by addition of an equal volume of water, and the emulsion is extracted with diethyl ether (2×). The combined organic layers are dried over $MgSO_4$, and the solvent is evaporated in vacuo. The resulting crude is taken up with hexane; impurities are removed by filtration and the hexane phase is concentrated in vacuo, furnishing the desired stilbene. If a mixture of (E)- and (Z)-isomers is formed, separation can be conducted by means of preparative TLC, employing an eluent mixture of petroleum ether and diethyl ether (4:1).

B.3. Compounds of the Invention

In table 8 that is set forth below, exemplary compounds according to formula I are set out in tabulated form.

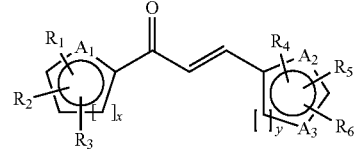

Formula I

TABLE 8

Compounds according to formula I

N°  Name 49  (2E)-3-(4-fluorophenyl)-1-(3,4,5-trimethoxyphenyl)prop-2-en-1-one
52  (2E)-3-(4-chlorophenyl)-1-(4-methoxyphenyl)prop-2-en-1-one
45  (2E)-1-(4-methoxyphenyl)-3-(2,4,6-trimethoxyphenyl)prop-2-en-1-one
54  (2E)-3-(3-fluorophenyl)-1-(4-fluorophenyl)prop-2-en-1-one
75  (2E)-3-(furan-2-yl)-1-(3,4,5-trimethoxyphenyl)prop-2-en-1-one
76  (2E)-1-(2,6-dimethoxyphenyl)-3-(furan-2-yl)prop-2-en-1-one
77  (2E)-1-(4-fluorophenyl)-3-(furan-3-yl)prop-2-en-1-one
70  (2E)-1,3-di(furan-2-yl)prop-2-en-1-one In table 9 that is set forth below, exemplary compounds according to formula II are set out in tabulated form.

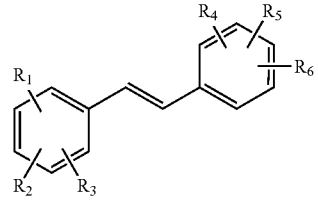

Formula II

TABLE 9

Compounds according to formula II

N°  Name 90  1,1'-(E)-ethene-1,2-diylbis(4-fluorobenzene)
91  1-fluoro-4-[(E)-2-(4-methoxyphenyl)ethenyl]benzene
92  1-fluoro-4-[(Z)-2-phenylethenyl]benzene
93  1,2,3-trimethoxy-5-[(Z)-2-phenylethenyl]benzene
94  5-[(Z)-2-(4-fluorophenyl)ethenyl]-1,2,3-trimethoxybenzene
95  1,1'-(E)-ethene-1,2-diyldibenzene
96  1,2,3-trimethoxy-5-[(E)-2-phenylethenyl]benzene C. Compilation of a Valuable Set of Anti-Invasive Chalcones Initially Available Data.

The well-documented proceedings of the Indo-Belgian screening program provide in vitro anti-invasive activity data for a total of 106 flavonoids and served as a starting point for the compilation of a suitable dataset for QSAR analysis.

Because of our intent to focus the predictive power of the model on chalcones, concurrently limiting the number of biological pathways through which the investigated compounds might act, only fully assessed chalcones from the list (compounds 1-34, table 10) were selected to make part of the training set.

TABLE 10

Overview of the structure, activity class and model prediction for the compounds in the training set.

| Compound | Structure | Actual class | Predicted class | Prediction error | Reference |
|---|---|---|---|---|---|
| 1 | (2E)-1-(5-Benzhydryl-2-hydroxy-4-methoxyphenyl)-3-(4-methoxyphenyl)propenone | 3 | 3 | 0 | Parmar, 1997 |
| 2 | (2E)-1-(5-Benzhydryl-2-hydroxy-4-methoxyphenyl)-3-(4-ethoxyphenyl)propenone | 3 | 3 | 0 | Parmar, 1997 |
| 3 | (2E)-1-(5-Benzhydryl-2-hydroxy-4-methoxyphenyl)-3-(4-phenoxyphenyl)propenone | 3 | 3 | 0 | Parmar, 1997 |
| 4 | (2E)-1-(5-Hydroxy-2,2,8,8-tetramethyl-3,4,9,10-tetrahydro-2H,8H-pyrano[2,3-f]chromen-6-yl)-3-p-tolyl-propenone | 3 | 3 | 0 | Parmar, 1997 |
| 5 | (2E)-1-[2,4-Dimethoxy-5-(3-methylbut-2-enyl)phenyl]-3-(2,2-dimethyl-5-phenethylchroman-6-yl)propenone | 1 | 2 | 1 | Parmar, 1997 |
| 6 | (2E)-1-(5-Hydroxy-2,2,8,8-tetramethyl-3,4,9,10-tetrahydro-2H,8H-pyrano[2,3-f]chromen-6-yl)-3-(4-phenoxypheny)propenone | 3 | 3 | 0 | Parmar, 1997 |
| 7 | (2E)-3-(3-Benzyloxy-4-methoxy-phenyl)-1-(5-hydroxy-2,2,8,8-tetramethyl-3,4,9,10-tetrahydro-2H,8H-pyrano[2,3-f]chromen-6-yl)propenone | 3 | 3 | 0 | Parmar, 1997 |
| 8 | (2E)-1-(5-Hydroxy-2,2,8,8-tetramethyl-3,4,9,10-tetrahydro-2H,8H-pyrano[2,3-f]chromen-6-yl)-3-(4-isopropylphenyl)propenone | 3 | 3 | 0 | Parmar, 1997 |
| 9 | (2E)-1-(3,7-Dihydroxy-2,2-dimethylchroman-6-yl)-3-(2,3-dimethoxy-phenyl)propenone | 1 | 2 | 1 | Parmar, 1997 |
| 10 | (2E)-3-(4-nitrophenyl)-1-(2',4'-dimethoxy-5'-(3-methylbut-2-enyl)phenyl)propenone | 3 | 3 | 0 | Parmar, 1997 |
| 11 | (2E)-3-phenyl-1-(2'-hydroxy-4',6'-dimethoxy-3'-(3-methylbut-2-enyl)phenyl)propenone | 2 | 1 | −1 | Parmar, 1997 |
| 12 | (2E)-1-(3,7-Dihydroxy-2,2-dimethylchroman-6-yl)-3-(2,4-dimethoxy-phenyl)propenone | 1 | 1 | 0 | Vanhoecke, 2005 |
| 13 | (2E)-3-(4-Benzyloxy-3-methoxyphenyl)-1-(3,4-bis-benzyloxyphenyl)propenone | 1 | 1 | 0 | Parmar, 1997 |
| 14 | (2E)-3-(4-(1-methylethyl)phenyl)-1-(2',4'-dimethoxy-5'-(3-methylbut-2-enyl)phenyl)propenone | 1 | 1 | 0 | Parmar, 1997 |
| 15 | (2E)-3-phenyl-1-(2',4',6'-trimethoxy-3'-(3-methylbut-2-enyl)phenyl)propenone | 3 | 2 | −1 | Parmar, 1997 |
| 16 | (2E)-3-(4-methylphenyl)-1-(3',4'-dimethoxyphenyl)propenone | 2 | 2 | 0 | Parmar, 1997 |
| 17 | (2E)-3-phenyl-1-(2'-hydroxy-3',4',6'-trimethoxyphenyl)propenone | 2 | 1 | −1 | Parmar, 1997 |
| 18 | (2E)-3-phenyl-1-(2',4'-dimethoxy-5'-(3-methylbut-2-enyl)phenyl)propenone | 0 | 1 | 1 | Parmar, 1997 |
| 19 | (2E)-3-(3,4-dimethoxyphenyl)-1-(2',4'-dimethoxy-5'-(3-methylbut-2-enyl)phenyl)propenone | 1 | 1 | 0 | Parmar, 1997 |
| 20 | (2E)-3-(4-nitrophenyl)-1-(3',4'-dimethoxyphenyl)propenone | 3 | 2 | −1 | Parmar, 1997 |
| 21 | (2E)-3-phenyl-1-(6'-hydroxy-2',3',4'-trimethoxyphenyl)propenone | 0 | 0 | 0 | Parmar, 1997 |
| 22 | (2E)-1-Benzo[1,3]dioxol-5-yl-3-(2,4-dimethoxyphenyl)propenone | 2 | 1 | −1 | Parmar, 1997 |
| 23 | (2E)-3-(3,4-Dimethoxyphenyl)-1-(7-hydroxy-2,2-dimethylchroman-6-yl)propenone | 2 | 2 | 0 | Parmar, 1997 |

TABLE 10-continued

Overview of the structure, activity class and model prediction for the compounds in the training set.

| Compound | Structure | Actual class | Predicted class | Prediction error | Reference |
|---|---|---|---|---|---|
| 24 | (2E)-1-(3-Hydroxy-5,7-dimethoxy-2,2-dimethylchroman-8-yl)-3-phenylpropenone | 0 | 1 | 1 | Parmar, 1997 |
| 25 | (2E)-3-(4-Benzyloxy-3-methoxyphenyl)-1-(3,4-bisbenzyloxyphenyl)propenone | 1 | 1 | 0 | Parmar, 2003 |
| 26 | (2E)-1-Benzo[1,3]dioxol-5-yl-3-(2,3-dimethoxyphenyl)propenone | 1 | 2 | 1 | Parmar, 2003 |
| 27 | (2E)-3-(4-hydroxyphenyl)-1-(2',4'-dihydroxy-6'-methoxy-3'-(3-methylbut-2-enyl)phenyl)propenone | 0 | 0 | 0 | Vanhoecke, 2005 |
| 28 | (2E)-3-(4-hydroxyphenyl)-1-(6'-hydroxy-2',4'-dimethoxy-3'-(2-propenyloxy)phenyl)propenone | 1 | 1 | 0 | Parmar, 2003; Mukherjee 2001 |
| 29 | (2E)-3-(2,4-Dimethoxyphenyl)-1-(3-hydroxy-7-methoxy-2,2-dimethylchroman-6-yl)-propenone | 3 | 2 | −1 | Parmar, 1997 |
| 30 | (2E)-3-(2,4-Dimethoxyphenyl)-1-(7-hydroxy-2,2-dimethyl-2H-chromen-6-yl)propenone | 3 | 3 | 0 | Parmar, 1997 |
| 31 | (2E)-3-(4-(1-methylethyl)phenyl)-1-(3',4'-dimethoxyphenyl)propenone | 3 | 2 | −1 | Parmar, 1997 |
| 32 | (2E)-3-(3-phenoxyphenyl)-1-(3',4'-dimethoxyphenyl)propenone | 3 | 2 | −1 | Parmar, 1997 |
| 33 | (2E)-3-(2,4-dimethoxyphenyl)-1-(2',4'-dimethoxy-5'-(3-methylbut-2-enyl)phenyl)propenone | 3 | 2 | −1 | Parmar, 1997 |
| 34 | (2E)-3-(3-phenoxyphenyl)-1-(2',4'-dimethoxy-5'-(3-methylbut-2-enyl)phenyl)propenone | 3 | 2 | −1 | Parmar, 1997 |
| 37 | (2E)-1,3-diphenylpropenone | 1 | 1 | 0 | — |
| 38 | (2E)-3-phenyl-1-(4-methoxyphenyl)propenone | 1 | 1 | 0 | — |
| 39 | (2E)-3-(4-Methoxyphenyl)-1-phenylpropenone | 1 | 1 | 0 | — |
| 40 | (2E)-3-(4-Methoxyphenyl)-1-(4-methoxyphenyl)propenone | 1 | 1 | 0 | — |
| 41 | (2E)-3-(3-Methoxyphenyl)-1-(4-methoxyphenyl)propenone | 0 | 1 | 1 | — |
| 42 | (2E)-3-(2,4,5-Trimethoxyphenyl)-1-(2,4,6-trimethoxyphenyl)propenone | 1 | 1 | 0 | — |
| 43 | (2E)-3-(4-Methoxyphenyl)-1-(2,4,6-trimethoxyphenyl)propenone | 1 | −1 | −2 | — |
| 44 | (2E)-3-(2,4,5-Trimethoxyphenyl)-1-(4-methoxyphenyl)propenone | 0 | 1 | 1 | — |
| 45 | (2E)-3-(2,4,6-Trimethoxyphenyl)-1-(4-methoxyphenyl)propenone | −1 | 0 | 1 | — |
| 46 | (2E)-3-(2,4,5-Trimethoxyphenyl)-1-(2,6-dimethoxyphenyl)propenone | 1 | 1 | 0 | — |
| 47 | (2E)-3-(2,4,6-Trimethoxyphenyl)-1-(2,6-dimethoxyphenyl)propenone | 0 | 0 | 0 | — |
| 48 | (2E)-3-(4-Fluorophenyl)-1-(4-methoxyphenyl)propenone | 0 | 0 | 0 | — |
| 49 | (2E)-3-(4-Fluorophenyl)-1-(3,4,5-trimethoxyphenyl)propenone | −2 | −1 | 1 | — |
| 50 | (2E)-3-(4-Fluorophenyl)-1-(4-fluorophenyl)propenone | 1 | 0 | −1 | — |
| 51 | (2E)-3-(4-Fluorophenyl)-1-phenylpropenone | 1 | 0 | −1 | — |

The potency of these molecules had been evaluated by means of the chick heart invasion assay, as described herein before. Translation of the assay invasion grade at different concentrations into statistically workable classes was performed by calculating the logarithm of the 'lowest active concentration $c_{min}$' for each compound, being the lowest concentration at which a substance exhibits an anti-invasive behavior (invasion grades I or II, Eq. 1). Hence, six activity levels were defined, ranging from class −2 for the most active compounds (invasion grade I or II at the 0.01 μmol/l level) to class 3 (compounds with no apparent effect at a concentration of 100 μmol/l, see Table 1 above).

$$\text{anti-invasive activity class} = \log c_{min} \quad \text{(Eq. 1)}$$

Expansion of the Data Set.

The chalcones in the Indo-Belgian screening library lack a systematic substitution pattern. Although the A- and B-rings of these natural products are decorated with a variety of interesting substituents commonly found in bioactive secondary plant metabolites (e.g. prenyl groups, chromane moieties, methylenedioxy and methoxy groups), we considered it necessary to expand the training set with a number of strategically chosen analogues (Table 11, 37-51). Primarily, we wanted to investigate the influence of the methoxy moiety on the activity level, by varying both the number and the position of this simple, electron donating group. Furthermore, four fluorinated chalcones (48-51) were prepared. We envisaged that these simple decoration patterns would provide us, to a certain extent, with information on the influence of the electron density of the two aromatic rings on the activity.

These fifteen chalcones were subsequently tested for their in vitro anti-invasive activity. Surprisingly, six compounds exhibited a potent activity at or below the 1 µmol/l level (activity class 0, −1 or −2). Particularly striking are the results for compounds 45 and 49: none of the natural products tested earlier in the Indo-Belgian screening program were reported to be active at concentrations as low as 0.01 µmol/l. Notwithstanding their low potency, the less active analogues also add useful information to the training sets.

TABLE 11

Overview of the structure and actual activity class of compounds 37-51.

|  | R | R' | Actual in vitro activity class |
|---|---|---|---|
| 37 | H | H | 1 |
| 38 | 4'-MeO | H | 1 |
| 39 | H | 4-MeO | 1 |
| 40 | 4'-MeO | 4-MeO | 1 |
| 41 | 4'-MeO | 3-MeO | 0 |
| 42 | 2',4',6'-triMeO | 2,4,5-triMeO | 1 |
| 43 | 2',4',6'-triMeO | 4-MeO | 1 |
| 44 | 4'-MeO | 2,4,5-triMeO | 0 |
| 45 | 4'-MeO | 2,4,6-triMeO | −1 |
| 46 | 2',6'-diMeO | 2,4,5-triMeO | 1 |
| 47 | 2',6'-diMeO | 2,4,6-triMeO | 0 |
| 48 | 4'-MeO | 4-F | 0 |
| 49 | 3',4',5'-triMeO | 4-F | −2 |
| 50 | 4'-F | 4-F | 1 |
| 51 | H | 4-F | 1 |

Final Compilation of the Data Set.

Combination of the newly obtained data with the earlier selected chalcones 1-34 from the Indo-Belgian screening program enabled us to compile a data set of 49 chalcones, covering a broad range of anti-invasive potency: activities vary from class 3—compounds possessing no activity at 100 µmol/l—to class −2—compounds active at 10 nmol/l. This group of 49 chalcones was subsequently used as a training set in the development of our QSAR model.

Correlation of In Vitro Anti-Invasive Activity Data for Chalcones with their Chemical Structure QSAR Modeling.

Two-dimensional drawings of the compounds were made using ChemDraw Ultra 7.0.1. Subsequently, these structures were loaded into HyperChem 8.0.3 and their refined equilibrium molecular geometry was obtained by (i) 2D to 3D conversion using parameters included in HyperChem, (ii) pre-optimization using the molecular mechanics force field (MM+) method and (iii) final optimization at the semi-empirical AM1-level of theory using a Polak-Ribiere conjugated gradient and an RMS gradient of 0.01 kcal/(Å·mol) as the termination condition for optimized structures.

These geometries were loaded into CODESSA Pro, a software package that combines diverse statistical structure-property-activity correlation techniques. Recently, this program successfully correlated and predicted a series of biological activities (e.g. HIV-1 protease inhibitory activity of substituted tetrahydropyrimidinones) and physicochemical properties (e.g. β-cyclodextrin complexation free energies).

Using MOPAC 7.05, implemented in the CODESSA Pro package, 863 theoretical descriptors were calculated. These can be classified into several groups: (i) constitutional, (ii) topological, (iii) geometrical, (iv) thermodynamic, (v) quantum chemical and (vi) charge related. All descriptors are derived solely from the molecular structure and their computation therefore requires no experimental data.

Next, the best multilinear equation (Eq. 1) correlating the anti-invasive activity class (log $c_{min}$) with n molecular descriptors ($D_i$), weighted by their regression coefficients $b_i$ was searched for using the 'Best Multilinear Regression' (BMLR) algorithm integrated into CODESSA Pro. As such, QSAR models employing up to ten descriptors were generated. Indeed, ten descriptors is the maximum allowed number for a dataset of fifty compounds according to the '5-to-1' rule of thumb.

$$\text{anti-invasive activity class} = \log C_{min} = b_0 + \Sigma_i^n b_i \cdot D_i \qquad \text{Eq. 2}$$

A crucial step in the development of a meaningful QSAR model is the detection of the 'break point', i.e. the number of descriptors beyond which the statistical improvement of the model attenuates upon addition of an extra descriptor. The most straightforward, often employed criterion in this context is a $\Delta r^2$ value of 0.05. Limiting the number of descriptors to an absolute minimum but not lower is also in accordance with the principle of parsimony (Occam's razor, and Einsteins' restatement of the latter: 'make everything as simple as possible, but not simpler').

As clearly illustrated in FIG. 1, the 'break point' is situated around n=6 for our dataset. From here on, additional descriptors will more likely lead to a better fit because of chance correlation than because of an underlying biochemical reason. Therefore, the six-descriptor model is our 'optimal model' (Eq. 3, Table 12, 13).

Optimal Model (Standard Errors Included for Indication of Accuracy Only)

$$\log c_{min} = -58.90 \pm 11.91 + (28.63 \pm 5.352) \times D_1 - (16.29 \pm 2.905) \times D_2 + (1.093 \pm 0.145) \times D_3 + (9.904 \pm 1.924) \times D_4 - (116.3 \pm 44.61) \times D_5 + (17.01 \pm 5.296) \times D_6 \qquad \text{(Eq. 3)}$$

TABLE 12

Statistical parameters of the model

| parameter | value |
|---|---|
| $r^2$ | 0.7411 |
| $q^2_{cvOO}$ | 0.6407 |
| $q^2_{cvMO}$ | 0.6385 |
| F-test | 20.03 |
| $v_1 = p = 6$ | 6 |
| $v_2 = n - p - 1 = 49 - 6 - 1$ | 42 |
| p-value | 0.000000 |
| s | 0.6945 |
| $\text{RMSPE}_{OO}$ | 0.77 |
| $\text{RMSPE}_{MO}$ | 0.7776 |
| RandTest | 0.251 |

TABLE 13

Descriptors $D_i$ of the optimal model and their statistical parameters

| i | Name of descriptor $D_i$ | t-stat | p-value* | IC |
|---|---|---|---|---|
| 0 | Intercept | 4.944 | 0.0000 | |
| 1 | Max antibonding contribution of one MO | 5.349 | 0.0000 | 0.1829 |
| 2 | Partial Surface Area for atom C | −5.608 | 0.0000 | 0.5732 |

TABLE 13-continued

Descriptors $D_i$ of the optimal model and their statistical parameters

| i | Name of descriptor $D_i$ | t-stat | p-value* | IC |
|---|---|---|---|---|
| 3 | Final heat of formation/# atoms | 7.537 | 0.0000 | 0.5959 |
| 4 | XY Shadow/XY Rectangle | 5.147 | 0.0000 | 0.2933 |
| 5 | Min 1-electron react. index for atom O | −2.608 | 0.0126 | 0.2122 |
| 6 | Polarity parameter (Zefirov) | 3.212 | 0.0025 | 0.3633 |

*t-test, $v_1 = n - p - 1 = 42$;
IC: partial intercorrelation.

Discussion of the QSAR Model: Statistical Evaluation, Internal Validation and Descriptor Interpretation.

Statistical Evaluation.

Our optimal six-descriptor model possesses an $r^2$ value of 0.7411. The confusion matrix, depicted in FIG. 2, serves as a good tool for further evaluation of the training set data fitting. Of the least active class 3, 9 out of 16 compounds (56%) are appointed to the right class. For class 2, the accuracy is lower at 40%. The activity of compounds from classes 1 and 0 is allotted with 67 and 50% accuracy respectively, whilst both most active compounds are sorted one class too high.

Whereas the fitting may at first sight seem mediocre for some classes, only one outlier is observed. Indeed, for all but one compounds, the error is at most one class unit. Moreover, an error of one class unit should be considered satisfactory in the present exercise, bearing in mind the discrete nature of the anti-invasive activity classes and the ensuing rounding error in the training data.

Furthermore, the allocation of the weakly and moderately active compounds (classes 3, 2 and 1) has an accuracy of 92% (36 out of 39 products). Inversely, 90% of the chalcones predicted to be weakly or moderately active indeed belong to classes 1, 2 or 3. Still, 60% (6 out of 10) of the most active compounds (classes 0, −1 and −2) are allocated correctly, and 67% of the substances predicted to be potent indeed are (6 out of 9). Therefore, the training set data fitting is reasonably high.

Another way to evaluate the quality of a regression fit is by performing an F-test, which results in the acceptance or rejection of the 'null hypothesis' $H_0$: there is no significant correlation between the dependant variable and independent variables ($b_1=b_2=b_i=0$). A p-value for the F-statistic of a model smaller than the critical value $\alpha/2=0.025$ points towards a good overall significance of the correlation. For the optimal model represented by Eq. 2, the p-value is 0.000000. Hence, the correlation in our model is significant, at least one descriptor is linearly associated with log $c_{min}$. In other words, $H_1$, the alternative hypothesis can be accepted (at least one $b_i \neq 0$). In fact, the high F-statistic suggests more than just one significant predictor.

Individual t-tests on each of the $b_i$'s of the regression equation show that each descriptor contributes significant information to the resulting prediction, since the p-value for each descriptor is smaller than $\alpha/2=0.025$. According to the test values (|t|), the significance of the descriptors in the model decreases in the order $D_3 > D_2 > D_1 > D_4 > D_6 > D_5$.

The standard error of prediction s for our optimal model is 0.6945. As a rule of thumb, a model is considered useful when the value of s is less than ten percent of the observation range. In our case, the standard error of prediction is slightly larger, but seems reasonable when considering the discrete nature of the source data.

Internal Validation of the Model.

One of the most important steps in the development of a valuable QSAR model is its validation. The majority of model reliability problems are a consequence of (i) overfitting or (ii) chance correlation.

(i) Overfitting is a common problem in chemometrics and can be assessed by using objective criteria such as cross-validation methods. The simplest of these is the commonly used 'leave-one-out' method (CVOO). In this approach, one data point is left out of the training set, upon which its activity is predicted by a model built with the same descriptors as the main model, though with regression coefficients calculated for the remaining n−1 compounds. This computation is performed for each point, whereupon the n predicted values are regressed with the experimental data, thus calculating $q^2_{cvOO}$.

During the BMLR calculations, CODESSA PRO automatically provides the results for the 'leave-one-out' cross-validation test. For our optimal model, an $q^2_{cvOO}$ of 0.6407 and a $RMSPE_{OO}$ of 0.77 were obtained, whereas the $r^2$ and s were 0.7411 and 0.6945 respectively. Therefore, it could be concluded that the generalization error is satisfactorily low. However, the 'leave-one-out' cross-validation technique has some serious deficiencies that confine its value. 'Leave-many-out' cross-validation (CVMO) is regarded as a superior technique. Therefore, the good CVMO results for our optimal model ($q^2_{cvMO}=0.6385$, $RMSPE_{MO}=0.7776$) provide more confidence regarding its robustness.

During the development of our predictive model, we initially included chalcone 52 in our training set. Strikingly, all of the obtained models were clearly overfitted towards compound 52, since cross-validation of these correlations failed each time when this structure was omitted. When removed from the training set, the present 'optimal model' was obtained which successfully underwent cross-validation checks. Clearly, the relationship between the structure of compound 52 and its in vitro activity differs strongly from that of the other substances in our training set, which points towards a different mode of action for this chalcone. We included compound 52 in our validation set (see further) to test this hypothesis.

(ii) The degree of chance correlation for our optimal equation was assessed by a randomization test. The average $r^2$ of 0.251 for twenty permutations of vector Y indicates a stronger relationship between our descriptors and the anti-invasive activity than expected due to chance. Furthermore, the p-values of the F-test for the model and the t-tests on the individual descriptors suggest the significance of the model correlation.

Model Interpretation.

The essential information provided by a QSAR model is contained in the physicochemical meaning of its descriptors, and their influence on the dependant variable. Therefore, an interpretation of the descriptors contained in our optimal model is imperative if the latter should be of any use. Although a direct comprehension of these descriptors is generally difficult, given the complexity of the interactions in the studied biochemical phenomena, the descriptors often can be associated with processes involved in the studied problem in a more indirect, but still valuable, way.

(i) The first descriptor, 'Maximum antibonding contribution of one MO' ($D_1$, Table 2), is a quantum chemical descriptor that is related to the stability of a molecule, given that a larger antibonding contribution will result in a higher energy molecular orbital. The coefficient of $D_1$ has a positive sign, which suggests that lower energetic molecules will exhibit a stronger anti-invasive potency. Moreover, a higher score for this descriptor type has been associated with an increased aqueous solubility. In the present study, this would signify that more lipophilic compounds will possess stronger anti-invasive properties.

(ii) Descriptor $D_2$, 'Partial Surface Area for atom C', together with its negative coefficient, highlights the importance of hydrocarbon moieties in the molecule and may point towards an important Van der Waals contribution to the host-guest interaction, i.e. the presence of an important lipophilic binding site in the binding pocket.

(iii) The most significant descriptor of the model, according to the t-statistic, is $D_3$: 'Final heat of formation/# atoms'. The coefficient of this quantum chemical descriptor carries a positive sign. Consequently, for thermodynamically more stable compounds, which possess a negative energy of formation, the contribution of this descriptor will result in a lower overall score and thus a higher anti-invasive activity. This observation is consonant with the information extracted from descriptor $D_1$.

(iv) 'XY Shadow/XY Rectangle', $D_4$, is a molecular shadow indices, defined as the projection of the molecules Van der Waals envelope on the XY plane, where X and Y are the shortest and second shortest inertial axes of the molecule, respectively. The shadow area is usually determined through application of a two dimensional square grid on the molecular projection and subsequent summation of the areas of squares overlapped with the projection. This descriptor is directly connected to the molecular size and consequently also stresses the van der Waals contribution to the binding at the molecular target. Furthermore, it may furnish information about the correct orientation of the chalcone towards its target. Since the coefficient for this descriptor bears a positive sign, molecules with smaller projected dimensions in the XY plane will have a higher desired activity. This may very likely be due to a better fit of molecules with a smaller projected XY envelope in the binding pocket.

(v) Descriptor $D_5$ is the 'minimum 1-electron reaction index for an oxygen atom', calculated as $$D_5 = \sum_{i \in A} \sum_{i \in A} \frac{c_{iHOMO} c_{jLUMO}}{\varepsilon_{LUMO} - \varepsilon_{HOMO}},$$

in which summations are performed over all atomic orbitals i, j of the given atom, $c_{iHOMO}$ and $c_{jLUMO}$ are the i-th and j-th atomic orbital coefficients on the HOMO and LUMO, respectively, and $\varepsilon_{LUMO}$ and $\varepsilon_{HOMO}$ represent the energies of the latter orbitals. This descriptor probably highlights an important interaction between the receptor binding site and the carbonyl oxygen or one or more other oxygen atoms present in the molecule.

(vi) The sixth descriptor in our QSAR-equation is the 'Polarity parameter', which is defined as $$D_6 = q_{max} - q_{min},$$

i.e. the difference between the most positive and most negative partial charges in the molecule. In this calculation, the charge distribution in the molecule is determined based on Zefirov's approach, which uses the Sanderson electronegativity scale and represents the molecular electronegativity as the geometric mean of the atomic electronegativities. The positive coefficient for this descriptor indicates that less polar, more lipophilic tend to exhibit a better anti-invasive potency. This again agrees with the analysis made for descriptor $D_1$ and $D_2$.

In summary, the above descriptor interpretation provides a number of interesting guidelines for the design of novel, more powerful anti-invasive chalcones:

I. A stronger activity is to be expected for more apolar compounds ($D_1$, $D_2$, $D_6$). Van der Waals contributions may play an important role in host-guest interactions, which suggests the presence of a lipophilic site in the binding pocket.

II. Thermodynamically more stable compounds will be more potent ($D_1$, $D_3$).

III. Molecules with smaller projected dimensions on the XY plane may fit better in the binding pocket ($D_4$).

IV. The carbonyl group is most likely involved in an important interaction with a more polar region of the binding pocket ($D_5$).

External Validation: QSAR Directed Design, Synthesis and Evaluation of New Anti-Invasive Compounds.

External Validation of the Model.

Too often, the cross-validated $q^2$ is used as the sole indicator of the quality of a QSAR model. A high value for cross-validated $q^2$ is a necessary but not sufficient requisite for predictivity. Evaluation of the model against an external dataset remains the only reliable judgment of its true predictive power. Thus, upon model interpretation, it was our contention to design, synthesize and test such an external set of compounds based upon the predictions of our model and the guidelines extracted from its descriptors.

Selecting Compounds for Synthesis.

To confirm the external predictive power of our model, we calculated the anti-invasive activity of 250 hypothetical chalcones. Twenty-five of these compounds were synthesized of which 19 were tested in vitro. The thus obtained data provided us with an external validation set. Given the extraordinary high potency of the newly assessed fluorinated chalcone 49, present in our training set, we incorporated an additional five fluorine containing chalcones (53-55, 58, 62) in the validation set. Our QSAR-model anticipates a strong anti-invasive tendency for three of these compounds (53, 55 and 59). Since two C-prenylated chalcones in the training set were quite potent (class 0), we were intrigued to investigate the potential of their more readily obtainable O-prenylated analogues. Hence, one of the fluorochalcones (62) was designed to bear a prenyloxy moiety.

Besides, the single furyl chalcone (28) in the training set drew our attention, as members of this compound class have been proposed as possible leads for novel angiogenesis inhibitors and dual COX and 5-LOX inhibitors. Consequently, we were intrigued to further explore the anti-invasive potential of this compound class and incorporated ten differentially functionalized furyl chalcones in the validation set. Our QSAR-model forecasts several of these molecules (70, 75, 76 and 77) to be highly interesting.

In order to further evaluate the domain of applicability of our model to other heterocyclic chalcone cores, two indolyl chalcones (84 and 85) were added to the validation set. This relatively unexplored compound class exhibits anti-inflammatory properties and cytotoxicity versus cancer cells in vitro. Furthermore, close analogues of these substances were shown to be microtubule depolymerization agents, active against glioblastoma in vivo, which underlined their ability to cross the BBB and validated their potential as systemic chemotherapeutics, including delivery to the brain parenchyma and the central nervous system. Nevertheless, according to the predictions of our model, these compounds should lack anti-invasive behavior (class 4/5).

As has been explained higher, compound 52 was included in the validation set so as to help confirm its aberrant mode of action. Besides, in order to substantiate the poor in vitro potential of the nitrochalcone scaffold, and to evaluate the applicability of the developed model to this molecular family, two more nitro-bearing chalcones (88 and 89) were incorporated in the validation set, both of which have a low activity in silico. The latter two substances had been synthesized and evaluated in vitro earlier.

In this manner, we compiled a validation set comprising 20 molecules of fairly large molecular diversity, of which the anti-invasive activity were determined in vitro (table 14) using the chicken hear invasive assay as described herein above, and which possessed in silico anti-invasive activity values spread over a broad concentration range. Subsequently, said in vitro date were compared with the obtained in silico data as represented in table 14, in order to validate our predictive model.

TABLE 14

Comparison between the predicted and actual in vitro anti-invasive activity classes for the validation set.

| | structure | anti-invasive activity class | | |
|---|---|---|---|---|
| | | pred. | act. | error |
| 52 | (2E)-3-(4-chlorophenyl)-1-(4-methoxyphenyl)prop-2-en-1-one | 2 | −2 | 4 |
| 53 | (2E)-3-(3-Fluorophenyl)-1-(4-fluorophenyl)propenone | −2 | −1 | −1 |
| 54 | (2E)-3-(3-Fluorophenyl)-1-(4-methoxyphenyl)propenone | 1 | 1 | 0 |
| 55 | (2E)-3-(2-Fluorophenyl)-1-(4-methoxyphenyl)propenone | 0 | 1 | −1 |
| 58 | (2E)-3-(4-Fluorophenyl)-1-(4-hydroxyphenyl)propenone | 0 | 1 | −1 |
| 62 | (2E)-3-(4-Fluorophenyl)-1-[4-(3-methylbut-2-enyloxy)phenyl]propenone | 1 | >=2 | >=1 |
| 68 | (2E)-1-(2-Furyl)-3-(3-fluorophenyl)propenone | 1 | 1 | 0 |
| 70 | (2E)-1,3-Difuran-2-yl-propenone | −1 | −1 | 0 |

TABLE 14-continued

Comparison between the predicted and actual in vitro anti-invasive activity classes for the validation set.

| | structure | anti-invasive activity class | | |
|---|---|---|---|---|
| | | pred. | act. | error |
| 72 | (2E)-3-Furan-2-yl-1-phenylpropenone | 3 | >=2 | — |
| 73 | (2E)-3-(2-Furanyl)-1-(4-fluorophenyl)propenone | 1 | 2 | −1 |
| 74 | 3-Furan-2-yl-1-(4-methoxyphenyl)propenone | 1 | 2 | −1 |
| 75 | (2E)-3-(2-Furanyl)-1-(3,4,5-trimethoxyphenyl)propenone | 0 | −1 | 1 |
| 76 | (2E)-3-(2-Furanyl)-1-(2,6-dimethoxyphenyl)propenone | 0 | −1 | 1 |
| 77 | (2E)-3-(3-Furanyl)-1-(4-fluorophenyl)propenone | 0 | −1 | 1 |
| 78 | (2E)-3-(2-Benzofuranyl)-1-(4-fluorphenyl)propenone | 1 | 2 | −1 |
| 79 | (2E)-3-(2-Benzofuranyl))-1-(4-methoxyphenyl)propenone | 3 | 2 | 1 |
| 84 | (2E)-3-(4-Chlorophenyl))-1-(1-allyl-1H-indol-3-yl)propenone | 5 | ≥2 | — |
| 85 | (2E)-3-(4-Chlorophenyl)-1-[1-(3-methylbut-2-enyl)-1H-indol-3-yl]propenone | 4 | ≥2 | — |
| 88 | (2E)-1-(5-Hydroxy-2,2,8,8-tetramethyl-3,4,9,10-tetrahydro-2H,8H-pyrano[2,3-f]chromen-6-yl)-3-(3-nitro-phenyl)propenone | 4 | ≥3 | — |
| 89 | (2E)-1-(5-Benzhydryl-2-hydroxy-4-methoxy-phenyl)-3-(3-nitro-phenyl)-propenone | 2 | ≥3 | ≥1 |

A comparison between the predicted and observed in vitro anti-invasive activity values is depicted in table 14 and in the confusion matrix in FIG. 3. As can be derived from the external predictivity of the model is reasonably good, given the discrete nature of the source data.

As evident from table 15 below, a whole range of chalcone-like compounds are already known in the prior art, nevertheless said compounds are predicted to have a lowest active concentration of 1 μM (predicted class ≥0) when making use of the method according to this invention. As such it is predicted that higher concentrations of said compounds are needed in order to obtain a similar anti-invasive effect in comparison to the compounds according to this invention, thereby making them less suitable for the development of anti-invasive drugs.

TABLE 15

Prediction of anti-invasive activity of known chalcone-like compounds

| CAS-number | Name | Predicted Class |
|---|---|---|
| 94-41-7 | 2-Propen-1-one, 1,3-diphenyl- | 1 |
| 104890-73-5 | 2-Propen-1-one, 1-(4-chlorophenyl)-3-(2,6-dichlorophenyl)- | 1 |
| 125041-90-9 | 2-Propen-1-one, 1-(4-chlorophenyl)-3-(3,4-dichlorophenyl)- | 4 |
| 142531-18-8 | 2-Propen-1-one, 3-(2,6-dichlorophenyl)-1-(4-methoxyphenyl)- | 4 |
| 196081-85-3 | 2-Propen-1-one, 3-(3-bromo-4-methoxyphenyl)-1-phenyl- | 3 |
| 22248-31-3 | 2-Propen-1-one, 1-(3,4-dimethoxyphenyl)-3-(4-methoxyphenyl)- | 1 |
| 259099-77-9 | 2-Propen-1-one, 1-(4-bromophenyl)-3-(3,5-difluorophenyl)- | 0 |
| 282730-69-2 | 2-Propen-1-one, 1-(2-chlorophenyl)-3-(2,6-dichlorophenyl)- | 3 |

TABLE 15-continued

Prediction of anti-invasive activity of known chalcone-like compounds

| CAS-number | Name | Predicted Class |
|---|---|---|
| 283155-45-3 | 2-Propen-1-one, 1-(2-chlorophenyl)-3-(3,5-dichloro-2-hydroxyphenyl)- | 1 |
| 283155-74-8 | 2-Propen-1-one, 3-(4-chlorophenyl)-1-(2,6-dichlorophenyl)- | 1 |
| 52601-63-5 | 2-Propen-1-one, 3-(2,4-dichlorophenyl)-1-(4-methoxyphenyl)- | 3 |
| 57076-84-3 | 2-Propen-1-one, 1-(4-chlorophenyl)-3-(2,4-dichlorophenyl)- | 1 |
| 1154-77-4 | 2-Propen-1-one, 1-(2,4-dimethoxyphenyl)-3-phenyl- | 0 |
| 1202275-66-8 | 2-Propen-1-one, 3-(2,3-dimethoxyphenyl)-1-(3,4,5-trimethoxyphenyl)-, (2E)- | 2 |
| 127034-09-7 | 2-Propen-1-one, 3-(4-bromophenyl)-1-(3,4,5-trimethoxyphenyl)-, (2E)- | 3 |
| 1274882-05-1 | 2-Propen-1-one, 1-(2-bromo-4-methoxyphenyl)-3-phenyl-, (2E)- | 4 |
| 130768-85-3 | 2-Propen-1-one, 1,3-bis(3,4-dimethoxyphenyl)-, (2E)- | 3 |
| 130768-87-5 | 2-Propen-1-one, 1,3-bis(3,4,5-trimethoxyphenyl)-, (2E)- | 1 |
| 151703-83-2 | 2-Propen-1-one, 3-(4-methoxyphenyl)-1-(3,4,5-trimethoxyphenyl)-, (2E)- | 2 |
| 151703-84-3 | 2-Propen-1-one, 3-(2,4-dimethoxyphenyl)-1-(3,4,5-trimethoxyphenyl)-, (2E)- | 3 |
| 151703-87-6 | 2-Propen-1-one, 3-(3,4-dimethoxyphenyl)-1-(3,4,5-trimethoxyphenyl)-, (2E)- | 2 |
| 1774-66-9 | 2-Propen-1-one, 3-(4-bromophenyl)-1-phenyl- | 4 |
| 18493-30-6 | 2-Propen-1-one, 1-(2,4-dimethoxyphenyl)-3-(4-methoxyphenyl)- | 1 |
| 19672-61-8 | 2-Propen-1-one, 3-(4-bromophenyl)-1-(4-chlorophenyl)- | 2 |
| 214264-40-1 | 2-Propen-1-one, 1-(3,4-dimethoxyphenyl)-3-(4-ethoxyphenyl)-, (2E)- | 1 |
| 214264-42-3 | 2-Propen-1-one, 1-(3,4-dimethoxyphenyl)-3-(4-methoxyphenyl)-, (2E)- | 2 |
| 41343-31-1 | 2-Propen-1-one, 3-(2,4,5-trimethoxyphenyl)-1-(3,4,5-trimethoxyphenyl)-, (2E)- | 1 |
| 450342-04-8 | 2-Propen-1-one, 1-(3,4-dimethoxyphenyl)-3-(3,4,5-trimethoxyphenyl)-, (2E)- | 1 |
| 614-47-1 | 2-Propen-1-one, 1,3-diphenyl-, (2E)- | 1 |
| 6332-22-5 | 2-Propen-1-one, 1-(4-bromophenyl)-3-(4-chlorophenyl)- | |
| 934022-25-0 | 2-Propen-1-one, 3-(3-methoxyphenyl)-1-(3,4,5-trimethoxyphenyl)-, (2E)- | 3 |
| 959-23-9 | 2-Propen-1-one, 1-(4-methoxyphenyl)-3-phenyl- | 1 |
| 959-33-1 | 2-Propen-1-one, 3-(4-methoxyphenyl)-1-phenyl- | 1 |
| 183018-76-0 | 2-Propen-1-one, 3-(2,4-dichlorophenyl)-1-(2-methylphenyl)- | 3 |
| 183018-77-1 | 2-Propen-1-one, 3-(2,6-dichlorophenyl)-1-(2-methylphenyl)- | 4 |
| 197662-80-9 | 2-Propen-1-one, 1-(3,4-dimethoxyphenyl)-3-(4-methylphenyl)- | 3 |
| 219140-56-4 | 2-Propen-1-one, 1-(4-chloro-3-methylphenyl)-3-(2-chlorophenyl)- | 2 |
| 219140-57-5 | 2-Propen-1-one, 3-(2-chloro-6-fluorophenyl)-1-(4-chloro-3-methylphenyl)- | 1 |
| 219140-58-6 | 2-Propen-1-one, 1-(4-chloro-3-methylphenyl)-3-(2,6-dichlorophenyl)- | 1 |
| 312700-11-1 | 2-Propen-1-one, 3-(3,4-dichlorophenyl)-1-(2-methylphenyl)- | 3 |
| 312700-12-2 | 2-Propen-1-one, 3-(2,6-dichlorophenyl)-1-(3-methylphenyl)- | 5 |
| 312700-13-3 | 2-Propen-1-one, 3-(5-bromo-2-hydroxyphenyl)-1-(3-methylphenyl)- | 5 |
| 325819-18-9 | 2-Propen-1-one, 3-(2,4-dichlorophenyl)-1-(3-methylphenyl)- | 2 |
| 198125-17-6 | 2-Propen-1-one, 1-(3,4-dimethoxyphenyl)-3-(3-methylphenyl)-, (2E)- | 3 |
| 214264-37-6 | 2-Propen-1-one, 1-(3,4-dimethoxyphenyl)-3-(2-methylphenyl)-, (2E)- | 3 |
| 214264-38-7 | 2-Propen-1-one, 1-(3,4-dimethoxyphenyl)-3-(4-methylphenyl)-, (2E)- | 1 |
| 934022-24-9 | 2-Propen-1-one, 3-(4-methylphenyl)-1-(3,4,5-trimethoxyphenyl)-, (2E)- | 1 |

Example

Matrigel Invasion Assay of Compound 49

An interesting method to determine the invasive capacity of cells and the anti-invasive potential of different substances is the matrigel invastion assay. Matrigel can be considered to be a basal membrane and is obtained from mice EHS sarcomas (tumors having an abundant expression of extracellular matrix proteins). The primary component of a matrigel is laminin, further also including collagen IV, heparan, sulphate proteoglycans and growth factors. It is also important that matrix degrading enzymes and inhibitors are present.

At room temperature, matrigel polymerizes into a matrix which mimicks a basal membrane of breast cells. The behavior of cells towards a matrigel highly resembles the in vivo situation and therefore this test is acknowledged to be an appropriate approach to the study migration and invasion, and the role of ECM receptors and matrix degrading enzymes in these processes.

In particular for this example, test cells were placed on a matrigel layer in serum-free medium. Subsequently, said cells were allowed to invade into the matrigel layer upon which they move through a filter, and attach to the bottom of said filter. The migration of the cells is stimulated by the presence of conditioned medium, at the other side of the filter, which act as a chemoattractant for the cells.

Protocol:

50 μl matrigel (+/−3 mg/ml serum-free DMEM) was applied in the apical compartment (upper chamber) of 24-well plate inserts having a pore size of 8 μm. After 1 h of polymerization (37° C.) 50.000 BLM cells (in 150 μl serum-free DMEM) were seeded and incubated with varying concentrations of compound 49 (0-100 μM). In the basolateral compartment (lower chamber), 700 μl conditioned medium, containing the same concentration of compound 49 as used in the apical compartment was applied as a chemo-attractant for the cells. The plates were incubated for 24 h at 37° C. and the matrigel and cells at the apical side were removed using wetted cotton swabs (PBSD-). The filters were washed twice on both sides with PBSD- and subsequently incubated for 10 min in ice-cold methanol to fix the cells. To quantify the number of migrated cells, the filters were incubated for 15 min with DAPI and subsequently washed 4×5 min with PBSD-. The filters were then mounted on coverslips and the number of migrated cells was determined for each concentration of compound 49 using a fluorescence microscope.

Results

Untreated BLM cells (melanoma) are highly invasive in a matrigel, however upon treatment with varying concentrations of compound 49, the amount of invasive BLM-cells is significantly reduced (ANOVA, p=0.001) as evident from table 16.

TABLE 16

Number of invasive BLM-cells found at the basolateral side of the filter

| Sample | Blanco | 0.1 μM | 1 μM | 10 μM | 100 μM |
|---|---|---|---|---|---|
| 1 | 664 | 62 | 282 | 57 | 7 |
| 2 | 668 | 210 | 160 | 33 | 19 |

Treatment with 100 μM compound 49 results in a 98% reduction of the number of invasive cells (Tukey HSD, p<0.05). However, also lower concentrations of compound 49 result in a significant reduction (p<0.05) reduction of the number of invasive cells i.e. 93% (10 μM), 67% (1 μM) and 80% (0.1 μM)

In Vivo Experiment: Survival Study

Materials and Methods

In order to evaluate the in vivo potency of 4-fluoro-3',4',5'-trimethoxychalcone 49 against the MCF-7/6 mammary carcinoma cell line, a broadly used metastasis experiment involving intracardial injection of the cancer cells was conducted. One week after subcutaneous implantation of an estrogen pellet (1 mg) in the dorsal region of the neck, 22 Swiss nu/nu mice were injected in the left cardiac ventricle with $1.10^5$ MCF-7/6 cells under xylazine and ketamine anesthesia (Smith W., 1993).

MCF-7 cells were originally obtained from a pleural effusion of a postmenopausal nulliparous woman (Soule et al., 1973). This cell line possesses an array of steroid and peptide hormone receptors, and has retained hormone responsiveness. Hence, the growth of MCF-7 tumors in nude mice is enhanced by estrogen administration, which was assured in our experiment through the aforementioned implant (Shafie S. M., 1980; Welsch et al., 1981).

By virtue of injection into the left cardiac ventricle, cancer cells directly enter systemic arterial circulation, which enhances the chance for colonization (Arguello et al., 1988). Hence, this type of inoculation is widely used to induce metastases in the bone and the bone marrow (Wetterwald et al., 2002). However, since these metastases are difficultly detectable and quantifiable, survival time was chosen as the sole end point in this study.

Upon inoculation, mice were divided randomly into two equal groups. One cohort was intraperitoneally injected with 10 nmol of 49 thrice a week (160 μg·kg$^{-1}$ for a 20 g animal), while the other group only received the vehicle (100 μL of serum-free DMEM containing 1:1000 DMSO).

Four-week-old female Swiss nu/nu mice were acquired from Charles River (France). These mice have a mutation in the nude gene of the ectoderm, which gives rise to a defect in hair formation, resulting in their hairless phenotype. This mutation furthermore causes the lack a functional thymus. As a result, Swiss nu/nu mice do not have T lymphocytes and are impaired in immune function, which renders them suitable hosts for tumor development upon injection with human neoplastic cells (Reth M., 1995).

Animals were fed a sterile 'RO4 Aliment Composé Complet' diet (UAR, Epinay-sur-Orge, France). Drinking water was sterilized and then acidified with 35% HCl (1:10,000). Both feed and water were provided ad libitum. Mice were kept in sterile filter-top cages, containing wood shavings, a shelter and nesting material. Cages were changed once or twice a week; humidity, temperature (between 25 and 30° C.) and general animal condition were assessed on a daily basis.

Twenty 6-week old female Swiss nu/nu mice were given a subcutaneous estrogen implant (1 mg) in the dorsal region of the neck. One week later, intracardial injection of 100,000 MCF-7/6 cells in 100 μM of PBS$^{D+}$ was performed. Animals were anesthesized priorly by i.p. injection of of xylazine (5 μL, Rompun®) and ketamine (36 μL, Ketalar®). Intracardial injection was performed with a 30 G needle (½"), which was introduced into the thoracic cavity underneath the sternum. Upon protrusion of the wall of the left ventricle, blood is pumped into the syringe. At this moment, careful injection of the cancer cells can be conducted. Next, mice were randomly divided into a vehicle control and a 49-treated cohort.

From the inoculation date on, mice were treated i.p. three times a week with 100 μL of a 100 μmol·L$^{-1}$ solution of 49 in serum-free DMEM containing 1:1000 DMSO, or with vehicle alone (see "preparation procedure"). Survival numbers for both cages were recorded on a daily basis.

"Preparation procedure": for the 49-treated group, 100 mmol·L$^{-1}$ solutions of 49 in DMSO were freshly prepared on each injection day, and diluted 1:1000 with serum-free DMEM so as to obtain injectable solutions of 100 μmol·L$^{-1}$ of 49. Control mice were given i.p. injections with 100 μL of the vehicle (1:1000 DMSO in serum-free DMEM).

Results

An overview of the observations made in the course of the experiment is represented in Table 17. As two animals died during intracardial injection, both cohorts initially comprised 10 mice. At week 5-6, differentiation in survival between the two groups became apparent, as 7 control mice died in a short period (days 34-51). Though no definite cause of death could be determined, such a pattern is often observed in cancer-related mortality (Hung et al., 2011; Arap et al., 1998). In the treatment group, only one mouse was lost in the same period. At three months, the experiment was terminated and surviving mice were sacrificed and examined by necropsy. No macroscopic metastases were detected.

TABLE 17

Full accounting of the data of the survival experiment.

| | Vehicle-treated group | | | | 49-Treated group | | | |
|---|---|---|---|---|---|---|---|---|
| Day | # at risk | # deaths | $p_{surv}$ | $p_{cum}$ | # at risk | # deaths | $p_{surv}$ | $p_{cum}$ |
| 0 | 10 | | | | 10 | | | |
| 2 | 10 | 1 | 0.9 | 0.9 | | | | |
| 5 | | | | | 10 | 1 | 0.9 | 0.9 |
| 34 | 9 | 1 | 0.899 | 0.8 | | | | |
| 36 | 8 | 1 | 0.875 | 0.7 | | | | |
| 40 | | | | | 9 | 1 | 0.89 | 0.8 |
| 42 | 7 | 1 | 0.857 | 0.6 | | | | |
| 43 | 6 | 1 | 0.833 | 0.5 | | | | |
| 44 | 5 | 1 | 0.8 | 0.4 | | | | |
| 49 | 4 | 1 | 0.75 | 0.3 | | | | |
| 51 | 3 | 1 | 0.667 | 0.2 | | | | |
| 59 | 2 | 1 | 0.5 | 0.1 | | | | |
| 61 | 1 | 1 | 0 | 0 | 8 | | 1 | 0.8 |

A Kaplan-Meier survival curve for both the 49-treated and vehicle-treated cohort is represented in FIG. 4. This curve provides the estimated cumulative probability of survival in time. A comparison of survival curves for both cohorts through a Mantel-Cox Log rank results in a p-value of 0.018. Hence, a significant difference in survival between treated and untreated animals was obtained.

Effect of the Compounds on the Growth and Viability of Cells.

Sulforhodamine B Test

The SRB assay is used to evaluate growth effects on cells, and measures the total protein content. In this test, 5,000 cells are seeded in a cup of a 96-well plate. Upon a 24 h-attachment period, cells are treated with a certain amount of the test molecule (dissolved in DMSO). After a pre-chosen incubation time, cells are fixed with 50 µL of 50% trichloroacetic acid (2° C., 1 h). Afterward, the plate is rinsed five times with tap water, and air dried overnight.

Next, proteins are stained with 75 µL of a 0.4% solution of SRB in AcOH (30 min). Unbound SRB is subsequently removed by washing with a 1% solution of glacial AcOH, whereupon the plate is air dried. Then, bound SRB is redissolved in 100 µL of a 10 mmol·L$^{-1}$ tris(hydroxymethyl)aminomethane (Tris) buffer (pH=10.5), after which optical density is determined at 490 nm with a spectrophotometer.

MTT test

An MTT test provides an indication of cell viability, proliferation and activity through determination of the mitochondrial conversion of 3-(4,5-dimethylthiazol-2-yl)-2,5-diphenyltetrazolium bromide (MTT), a yellow salt, into formazan, a salt that precipitates under the form of blue crystals.

In concreto, 5,000 cells are seeded in a cup of a 96 well-plate, treated with the desired amount of the test substance, and incubated for a chosen period of time. Next, 40 µL of a filtered (0.2 µm) 5 mg·mL$^{-1}$ solution of MTT in PBS is added to the cup. After 2 h of incubation at 37° C. in the dark, all liquid is removed. The obtained formazan salts are dissolved in 200 µL of DMSO, whereupon optical density is measured at 490 nm.

Results

An overview of the general antiproliferative effects of the compounds on neoplastic and healthy cell lines was obtained.

The effects of some chalcone-like compounds on the proliferation of MCF-7/6 cells were investigated. A commonly used method to quantify the metabolic activity of cells and thus to a certain degree cell viability—is the MTT assay. This test provides a measure of mitochondrial activity, as it assesses the reduction of 3-(4,5-dimethylthiazol-2-yl)-2,5-diphenyltetrazolium bromide (MTT), a yellow tetrazole, to the purple formazan; this transformation occurs in the mitochondria of living cells (Mosmann T., 1983).

Thus, the influence of 13 compounds on the mitochondrial activity of MCF-7/6 cells was determined at 3 different concentrations, both after 24 and 48 h of incubation. Assessment of the mitochondrial activity after 192 h of incubation, which would correspond to the duration of the CHI assay, was not possible as the degree of confluence of the cells was too high at that time point.

From FIG. 5, it appears that none of the compounds engenders significant cytotoxicity. Most substances mediate a 20% inhibition of mitochondrial activity at the 5 µmol·L$^{-1}$ level, but cause no effects at lower concentrations. Still, it should be noted that for both incubation times, compound 49 displayed the largest antiproliferative effect at 5 µmol·L$^{-1}$, causing a decrease in mitochondrial activity of 35 and 25% after 24 and 48 h, respectively. Nevertheless, its activity levels at lower concentrations were in line with those exerted by the other compounds.

The antiproliferative effects of 4-fluoro-3',4',5'-trimethoxychalcone on MCF-7/6 cells were further assessed in the MTT assay upon prolonged incubation, as this would provide a higher degree of relevance to the CHI assay, which has an 8-day incubation period. As mentioned above, cell confluence was too high after 192 h; therefore, an incubation time of 144 h was considered a good compromise.

Besides, also an SRB assay was performed. This test is based on the ability of the dye sulforhodamine B (SRB) to bind electrostatically on basic amino acid residues of protein in trichloroacetic acid-fixed cells. Results obtained in the SRB assay are linearly proportional to the amount of cellular protein and thus to the cell number. Hence, the SRB assay would provide additional information on the antiproliferative effects of compound 49.

In order to further validate the use of the MCF-7/LucF5 cells in our in vivo experiments, the effects of 4-fluoro-3',4', 5'-trimethoxychalcone on this cell line in the MTT and SRB assays were determined as well (Van Hoorde L. et al., 1999).

As can be appreciated from FIG. 6, a significant reduction in both mitochondrial activity and total protein content in MCF-7/6 cells was mediated by compound 49 at 100 and 10 µmol·L$^{-1}$ (p<0.01). A smaller but still significant reduction in the number of cells was observed at 1 µmol·L$^{-1}$, whereas mitochondrial activity had increased significantly upon treatment with 0.1 µmol·L$^{-1}$ of compound 49.

Treatment of MCF-7/LucF5 cells with 100 or 10 µmol·L$^{-1}$ of compound 49 gave rise to a significant reduction in total protein content after 72 h (p=0). Concentrations of 1 and 0.1 µmol·L$^{-1}$ only caused a marginally significant reduction of the cell count at the same time point (p=0.0703 and 0.0538, respectively). After significant reductions with respect to the solvent control were 100 or 10 µmol·L$^{-1}$ of the compound.

The results obtained in the MTT test were broadly comparable to those of the SRB assay: after 72 and 144 h, a significant reduction in mitochondrial activity of MCF-7/LucF5 cells was observed upon treatment with 100 µmol·L$^{-1}$ and 10 µmol·L$^{-1}$ of compound 49. Remarkably, a significant reduction in mitochondrial activity after 72 h of incubation was also obtained at the 0.1 µmol·L$^{-1}$ level (p=0.0196), although the number of cells had not altered (according to the SRB test). After 144 h, restoration of viability to the control level had occurred in the cells treated with 0.1 µmol·L$^{-1}$ of the compound.

As 4-fluoro-3',4',5'-trimethoxychalcone had exerted an anti-invasive activity on BLM melanoma cells in the Matrigel invasion assay, we were intrigued to verify how its effect on the viability of BLM cells would compare to that observed for the MCF-7 cell lines. Hence, MTT and SRB assays on this melanoma cell line were conducted for different concentrations of compound 49 (FIG. 7) (De Rijck, 2010).

A reduction in total protein content of 20% was observed upon treatment with 1 and 10 $\mu mol \cdot L^{-1}$ of the compound (p<0.01). A similar trend was appreciable at 100 $\mu mol \cdot L^{-1}$, but no significance was obtained in this case due to the large standard deviation (p=0.23). At 0.1 $\mu mol \cdot L^{-1}$, no effect was apparent. A clear dose-response pattern was obtained between mitochondrial activity and 4-fluoro-3',4',5'-trimethoxychalcone. All treatments resulted in a highly significant reduction of BLM cell viability (p<0.01), with a maximum reduction of 76% at a concentration of 100 $\mu mol \cdot L^{-1}$. The effects obtained at 0.1 and 1 $\mu mol \cdot L^{-1}$ were much smaller (22 and 27%, respectively). Solvent treatment caused a reduction of 13% in mitochondrial activity (p<0.05).

In order to verify whether the antiproliferative effects of compound 49, witnessed in BLM and MCF-7/6 cells at high concentrations, were cell specific, additional SRB and MTT assays on a further five cell lines (HCT8-E11, TR146, FaDu, 3T3-L1 and CT5.3) were conducted (FIG. 8). The results for MCF-7/6 cells were added to facilitate comparison.

The CT5.3 cell line consists of human myofibroblasts which were isolated from a colon tumor (Van Hoorde et al., 1999). 3T3-L1 cells are murine fibroblasts, originating from embryo's of Swiss mice (Todaro and Green, 1963). HCT8-E11, FaDu and TR146 are human epithelial cancer cell lines. The TR146 cell line consists of buccal cells isolated from a lymph node metastase in the neck (Clare Hall Laboratories) (Rupniak H T. et al., 1985). FaDu cells (Unibioscreen S.A.) were isolated from a hypopharyngeal carcinoma (Rangan S R., 1972). HCT-8/E11 is a colon carcinoma cell line, which was subcloned from the HCT-8 cell line (ATCC) (Vermeulen et al., 1995).

Upon a 24 h incubation period, no significant differences in total protein content were observed for a 1 or 10 $\mu mol \cdot L^{-1}$ treatment with compound 49 (FIG. 8). At the latter concentration, however, a decreasing trend was observed for HCT8-E11 (-27%), 3T3 (-20%), CT5.3 (-15%) en MCF-7/6 (-10%) cells. Under identical conditions, a significant reduction had been observed form BLM cells (-20%, FIG. 7).

When assessing mitochondrial activity, however, significant differences between solvent and compound treatment were observed (FIG. 8). At 1 $\mu mol \cdot L^{-1}$, an increase of 7% was observed for TR146 cells. FaDu and MCF-7/6 cells exhibited the same trend, but without significance; nevertheless, these results concord with the observations made for MCF-7/6 cells after 144 h of incubation (FIG. 6).

At an elevated concentration (10 $\mu mol \cdot L^{-1}$), 4-fluoro-3',4', 5'-trimethoxychalcone 49 engendered a significant reduction in mitochondrial activity in all cell lines at the 24 h time point. This decrease in viability was the strongest for MCF-7/6, HCT8-E11 and BLM cells (40%, FIG. 7 and FIG. 8). In the 3T3, TR146 and FaDu cell lines, a reduction of 30% was obtained. Remarkably, CT5.3 cells were less sensitive to compound 49, as the decrease in mitochondrial activity only amounted to 22% for this myofibroblast cell line.

In all, the antiproliferative activity of 4-fluoro-3',4',5'-trimethoxychalcone 49 is moderately cell specific, and can predominantly be appreciated when assessing mitochondrial activity. HCT8-E11 colon carcinoma cells displayed the highest sensitivity for compound 49, while CT5.3 cells were least susceptible to the effects mediated by this propenone.

Some general conclusions regarding the antiproliferative effects of the chalcone-like compounds can be made from the above presented data:

When focusing on compound 49, appreciable reductions (~50%) in both total protein content and mitochondrial activity were observed at elevated concentrations (10-100 $\mu mol \cdot L^{-1}$) in MCF-7/6, MCF-7/LucF5 and HCT8-E11 cells. In several other cell lines, comparable alteration in mitochondrial activity were appreciated, but total protein content was almost unaffected. Thus, compound 49 mediates a reduction in cell viability at micromolar concentrations, with the largest effect on the MCF-7 and HCT8 cell lines.

At submicromolar levels, however, no important reductions in cell viability were observed in the MCF-7/6, MCF-7/LucF5 and BLM cell lines. Hence, the anti-invasive potency of compound 49 at nanomolar concentrations cannot be attributed to growth-related effects.

REFERENCES

Abdel Bar F M, Khanfar M A, Elnagar A Y, Badria F A, Zaghloul A M, Ahmad K F, Sylvester P W, El Sayed K A. Bioorg Med Chem. 2010 Jan. 15; 18(2):496-507. Design and pharmacophore modeling of biaryl methyl eugenol analogs as breast cancer invasion inhibitors.

Alonso F, Riente P, Yus M. Nickel nanoparticles in hydrogen transfer reactions. Acc Chem Res. 2011, 44, 379-391.

Arap, W.; Pasqualini, R.; Ruoslahti, E. Cancer Treatment by Targeted Drug Delivery to Tumor Vasculature in a Mouse Model. *Science* 1998, 279, 377-380.

Arguello, F.; Baggs, R. B.; Frantz, C. N. A murine model of experimental metastasis to bone and bone marrow. *Cancer Res.* 1988, 48, 6876-6881.

Atassi, G.; dumont, P.; Vandendris, M. Investigation of the in vivo anti-invasive and anti-metastatic effect of desacetyl vinblastine amide sulphate or vindesine. *Invasion Metastasis* 1982, 2, 217-231.

Bandari R, Höche T, Prager A, Dirnberger K, Buchmeiser M R. Ring-Opening Metathesis Polymerization Based Pore-Size-Selective Functionalization of Glycidyl Methacrylate Based Monolithic Media: Access to Size-Stable Nanoparticles for Ligand-Free Metal Catalysis. Chemistry. 2010, 16, 4650-4658.

Bhat B A, Dhar K L, Puri S C, Saxena A K, Shanmugavel M, Qazi G N. Synthesis and biological evaluation of chalcones and their derived pyrazoles as potential cytotoxic agents. Bioorg Med Chem Lett. 2005 Jun. 15; 15(12):3177-80.

Bhagat, S.; Sharma, R.; Sawant, D. M.; Sharma, L.; Chakraborti, A. K. LiOH.H2O as a novel dual activation catalyst for highly efficient and easy synthesis of 1,3-diaryl-2-propenones by Claisen-Schmidt condensation under mild conditions. *J. Mol. Cat. A.* 2006, 244, 20-24.

Bracke, M. E.; Boterberg, T.; Mareel, M. M. Chick Heart Invasion Assay. In *Methods in Molecular Medicine*, Vol. 58: *Metastasis Research Protocols*, Vol. 2: *Cell Behavior In Vitro and In Vivo*; Brooks, S. A., Schumacher, U., Eds.; Humana Press Inc.; Totowa, N. J., 2001; pp 91-102.

Bracke M E, Vanhoecke B W, Derycke L, Bolca S, Possemiers S, Heyerick A, Stevens C V, De Keukeleire D, Depypere H T, Verstraete W, Williams C A, McKenna S T, Tomar S, Sharma D, Prasad A K, DePass A L, Parmar V S. Plant polyphenolics as anti-invasive cancer agents. Anticancer Agents Med Chem. 2008 February; 8(2):171-85.

Chiaradia, L. D.; dos Santos, R.; Vitor, C. E.; Vieira, A. A.; Leal, P. C.; Nunes, R. J.; Calixto, J. B.; Yunes, R. A. Synthesis and pharmacological activity of chalcones derived from 2,4,6-trimethoxyacetophenone in RAW 264.7 cells stimulated by LPS: Quantitative structure-activity relationships. *Bioorg. Med. Chem.*, 2008, 16, 658-667.

Ducki, S.; Rennison, D.; Woo, M.; Kendall, A.; Fournier Dit Chabert, J.; McGown, A. T.; Lawrence, N. J. Combretastatin-like chalcones as inhibitors of microtubule polymerization. Part 1: Synthesis and biological evaluation of antivascular activity. *Bioorg. Med. Chem.*, 2009, 17, 7698-7710.

Dureja, P. Photodimerization of aryl β-(2-furyl)-vinyl ketones. *Indian Journal of Chemistry, Section B: Organic Chemistry Including Medicinal Chemistry* 1987, 26B, 1173-1175.

Edwards M L, Stemerick D M, Sunkara P S. Chalcones: a new class of antimitotic agents. J Med Chem. 1990 July; 33(7): 1948-54.

Hung, T.-T.; Chan, J.; Russell, P. J.; Power, C. A. Zoledronic Acid Preserves Bone Structure and Increases Survival but Does Not Limit Tumour Incidence in a Prostate Cancer Bone Metastasis Model. *PLoS ONE* 2011, 6 (e-journal, no page numbers).

Jain, R. K.; Duda, D. G.; Clark, J. W.; Loeffler, J. S. Lessons from phase III clinical trials on anti-VEGF therapy for cancer. *Nat. Clin. Pract. Oncol.* 2006, 3, 24-40.

Katritzky, A. R.; Pacureanu L. M.; Slavov, S.; Dobchev, D. A.; Karelson, M. QSAR study of antiplatelet agents. *Bioorg. Med. Chem.* 2006, 14, 7490-7500.

Kauffmann, H.; Kieser, F. Basic function of methoxyl. *Ber. Dtsch. Chem. Ges.*, 1914, 46, 3788-3801.

Kumar, A. Zirconium chloride-catalyzed efficient synthesis of 1,3-diary)-2-propenones in solvent-free conditions via aldol condensation. *Journal of Molecular Catalysis A: Chemical* 2007, 274, 212-216.

Kumar R, Mohanakrishnan D, Sharma A, Kaushik N K, Kalia K, Sinha A K, Sahal D. Reinvestigation of structure-activity relationship of methoxylated chalcones as antimalarials: synthesis and evaluation of 2,4,5-trimethoxy substituted patterns as lead candidates derived from abundantly available natural β-asarone. Eur J Med Chem. 2010, 45, 5292-5301.

Loska, Rafal; Voila, Chandra M. Rao; Vogel, Pierre Iron-catalyzed Mizoroki-Heck cross-coupling reaction with styrenes Advanced Synthesis & Catalysis, 2008, 350, 2859-2864.

Mareel et al. Invasion promoter versus invasion suppressor molecules: the paradigm of E-cadherin, *Mol. Biol. Rep.* 1994, 19, 45-67

*Molecular Descriptors in QSAR/QSPR*; Karelson, M.; Wiley-Interscience, 2000; pp. 227.

Mosmann, T. Rapid colorimetric assay for cellular growth and survival: Application to proliferation and cytotoxicity assays. *J. Immunol. Methods* 1983, 65, 55-63.

Mukherjee, S.; Kumar, V.; Prasad, A. K.; Raj, H. G.; Bracke, M. E.; Olsen, C. E.; Jain, S. C.; Parmar, V. S. Synthetic anc Biological Activity Evaluation Studies on Novel 1,3-Diarylpropenones. *Bioorg. Med. Chem.* 2001, 9, 337-345.

Okunrobo L O, Usifoh C O, Uwaya J O. Anti-inflammatory and gastroprotective properties of some chalcones. Acta Pol Pharm. 2006, 63, 195-199.

Parmar, V. S.; Bracke, M. E.; Philippe, J.; Wengel, J.; Jain, S. C.; Olsen, C. E.; Bisht, K. S.; Sharma, N. K.; Courtens, A.; Sharma, S. K.; Vennekens, K.; Van Marck, V.; Singh, S. K.; Kumar, N.; Kumar, A.; Malhotra, S.; Kumar, R.; Rajwanshi, V. K.; Jain, R.; Mareel, M. M. Anti-Invasive Activity of Alkaloids and Polyphenolics in Vitro. *Bioorg. Med. Chem.* 1997, 5, 1609-1619.

Parmar V. S. et al. Synthesis and anti-invasive activity of novel 1,3-diarylpropenones. Indian journal of chemistry 1998, 37B, 628-643.

Parmar, V. S.; Sharma, N. K.; Husain, M.; Watterson, A. C.; Kumar, J.; Samuelson, L. A.; Cholli, A. L.; Prasad, A. K.; Kumar, A.; Malhotra, S.; Kumar, N.; Jha, A.; Singh, A.; Singh, I.; Hiamnshu; Vats, A.; Shakil, N. A.; Trikha, S.; Mukherjee, S.; Sharma, S. K.; Singh, S. K.; Kumar, A.; Jha, H. N.; Olsen, C. E.; Stove, C. P.; Bracke, M. E.; Mareel, M. M. Synthesis, Characterization and In Vitro Anti-Invasive Activity Screening of Polyphenolic and Heterocyclic Compounds. *Bioorg. Med. Chem.* 2003, 11, 913-929.

Pennacchietti, S. et al. Hypoxia promotes invasive growth by transcriptional activation of the met protooncogene. *Cancer Cell* 3, 347-361 (2003).

Rasheed, L. Synthesis of Some Benzalacetophenones and Their Imino Derivatives *Asian J. Chem.* 2007, 19, 5057-5067.

Reth, M. Immunodeficiency: Trapping the nude mouse gene. *Curr. Biol.* 1995, 5, 18-20.

Shafie, S. M. Estrogen and the growth of breast cancer: new evidence suggests indirect action. *Science* 1980, 209, 701-702.

Rangan, S. R. A new human cell line (FaDu) from a hypopharyngeal carcinoma. *Cancer* 1972, 29, 117-121. Robinson T P, Hubbard R B 4th, Ehlers T J, Arbiser J L, Goldsmith D J, Bowen J P. Synthesis and biological evaluation of aromatic enones related to curcumin. Bioorg Med Chem. 2005 Jun. 2; 13(12):4007-13.

Romagnoli R, Baraldi P G, Carrion M D, Cara C L, Cruz-Lopez O, Preti D, Tolomeo M, Grimaudo S, Di Cristina A, Zonta N, Balzarini J, Brancale A, Sarkar T, Hamel E. Design, synthesis, and biological evaluation of thiophene analogues of chalcones. Bioorg Med Chem. 2008 May 15; 16(10):5367-76.

Rupniak, H. T.; Rowlatt, C.; Lane, E. B.; Steele, J. G.; Trejdosiewicz, L. K.; Laskiewicz, B.; Povey, S.; Hill, B. T. Characteristics of four new human cell lines derived from squamous cell carcinomas of the head and neck. *J. Natl. Cancer Inst.* 1985, 75, 621-635.

Smith, W. Responses of laboratory animals to some injectable aneaesthetics. *Lab. Anim.* 1993, 27, 30-39.

Soule, H. D.; Vazquez, J.; Long, A.; Albert, S.; Brennan, M. J. Human cell line from pleural effusion derived from breast carcinoma. J. Natl. Cancer Inst. 1973, 51, 1409-1413.

Sun, Xun; Zhu, Jun; Zhong, Chen; Izumi, Ken-Ji; Zhang, Chen A concise and convenient synthesis of stilbenes via benzils and arylmethyldiphenylphosphine oxides Chinese Journal of Chemistry, 2007, 25, 1866-1870.

Teh, J.; Bee J. 3-(2-Furyl)-1-(4-methoxyphenyl)prop-2-en-1-one. *Acta Crystallographica, Section E: Structure Reports Online* 2006, VE62(4), 01526-01528.

Todaro, G. J.; Green, H. Quantitative studies of the growth of mouse embryo cells in culture and their development into established lines. *J. Cell Biol.* 1963, 17, 299-313.

Vanhoecke B. W., Depypere H. T., De Beyter A., Sharma S. K., Parmar V. S., De Keukeleire D., Bracke M. E.; New anti-invasive compounds: Results from the Indo-Belgian screening program. *Pure Appl. Chem.* 2005, 1, 65-75.

Van Hoorde, L.; Braet, K.; Mareel, M. The N-cadherin/catenin complex in colon fibroblasts and myofibroblasts. *Cell Adhes. Commun.* 1999, 7, 139-150.

Vermeulen, S. J.; Bruyneel, E. A.; Bracke, M. E.; de Bruyne, G K.; Vennekens, K. M.; Vleminckx, K. L.; Berx, G. J.; van Roy, F. M.; Mareel, M. M. Transition from the noninvasive to the invasive phenotype and loss of α-catenin in human colon cancer cells. *Cancer Res.* 1995, 55, 4722-4728.

Welsch, C. W.; Swim, E. L.; McManus, M. J.; White, A. C.; McGrath, C. M. Estrogen induced growth of human breast cancer cells (MCF-7) in athymic nude mice is enhanced by secretions from a transplantable pituitary tumor. *Cancer Lett.* 1981, 14, 309-316.

Wetterwald, A.; van der Pluijm, G.; Que, I.; Sijmons, B.; Buijs, J.; Karperien, M.; Löwik, C. W. G. M.; Gautschi, E.; Thalmann, G. N.; Cecchini, M. G. Optical Imaging of Cancer Metastasis to Bone Marrow. A Mouse Model of Minimal Residual Disease. *Am. J. Pathol.* 2002, 160, 1143-1153.

The invention claimed is:

1. A method for inhibiting the invasiveness of tumor cells in a subject, said method comprising contacting said cells with a pharmaceutically effective amount of a compound, wherein said compound has Formula I:

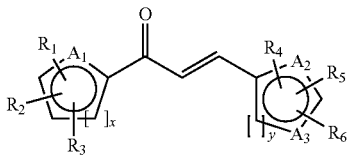

I or a stereoisomer, tautomer, racemic, pro- or predrug, salt, hydrate, or solvate thereof, wherein:

$A_1$, $A_2$ and $A_3$ are independently selected from C and O;
$R_1$, $R_2$, $R_3$, $R_4$, $R_5$, and $R_6$ are each independently selected from —H, -halo, —$C_{1-6}$ alkyl, and —O—$C_{1-6}$ alkyl; and
x and y are each independently selected from 1 or 2; and
wherein said compound has a predicted lowest active concentration of 0.1 μM or less as predicted by an in silico method to predict the anti-invasive activity of said compound; said in silico method comprising the steps of:
(1) determining theoretical molecular descriptors for said compound, wherein the theoretical molecular descriptors comprise:
(a) maximal antibonding contribution of one molecular orbital ($D_1$),
(b) partial surface area for atom C ($D_2$),
(c) final heat of formation/# atoms ($D_3$),
(d) XY Shadow/XY Rectangle ($D_4$),
(e) minimum 1-electron reaction index for an oxygen atom ($D_5$), and
(f) polarity parameter ($D_6$); and
(2) determining log $c_{min}$ for said compound, wherein log $c_{min}$ is determined in accordance with the following Equation:

$$\log c_{min} = -58.90 + (28.63 \times D_1) - (16.29 \times D_2) + (1.093 \times D_3) + (9.904 \times D_4) - (116.3 \times D_5) + (17.01 \times D_6)$$

wherein:
when log $c_{min}$ is $>-1.5$ and $\leq -0.5$, said compound is predicted to have anti-invasive activity at a lowest active concentration of about 0.1 μM,
when log $c_{min}$ is $>-2.5$ and $\leq -1.5$, said compound is predicted to have anti-invasive activity at a lowest active concentration of about 0.01 μM, and
when log $c_{min}$ is $\leq -2.5$, said compound is predicted to have anti-invasive activity at a lowest active concentration of <0.01 μM.

2. The method according to claim 1, wherein:
x and y are independently selected from 1 or 2, and
at least one of x and y is 1.

3. The method according to claim 1, wherein:
$A_1$ is C, one of $A_2$ and $A_3$ is C and the other one of $A_2$ and $A_3$ is O;
$R_1$, $R_2$, and $R_3$ are each independently selected from —H, -halo, and —O—$C_{1-6}$ alkyl;
$R_4$, $R_5$, and $R_6$ are each —H;
x is 2; and
y is 1.

4. The method according to claim 1, wherein the compound has Formula Ia:

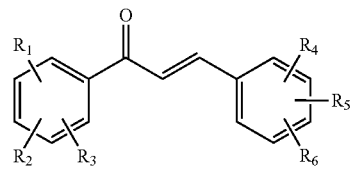

Ia wherein:
$R_1$, $R_2$, $R_3$, $R_4$, $R_5$, and $R_6$ are each independently selected from —H, -halo, —$C_{1-6}$ alkyl, and —O—$C_{1-6}$ alkyl.

5. The method according to claim 1, wherein the compound has Formula Ia, wherein:
$R_1$, $R_2$, and $R_3$, are each independently selected from —H, -halo, and —O—$C_{1-6}$ alkyl;
$R_4$, and $R_5$ are each —H; and
$R_6$ is -halo.

6. The method according to claim 1, wherein the compound has Formula Ib:

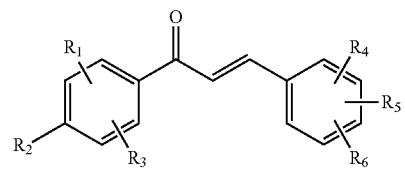

Ib wherein:
$R_1$, $R_3$, $R_4$, $R_5$, and $R_6$ are each independently selected from —H, -halo, and —O—$C_{1-6}$ alkyl; and
$R_2$ is selected from -halo and —O—$C_{1-6}$ alkyl.

7. The method according to claim 1, wherein the compound has Formula Ic:

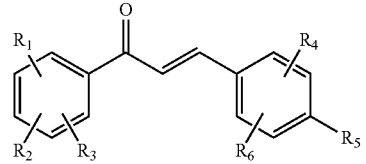

Ic wherein:
$R_1$, $R_2$, $R_3$, $R_4$, and $R_6$ are each independently selected from —H, -halo, and —O—$C_{1-6}$ alkyl; and
$R_5$ is selected from -halo, and —O—$C_{1-6}$ alkyl.

8. The method according to claim 1, wherein the compound has Formula Id:

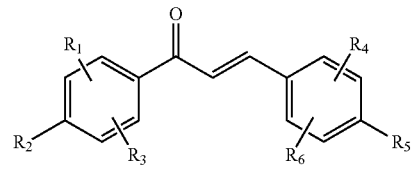

Id wherein:
$R_1$, $R_3$, $R_4$, and $R_6$ are each independently selected from —H, -halo, and —O—$C_{1-6}$ alkyl; and R₂ and R₅ are each independently selected from -halo and —O—C$_{1-6}$ alkyl.

9. The method according to claim 1; wherein said compound is selected from:
   (2E)-3-(4-fluorophenyl)-1-(3,4,5-trimethoxyphenyl)prop-2-en-1-one;
   (2E)-3-(4-chlorophenyl)-1-(4-methoxyphenyl)prop-2-en-1-one;
   (2E)-1-(4-methoxyphenyl)-3-(2,4,6-trimethoxyphenyl)prop-2-en-1-one;
   (2E)-3-(3-fluorophenyl)-1-(4-fluorophenyl)prop-2-en-1-one;
   (2E)-3-(furan-2-yl)-1-(3,4,5-trimethoxyphenyl)prop-2-en-1-one;
   (2E)-1-(2,6-dimethoxyphenyl)-3-(furan-2-yl)prop-2-en-1-one;
   (2E)-1-(4-fluorophenyl)-3-(furan-3-yl)prop-2-en-1-one; and
   (2E)-1,3-di(furan-2-yl)prop-2-en-1-one.

10. The method according to claim 1, wherein the compound is formulated as part of a pharmaceutical composition further comprising a pharmaceutically acceptable carrier, excipient and/or diluent, and optionally an adjuvant.

11. The method according to claim 1, wherein the invasion of tumor cells into the surrounding tissue is inhibited in a subject having a condition associated with undesired cell migration.

12. A method according to claim 11, wherein said condition is associated with solid malignant tumors.

* * * * *